US007250407B2

(12) United States Patent
Dasseux et al.

(10) Patent No.: US 7,250,407 B2
(45) Date of Patent: Jul. 31, 2007

(54) GENE THERAPY APPROACHES TO SUPPLY APOLIPOPROTEIN A-I AGONISTS AND THEIR USE TO TREAT DYSLIPIDEMIC DISORDERS

(75) Inventors: Jean-Louis Dasseux, Mannheim (DE); Renate Sekul, Ladenburg (DE); Klaus Büttner, Epfenbach (DE); Isabelle Cornut, Edingen-Neckarhausen (DE); Günther Metz, Edingen-Neckarhausen (DE); Jean Dufourcq, Pessac (FR)

(73) Assignee: Pfizer Inc., New York, NY (US)

( * ) Notice: Subject to any disclaimer, the term of this patent is extended or adjusted under 35 U.S.C. 154(b) by 238 days.

(21) Appl. No.: 10/991,217

(22) Filed: Nov. 16, 2004

(65) Prior Publication Data
US 2005/0148513 A1   Jul. 7, 2005

Related U.S. Application Data

(63) Continuation of application No. 10/283,599, filed on Oct. 29, 2002, now Pat. No. 6,844,327, which is a continuation of application No. 08/940,136, filed on Sep. 29, 1997, now Pat. No. 6,518,412.

(51) Int. Cl.
A61K 31/70    (2006.01)
C07H 21/04    (2006.01)

(52) U.S. Cl. .................... 514/44; 536/23.1; 536/252.3; 536/320.1

(58) Field of Classification Search .................. 514/44; 536/23.1, 252.3, 320.1
See application file for complete search history.

(56) References Cited

U.S. PATENT DOCUMENTS

| 4,229,360 | A  | 10/1980 | Schneider et al. |
| 4,411,894 | A  | 10/1983 | Schrank et al. |
| 4,643,988 | A  | 2/1987  | Segrest et al. |
| 4,857,319 | A  | 8/1989  | Crowe et al. |
| 4,880,635 | A  | 11/1989 | Janoff et al. |
| 6,518,412 | B1 | 2/2003  | Dasseux et al. |

FOREIGN PATENT DOCUMENTS

| EP | 0 162 414  | 5/1985  |
| WO | WO 93/25581 | 12/1993 |
| WO | WO 94/13819 | 6/1994  |
| WO | WO 96/04916 | 2/1996  |
| WO | WO 96/37608 | 11/1996 |

OTHER PUBLICATIONS

Anantharamaiah, 1986, *Methods in Enzymology 128*:627-647.
Anantharamaiah et al., 1985, *J. Biol. Chem. 260*:10248-10255.
Anantharamaiah et al., 1986, *Proteins of Biological Fluids 34*:63-66.
Anantharamaiah et al., 1990, *Arteriosclerosis 10*(1):95-105.
Anantharamaiah et al., 1991, *Adv. Exp. Med. Biol. 285*:131-140.
Badimon et al., 1990, *J. Clin. Invest. 85*:1234-1241.
Barrans et al., 1996, *Biochim. Biophys. Acta 1300*: 73-85.
Beitz et al., 1992, *Prostaglandins, Leukotrienes and Essential Fatty Acids 47*:149-152.
Berard et al., 1997, *Nature Medicine 3*(7):744-749.
Blondelle et al., 1993, *Biochim. Biophys. Acta 1202*:331-336.
Brasseur, 1991, *J. Biol. Chem. 266*(24):16120-16127.
Brasseur et al., 1990, *Biochim. Biophys. Acta 1043*:245-252.
Brasseur et al., 1993, *Biochim. Biophys. Acta 1170*:1-7.
Brouilette and Anantharamaiah, 1995, *Biochim. Biophys. Acta 1256*:103-129.
Burkey et al., 1992, *Circulation, Supplement I 86*:I-472, Abstract No. 1876.
Burkey et al., 1995, *J. Lipid Res. 36*:1463-1473.
Cheung et al., 1991, *Lipid Res. 32*:383-394.
Chung et al., 1985, *J. Biol. Chem. 260*:10256-10262.
Collet et al., 1997, *Journal of Lipid Research 38*:634-644.
Corijn et al., 1993, *Biochim. Biophys. Acta 1170*:8-16.
Davidson et al., 1994, *J. Biol. Chem. 269*(37):22975-22982.
Davidson et al., 1996, *Proc. Natl. Acad. Sci. U.S.A. 93*:13605-13610.
Deamer et al., 1983, *Liposomes* (Ostro, Ed.), Marcel Dekker, Inc., New York.
Demoor et al., 1996, *24th European Chemical Peptide Symposium*.
Demoor et al., 1996, *Eur. J. Biochem. 239*:74-84.
Dufourcq et al., 1986, *Biochim. Biophys. Acta 859*:33-48.
Duverger, 1996, *Circulation 94*:713-717.
Duverger et al., 1996, *Arterioscler. Thromb. Vasc. Biol. 16*:1424-1429.
Emmanuel et al., 1994, *J. Biol. Chem. 269*(47):29883-29890.
Epand et al., 1987, *J. Biol. Chem. 262*:9389-9396.
Epand et al., 1995, *Biopolymers (Peptide Science) 37*:319-338.
Esposito et al., 1997, *Biopolymers 41*:27-35.
Fielding and Fielding, 1995, *J. Lipid Res. 36*:211-228.
Fournier et al., 1996, *J. Lipid Res. 37*:1704-1711.
Francone et al., 1995, *J. Clinic. Invet. 96*:1440-1448.
Frank et al., 1997, *Biochemistry 36*:1789-1806.
Fruchart and Ailhaud, 1992, *Clin. Chem. 38*:793-797.
Fukushima et al., 1979, *J. Am. Chem. Soc. 101*(13):3703-3704.
Fukushima et al., 1980, *J. Biol. Chem. 255*:10651-10657.
Garber et al., 1992, *Arteriosclerosis and Thrombosis 12*:886-894.
Gordon et al., 1989, *Circulation 79*:8-15.

(Continued)

*Primary Examiner*—Tekchand Saidha
(74) *Attorney, Agent, or Firm*—Gregg C. Benson; Nicholas I. Slepchuk

(57) ABSTRACT

The invention relates to genetic approaches to supply nucleotide sequences encoding modified forms of the native forms of apolipoprotein A-I (ApoA-I): mature ApoA-I, preproApoA-I and proApoA-I; including native ApoA-I modified to contain ApoA-I agonists, peptides which mimic the activity of ApoA-I; ApoA-I superagonists, peptides which exceed the activity of native ApoA-I; and modified native ApoA-I having one or more amphipathic helices replaced by the nucleotide sequences of one or more ApoA-I agonists; for the treatment of disorders associated with dyslipoproteinemia, including cardiovascular disease, atherosclerosis, restenosis, hyperlipidemia, and other disorders such as septic shock.

14 Claims, 5 Drawing Sheets

OTHER PUBLICATIONS

Gordon and Rifkind, 1989, *N. Eng. J. Med.* 321:1311-1316.
Groebke et al., 1996, *Proc. Natl. Acad. Sci. U.S.A.* 93:4025-4029.
Hirano et al., 1997, *Arterioscler. Thromb, Vasc. Biol.* 17(6):1053-1059.
Holvoet et al., 1995, *Biochemistry* 34:13334-13342.
Hope et al., 1986, *Chemistry and Physics of Lipids* 40:89-107.
Huyghues-Despointes et al., 1995, *Biochemimstry* 34(41):13267-13271.
Ji and Jonas, 1995, *J. Biol. Chem.* 270:11290-11297.
Johnson et al., 1971, *Biocheim. Biophys. Acta* 233:820.
Jonas, 1986, *Methods in Enzymol.* 128:553-582.
Jonas, 1992, "Lipid-Binding Properties of Apolipoproteins," *In: Structure and Function of Apolipoproteins*, CRC Press, Ch. 8, pp. 217-250.
Kaiser, 1970, *Anal. Biochem.* 34:595-598.
Kaiser and Kezdy, 1983, *Proc. Natl. Acad. Sci. U.S.A.* 80:1137-1143.
Kannelis et al., 1980, *J. Biol. Chem.* 255(3):11464-11472.
Koizumi et al., 1988, *J. Lipid Res.* 29:1405-1415.
Kneib-Cordonnier et al., 1990, *Int. J. Peptide Protein Res.* 35:527-538.
Knott et al., 1985, *Science* 230:37-43.
Labeur et al., 1997, *Arterioscler. Throm. Vasc. Biol.* 17:580-588.
Lacko and Miller, 1997, *J. Lip. Res.* 38:1267-1273.
Li et al., 1996, *Proc. Natl. Acad. Sci. U.S.A.* 93:6676-6681.
Lins et al., 1993, *Biochim. Biophys. Acta Biomembranes* 1151:137-142.
Liu et al., 1994, *J. Lipid Res.* 35:2263-2267.
Livingstone, 1974, *Methods in Enzymology: Immunoaffinity Chromatography of Proteins* 34:723-731.
Lund-Katz et al., 1990, *J. Biol. Chem.* 265(21):12217-12223.
Lund-Katz et al., 1995, *Biochemistry* 34:9219-9226.
Marqusee et al., 1987, *Proc. Natl. Acad. Sci. U.S.A.* 84(24):8898-8902.
Mendez et al., 1994, *J. Clin. Invest.* 94:1698-1705.
Mezdour et al., 1995, *Atherosclerosis* 113:237-246.
Miller, 1987, *Amer. Heart* 113:589-597.
Milner-White and Poet, 1987, *Trends Biochem. Sci.* 12:189-192.
Minnich et al., 1992, *J. Biol. Chem.* 267:16553-16560.
Mishra et al., 1994, *J. Biol. Chem.* 269(10):7185-7191.
Mishra et al., 1995, *J. Biol. Chem.* 270(4):1602-1611.
Nakagawa et al., 1985, *J. Am. Chem. Soc.* 107:7087-7092.
Nedelec et al., 1989, *Biochimie* 71:145-151.
Palgunachair et al., 1996, *Arterioscler. Thromb. Vasc. Biol.* 16:328-338.
Paszty et al., 1994, *J. Clin. Invest.* 94:899-903.
Plump et al., 1994, *Proc. Natl. Acad. Sci. U.S.A.* 91:9607-9611.
Ponsin et al., 1984, *Biochemistry* 23:5337-5342.
Ponsin et al., 1986, *J. Biol. Chem.* 261(20):9202-9205.
Pownall et al., 1980, *Proc. Natl. Acad. Sci. U.S.A.* 77(6):3154-3158.
Rogers et al., 1997, *Biochemistry* 36:288-300.
Rosseneu et al., *In: Structure and Function of the Lipoproteins*, Ch. 6, 159-183, CRC Press, Inc., 1992.
Rosseneu and Labeur, 1995, *FASEB J.* 9:768-776.
Rubin et al., 1991, *Nature* 353:265-267.
Schnölzer and Kent, 1992, *Science* 256:221-225.
Schultz et al., 1993, *Nature* 365:762-764.
Segrest, 1974, *FEBS Lett.* 38:247-253.
Segrest, 1976, *FEBS Lett.* 69(1):111-114.
Segrest et al., 1983, *J. Biol. Chem.* 258:2290-2295.
Segrest et al., 1990, *PROTEINS: Structure, Function and Genetics* 8:103-117.
Segrest et al., 1992, *J. Lipid Res.* 33:141-166.
Segrest et al., 1994, *Advances in Protein Chemistry* 45:303-369.
Sorci-Thomas et al., 1993, *J. Biol. Chem.* 268:21403-21409.
Sorci-Thomas et al., 1997, *J. Biol. Chem.* 272(11):7278-7284.
Sparks et al., 1995, *J. Biol. Chem.* 270(10):5151-5157.
Sparrow and Gotto, 1980, *Ann. N.Y. Acad. Sci.* 348:187-211.
Sparrow and Gotto, 1982, *CRC Crit. Rev. Biochem.* 13:87-107.
Sparrow and Gotto, Ch. 10: "Lipid-Protein Interactions: Structure-Function Relationships".
Sparrow et al., 1981, *In:* "Peptides: Synthesis-Structure-Function," Roch and Gross, Eds., Pierce Chem. Co., Rockford, IL, 253-256.
Spuhler et al., 1994, *J. Biol. Chem.* 269(39):23904-23910.
Subbarao et al., 1988, *PROTEINS: Structure, Function and Genetics* 3:187-198.
Tam, 1988, *Proc. Natl. Acad. Sci. U.S.A.* 85:5409-5413.
Tytler et al., 1993, *J. Biol. Chem.* 268(29):22112-22118.
Vanloo et al., 1992, *Biochim. Biophys. Acta* 1128:258-266.
Venkatachalapathi et al., 1991, *Mol. Conformation and Biol. Interactions, Indian Acad. Sci. B*:585-596.
Venkatachalapathi et al., 1993, *PROTEINS: Structure, Function and Genetics* 15:349-359.
Wang et al., 1996, *Biochim. Biophys. Acta* 1301:174-184.
Wilmot and Thornton; 1988, *J. Mol. Biol.* 203:221-232.
Yancey et al., 1995, *Biochemistry* 34:7955-7965.
Yokoyama et al., 1980, *J. Biol. Chem.* 255(15):7333-7339.
Ngo et al., "Computational Complexity, Protein Structure Prediction, and the Levinthal Paradox", in the Protein Folding Problem and Tertiary Structure Prediction, Merz, Jr., Ed. Birkhauser Boston, pp. 492-494.
Rudinger, p. 6 of Peptide Hormones, Parsons Ed. University Park Press.
Thornton et al., "Protein Engineering", Curr Opinion Biotech 6:367-369.

```
ATG AAA GCT GCG GTG CTG ACC TTG GCC GTG CTC TTC CTG ACG GGG AGC
Met Lys Ala Ala Val Leu Thr Leu Ala Val Leu Phe Leu Thr Gly Ser
 1           5                   10                  15

CAG GCT CGG CAT TTC TGG CAG CAA GAT GAA CCC CCC CAG AGC CCC TGG
Gln Ala Arg His Phe Trp Gln Gln Asp Glu Pro Pro Gln Ser Pro Trp
             20                  25                  30

GAT CGA GTG AAG GAC CTG GCC ACT GTG TAC GTG GAT GTG CTC AAA GAC
Asp Arg Val Lys Asp Leu Ala Thr Val Tyr Val Asp Val Leu Lys Asp
             35                  40                  45

AGC GGC AGA GAC TAT GTG TCC CAG TTT GAA GGC TCC GCC TTG GGA AAA
Ser Gly Arg Asp Tyr Val Ser Gln Phe Glu Gly Ser Ala Leu Gly Lys
         50                  55                  60

CAG CTA AAC CTA AAG CTC CTT GAC AAC TGG GAC AGC GTG ACC TCC ACC
Gln Leu Asn Leu Lys Leu Leu Asp Asn Trp Asp Ser Val Thr Ser Thr
 65              70                  75                  80

TTC AGC AAG CTG CGC GAA CAG CTC GGC CCT GTG ACC CAG GAG TTC TGG
Phe Ser Lys Leu Arg Glu Gln Leu Gly Pro Val Thr Gln Glu Phe Trp
                 85                  90                  95

GAT AAC CTG GAA AAG GAG ACA GAG GGC CTG AGG CAG GAG ATG AGC AAG
Asp Asn Leu Glu Lys Glu Thr Glu Gly Leu Arg Gln Glu Met Ser Lys
                100                 105                 110

GAT CTG GAG GAG GTG AAG GCC AAG GTG CAG CCC TAC CTG GAC GAC TTC
Asp Leu Glu Glu Val Lys Ala Lys Val Gln Pro Tyr Leu Asp Asp Phe
            115                 120                 125

CAG AAG AAG TGG CAG GAG GAG ATG GAG CTC TAC CGC CAG AAG GTG GAG
Gln Lys Lys Trp Gln Glu Glu Met Glu Leu Tyr Arg Gln Lys Val Glu
        130                 135                 140
```

FIG. 1

```
CCG CTG CGC GCA GAG CTC CAA GAG GGC GCG CGC CAG AAG CTG CAC GAG
Pro Leu Arg Ala Glu Leu Gln Glu Gly Ala Arg Gln Lys Leu His Glu
145             150             155             160

CTG CAA GAG AAG CTG AGC CCA CTG GGC GAG GAG ATG CGC GAC CGC GCG
Leu Gln Glu Lys Leu Ser Pro Leu Gly Glu Glu Met Arg Asp Arg Ala
            165             170             175

CGC GCC CAT GTG GAC GCG CTG CGC ACG CAT CTG GCC CCC TAC AGC GAC
Arg Ala His Val Asp Ala Leu Arg Thr His Leu Ala Pro Tyr Ser Asp
            180             185             190

GAG CTG CGC CAG CGC TTG GCC GCG CGC CTT GAG GCT CTC AAG GAG AAC
Glu Leu Arg Gln Arg Leu Ala Ala Arg Leu Glu Ala Leu Lys Glu Asn
            195             200             205

GGC GGC GCC AGA CTG GCC GAG TAC CAC GCC AAG GCC ACC GAG CAT CTG
Gly Gly ala Arg Leu Ala Glu Tyr His Ala Lys Ala Thr Glu His Leu
            210             215             220

AGC ACG CTC AGC GAG AAG GCC AAG CCC GCG CTC GAG GAC CTC CGC CAA
Ser Thr Leu Ser Glu Lys Ala Lys Pro Ala Leu Glu Asp Leu Arg Gln
225             230             235             240

GGC CTG CTG CCC GTG CTG GAG AGC TTC AAG GTC AGC TTC CTG AGC GCT
Gly Leu Leu Pro Val Leu Glu Ser Phe Lys Val Ser Phe Leu Ser Ala
            245             250             255

CTC GAG GAG TAC ACT AAG AAG CTC AAC ACC CAG TGA GGCGCCCGCC
Leu Glu Glu Tyr Thr Lys Lys Leu Asn Thr Gln  *
            260             265

GCCGCCCCCC TTCCCGGTGC TCAGAATA
```

FIG. 1 cont.

5'  CCT GTT CTT GAC CTC TTC CGT GAA CTT CTT AAC GAA GGC CTC
    GAG GCA CTG AAA CAG AAA CTA AAA 3'

5'  GGT GTT CTG GAC CTC TTC CGT GAA CTT CTT AAC GAA GGC CTA
    GCG CTA AAA CAA AAA CTA AAA 3'

5'  CCC GTG TTG GAC TTG TTC CGA GAA CTA CTA AAC GAA GGA CTA
    GAA TGG TTG AAA CTA AAA CTA AAA 3'

FIG. 2

5'   GGT GTT TTG GAA CTT TTC GAA AAC TTA TTG GAA AGA TTG TTG
     GAC GCA CTG CAA AAA AAA TTG AAA 3'

5'   CCA GTC TTG GAA CTT TTC GAG AAC TTG TGG GAG CGA TTG TTG
     GAT GCT TTG CAA AAA AAA TTG AAA 3'

5'   GCC GTG TTG GAG CTG TTC GAA AAC TTA TTA GAG CGA TTA TTA
     GAC GCA TTA CAG AAA AAA TTG AAA 3'

FIG. 3

5'  CCT GTG TTG GAC TTG TTC CGC GAG TTA TTA AAC GAG TTA TTA
    CAG AAA TTA AAA 3'

5'  CCT GTG TTG GAC TTG TTG CGA GAA TTA TTA GAG GAA TTA AAA
    CAA AAA CTA AAA 3'

5'  CCA TTA TTA GAA TTA TTT AAG GAA TTA TTG GAG GAG CTG GAA
    CAG GAA CTA GAA 3'

FIG. 4

```
                            SEQUENCE LISTING (1) GENERAL INFORMATION:

(iii) NUMBER OF SEQUENCES: 274

(2) INFORMATION FOR SEQ ID NO:1:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: None (ix) FEATURE:
             (A) NAME/KEY: Other
             (B) LOCATION: 16
             (D) OTHER INFORMATION: Xaa = Naphthylalanine (xi) SEQUENCE DESCRIPTION: SEQ ID NO:1:

Pro Val Leu Asp Leu Phe Arg Glu Leu Leu Asn Glu Leu Leu Glu Xaa
    1               5                  10                  15

Leu Lys Gln Lys Leu Lys
               20

(2) INFORMATION FOR SEQ ID NO:2:

(i) SEQUENCE CHARACTERISTICS:
             (A) LENGTH: 23 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:2:

Gly Val Leu Asp Leu Phe Arg Glu Leu Leu Asn Glu Leu Leu Glu Ala
    1               5                  10                  15

Leu Lys Gln Lys Leu Lys Lys
               20

(2) INFORMATION FOR SEQ ID NO:3:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:3:

Pro Val Leu Asp Leu Phe Arg Glu Leu Leu Asn Glu Leu Leu Glu Trp
    1               5                  10                  15

Leu Lys Gln Lys Leu Lys
```

(2) INFORMATION FOR SEQ ID NO:4:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

```
Pro Val Leu Asp Leu Phe Arg Glu Leu Leu Asn Glu Leu Leu Glu Ala
 1               5                  10                  15
Leu Lys Gln Lys Leu Lys
            20
```

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO:5:

```
Xaa Val Leu Asp Leu Phe Arg Glu Leu Leu Asn Glu Leu Leu Glu Ala
 1               5                  10                  15
Leu Lys Gln Lys Leu Lys Lys
            20
```

(2) INFORMATION FOR SEQ ID NO:6:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:6:

```
Pro Val Leu Asp Leu Phe Arg Glu Leu Leu Asn Glu Xaa Leu Glu Ala
 1               5                  10                  15
Leu Lys Gln Lys Leu Lys
            20
```

(2) INFORMATION FOR SEQ ID NO:7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None -continued

```
    (xi) SEQUENCE DESCRIPTION: SEQ ID NO:7:

Pro Val Leu Asp Leu Phe Lys Glu Leu Leu Asn Glu Leu Leu Glu Ala
1               5                   10                  15

Leu Lys Gln Lys Leu Lys
            20

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

Pro Val Leu Asp Leu Phe Arg Glu Leu Leu Asn Glu Gly Leu Glu Ala
1               5                   10                  15

Leu Lys Gln Lys Leu Lys
            20

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

Pro Val Leu Asp Leu Phe Arg Glu Leu Gly Asn Glu Leu Leu Glu Ala
1               5                   10                  15

Leu Lys Gln Lys Leu Lys
            20

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 17
        (D) OTHER INFORMATION: Xaa = Naphthylalanine (xi) SEQUENCE DESCRIPTION: SEQ ID NO:10:

Pro Val Leu Asp Leu Phe Arg Glu Leu Leu Asn Glu Leu Leu Glu Ala
1               5                   10                  15

Xaa Lys Gln Lys Leu Lys
            20

(2) INFORMATION FOR SEQ ID NO:11:

(i) SEQUENCE CHARACTERISTICS:
        (A) LENGTH: 22 amino acids
        (B) TYPE: amino acid
        (C) STRANDEDNESS: single
        (D) TOPOLOGY: linear
```

(ii) MOLECULE TYPE: None (xi) SEQUENCE DESCRIPTION: SEQ ID NO:11:

Pro Val Leu Asp Leu Phe Lys Glu Leu Leu Gln Glu Leu Leu Glu Ala
  1               5                  10                  15

Leu Lys Gln Lys Leu Lys
            20

(2) INFORMATION FOR SEQ ID NO:12:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:12:

Pro Val Leu Asp Leu Phe Arg Glu Leu Leu Asn Glu Leu Leu Glu Ala
  1               5                  10                  15

Gly Lys Gln Lys Leu Lys
            20

(2) INFORMATION FOR SEQ ID NO:13:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:13:

Gly Val Leu Asp Leu Phe Arg Glu Leu Leu Asn Glu Gly Leu Glu Ala
  1               5                  10                  15

Leu Lys Gln Lys Leu Lys
            20

(2) INFORMATION FOR SEQ ID NO:14:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 18
            (D) OTHER INFORMATION: Xaa = Orn
            (A) NAME/KEY: Other
            (B) LOCATION: 20
            (D) OTHER INFORMATION: Xaa = Orn
            (A) NAME/KEY: Other
            (B) LOCATION: 22
            (D) OTHER INFORMATION: Xaa = Orn (xi) SEQUENCE DESCRIPTION: SEQ ID NO:14:

Pro Val Leu Asp Leu Phe Arg Glu Leu Leu Asn Glu Leu Leu Glu Ala
  1               5                  10                  15

Leu Xaa Gln Xaa Leu Xaa
            20

(2) INFORMATION FOR SEQ ID NO:15:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

```
Pro Val Leu Asp Leu Phe Arg Glu Leu Trp Asn Glu Leu Leu Glu Ala
 1               5                  10                  15
Leu Lys Gln Lys Leu Lys
            20
```

(2) INFORMATION FOR SEQ ID NO:16:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

```
Pro Val Leu Asp Leu Leu Arg Glu Leu Leu Asn Glu Leu Leu Glu Ala
 1               5                  10                  15
Leu Lys Gln Lys Leu Lys
            20
```

(2) INFORMATION FOR SEQ ID NO:17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

```
Pro Val Leu Glu Leu Phe Lys Glu Leu Leu Gln Glu Leu Leu Glu Ala
 1               5                  10                  15
Leu Lys Gln Lys Leu Lys
            20
```

(2) INFORMATION FOR SEQ ID NO:18:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Gly Val Leu Asp Leu Phe Arg Glu Leu Leu Asn Glu Leu Leu Glu Ala
 1               5                  10                  15
Leu Lys Gln Lys Leu Lys
            20
```

(2) INFORMATION FOR SEQ ID NO:19:

```
    (i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO:19:

Xaa Val Leu Asp Leu Phe Arg Glu Leu Leu Asn Glu Gly Leu Glu Ala
 1               5                  10                  15

Leu Lys Gln Lys Leu Lys
            20

(2) INFORMATION FOR SEQ ID NO:20:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

Pro Val Leu Asp Leu Phe Arg Glu Gly Leu Asn Glu Leu Leu Glu Ala
 1               5                  10                  15

Leu Lys Gln Lys Leu Lys
            20

(2) INFORMATION FOR SEQ ID NO:21:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO:21:

Xaa Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:22:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

Pro Val Leu Asp Leu Phe Arg Glu Leu Leu Asn Glu Leu Leu Glu Gly
 1               5                  10                  15
```

Leu Lys Gln Lys Leu Lys
            20

(2) INFORMATION FOR SEQ ID NO:23:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

Pro Leu Leu Glu Leu Phe Lys Glu Leu Leu Gln Glu Leu Leu Glu Ala
1               5                   10                  15
Leu Lys Gln Lys Leu Lys
            20

(2) INFORMATION FOR SEQ ID NO:24:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Pro Val Leu Asp Leu Phe Arg Glu Leu Leu Asn Glu Leu Leu Glu Ala
1               5                   10                  15
Leu Gln Lys Lys Leu Lys
            20

(2) INFORMATION FOR SEQ ID NO:25:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:25:

Pro Val Leu Asp Phe Phe Arg Glu Leu Leu Asn Glu Xaa Leu Glu Ala
1               5                   10                  15
Leu Lys Gln Lys Leu Lys
            20

(2) INFORMATION FOR SEQ ID NO:26:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

```
Pro Val Leu Asp Leu Phe Arg Glu Leu Leu Asn Glu Leu Leu Glu Leu
  1               5                  10                  15

Leu Lys Gln Lys Leu Lys
            20
```

(2) INFORMATION FOR SEQ ID NO:27:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 14
        (D) OTHER INFORMATION: Xaa = Naphthylalanine (xi) SEQUENCE DESCRIPTION: SEQ ID NO:27:

```
Pro Val Leu Asp Leu Phe Arg Glu Leu Leu Asn Glu Leu Xaa Glu Ala
  1               5                  10                  15

Leu Lys Gln Lys Leu Lys
            20
```

(2) INFORMATION FOR SEQ ID NO:28:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

```
Pro Val Leu Asp Leu Phe Arg Glu Leu Leu Asn Glu Leu Trp Glu Ala
  1               5                  10                  15

Leu Lys Gln Lys Leu Lys
            20
```

(2) INFORMATION FOR SEQ ID NO:29:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

```
Ala Val Leu Asp Leu Phe Arg Glu Leu Leu Asn Glu Leu Leu Glu Ala
  1               5                  10                  15

Leu Lys Gln Lys Leu Lys
            20
```

(2) INFORMATION FOR SEQ ID NO:30:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None

```
    (ix) FEATURE:
          (A) NAME/KEY: Other
          (B) LOCATION: 1...22
          (D) OTHER INFORMATION: N-terminal dansylated peptide (xi) SEQUENCE DESCRIPTION: SEQ ID NO:30:

Pro Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:31:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO:31:

Pro Val Leu Asp Leu Phe Leu Glu Leu Leu Asn Glu Xaa Leu Glu Ala
 1               5                  10                  15

Leu Lys Gln Lys Leu Lys
            20

(2) INFORMATION FOR SEQ ID NO:32:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 1
         (D) OTHER INFORMATION: Xaa = Aib (xi) SEQUENCE DESCRIPTION: SEQ ID NO:32:

Xaa Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:33:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: None (xi) SEQUENCE DESCRIPTION: SEQ ID NO:33:

Pro Val Leu Asp Leu Phe Arg Glu Lys Leu Asn Glu Leu Leu Glu Ala
 1               5                  10                  15

Leu Lys Gln Lys Leu Lys
            20
```

(2) INFORMATION FOR SEQ ID NO:34:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 5
        (D) OTHER INFORMATION: Xaa = Naphthylalanine (xi) SEQUENCE DESCRIPTION: SEQ ID NO:34:

Pro Val Leu Asp Xaa Phe Arg Glu Leu Leu Asn Glu Leu Leu Glu Ala
1               5                   10                  15

Leu Lys Gln Lys Leu Lys
            20

(2) INFORMATION FOR SEQ ID NO:35:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

Pro Val Leu Asp Trp Phe Arg Glu Leu Leu Asn Glu Leu Leu Glu Ala
1               5                   10                  15

Leu Lys Gln Lys Leu Lys
            20

(2) INFORMATION FOR SEQ ID NO:36:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

Pro Leu Leu Glu Leu Leu Lys Glu Leu Leu Gln Glu Leu Leu Glu Ala
1               5                   10                  15

Leu Lys Gln Lys Leu Lys
            20

(2) INFORMATION FOR SEQ ID NO:37:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:37:

Pro Val Leu Asp Leu Phe Arg Glu Trp Leu Asn Glu Leu Leu Glu Ala
1               5                   10                  15

```
Leu Lys Gln Lys Leu Lys
            20

(2) INFORMATION FOR SEQ ID NO:38:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:38:

Pro Val Leu Asp Leu Phe Arg Glu Leu Leu Asn Glu Xaa Leu Glu Ala
 1               5                  10                  15

Trp Lys Gln Lys Leu Lys
            20

(2) INFORMATION FOR SEQ ID NO:39:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:39:

Pro Val Leu Asp Leu Phe Arg Glu Leu Leu Glu Glu Leu Leu Lys Ala
 1               5                  10                  15

Leu Lys Lys Lys Leu Lys
            20

(2) INFORMATION FOR SEQ ID NO:40:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:40:

Pro Val Leu Asp Leu Phe Asn Glu Leu Leu Arg Glu Leu Leu Glu Ala
 1               5                  10                  15

Leu Gln Lys Lys Leu Lys
            20

(2) INFORMATION FOR SEQ ID NO:41:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
```

(D) OTHER INFORMATION: Xaa = Aib (xi) SEQUENCE DESCRIPTION: SEQ ID NO:41:

Pro Val Leu Asp Leu Trp Arg Glu Leu Leu Asn Glu Xaa Leu Glu Ala
  1               5                  10                  15

Leu Lys Gln Lys Leu Lys
            20

(2) INFORMATION FOR SEQ ID NO:42:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:42:

Pro Val Leu Asp Glu Phe Arg Glu Lys Leu Asn Glu Xaa Trp Glu Ala
  1               5                  10                  15

Leu Lys Gln Lys Leu Lys
            20

(2) INFORMATION FOR SEQ ID NO:43:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:43:

Pro Val Leu Asp Glu Phe Arg Glu Lys Leu Trp Glu Xaa Leu Glu Ala
  1               5                  10                  15

Leu Lys Gln Lys Leu Lys
            20

(2) INFORMATION FOR SEQ ID NO:44:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All genetically encoded amino acids
            are in the D-configuration
        (A) NAME/KEY: Other
        (B) LOCATION: 13
        (D) OTHER INFORMATION: Xaa = Aib (xi) SEQUENCE DESCRIPTION: SEQ ID NO:44:

```
Pro Val Leu Asp Glu Phe Arg Glu Lys Leu Asn Glu Xaa Leu Glu Ala
 1               5                  10                  15

Leu Lys Gln Lys Leu Lys
             20

(2) INFORMATION FOR SEQ ID NO:45:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:45:

Pro Val Leu Asp Glu Phe Arg Glu Lys Leu Asn Glu Xaa Leu Glu Ala
 1               5                  10                  15

Leu Lys Gln Lys Leu Lys
             20

(2) INFORMATION FOR SEQ ID NO:46:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:46:

Pro Val Leu Asp Leu Phe Arg Glu Lys Leu Asn Glu Xaa Leu Glu Ala
 1               5                  10                  15

Leu Lys Gln Lys Leu Lys
             20

(2) INFORMATION FOR SEQ ID NO:47:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:47:

Val Leu Asp Leu Phe Arg Glu Leu Leu Asn Glu Gly Leu Glu Ala Leu
 1               5                  10                  15

Lys Gln Lys Leu Lys
         20

(2) INFORMATION FOR SEQ ID NO:48:

(i) SEQUENCE CHARACTERISTICS:
        (A) LENGTH: 22 amino acids
```

```
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro
        (A) NAME/KEY: Other
        (B) LOCATION: 2
        (D) OTHER INFORMATION: Xaa = D-Val (xi) SEQUENCE DESCRIPTION: SEQ ID NO:48:

Xaa Xaa Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:49:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:49:

Pro Val Leu Asp Leu Phe Arg Asn Leu Leu Glu Lys Leu Leu Glu Ala
 1               5                  10                  15

Leu Glu Gln Lys Leu Lys
            20

(2) INFORMATION FOR SEQ ID NO:50:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:50:

Pro Val Leu Asp Leu Phe Arg Glu Leu Leu Trp Glu Xaa Leu Glu Ala
 1               5                  10                  15

Leu Lys Gln Lys Leu Lys
            20

(2) INFORMATION FOR SEQ ID NO:51:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
```

(D) OTHER INFORMATION: Xaa = Aib (xi) SEQUENCE DESCRIPTION: SEQ ID NO:51:

Pro Val Leu Asp Leu Phe Trp Glu Leu Leu Asn Glu Xaa Leu Glu Ala
1               5                   10                  15

Leu Lys Gln Lys Leu Lys
            20

(2) INFORMATION FOR SEQ ID NO:52:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:52:

Pro Val Trp Asp Glu Phe Arg Glu Lys Leu Asn Glu Xaa Leu Glu Ala
1               5                   10                  15

Leu Lys Gln Lys Leu Lys
            20

(2) INFORMATION FOR SEQ ID NO:53:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:53:

Val Val Leu Asp Leu Phe Arg Glu Leu Leu Asn Glu Leu Leu Glu Ala
1               5                   10                  15

Leu Lys Gln Lys Leu Lys
            20

(2) INFORMATION FOR SEQ ID NO:54:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:54:

Pro Val Leu Asp Leu Phe Arg Glu Leu Leu Asn Glu Trp Leu Glu Ala
1               5                   10                  15

Leu Lys Gln Lys Leu Lys
            20

(2) INFORMATION FOR SEQ ID NO:55:

(i) SEQUENCE CHARACTERISTICS:
        (A) LENGTH: 19 amino acids
        (B) TYPE: amino acid
        (C) STRANDEDNESS: single

```
        (D) TOPOLOGY: linear (ii) MOLECULE TYPE: None (xi) SEQUENCE DESCRIPTION: SEQ ID NO:55:

Pro Leu Phe Arg Glu Leu Leu Asn Glu Leu Leu Glu Ala Leu Lys Gln
1               5                   10                  15

Lys Leu Lys (2) INFORMATION FOR SEQ ID NO:56:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:56:

Pro Val Leu Asp Leu Phe Arg Glu Leu Leu Asn Glu Leu Leu Glu Ala
1               5                   10                  15

Leu Lys Gln Lys Lys Lys
                20

(2) INFORMATION FOR SEQ ID NO:57:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:57:

Pro Val Leu Asp Leu Phe Arg Asn Leu Leu Glu Glu Leu Leu Lys Ala
1               5                   10                  15

Leu Glu Gln Lys Leu Lys
                20

(2) INFORMATION FOR SEQ ID NO:58:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:58:

Pro Val Leu Asp Glu Phe Arg Glu Lys Leu Asn Glu Xaa Leu Glu Ala
1               5                   10                  15

Leu Lys Gln Lys Leu
                20

(2) INFORMATION FOR SEQ ID NO:59:

(i) SEQUENCE CHARACTERISTICS:
        (A) LENGTH: 22 amino acids
        (B) TYPE: amino acid
```

-continued (C) STRANDEDNESS: single
            (D) TOPOLOGY: linear (ii) MOLECULE TYPE: None (xi) SEQUENCE DESCRIPTION: SEQ ID NO:59:

Leu Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:60:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:60:

Pro Val Leu Asp Leu Phe Arg Glu Leu Leu Asn Glu Leu Leu Glu Ala
 1               5                  10                  15

Leu Lys Gln (2) INFORMATION FOR SEQ ID NO:61:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO:61:

Pro Val Leu Asp Glu Phe Arg Trp Lys Leu Asn Glu Xaa Leu Glu Ala
 1               5                  10                  15

Leu Lys Gln Lys Leu Lys
            20

(2) INFORMATION FOR SEQ ID NO:62:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO:62:

Pro Val Leu Asp Glu Trp Arg Glu Lys Leu Asn Glu Xaa Leu Glu Ala
 1               5                  10                  15

Leu Lys Gln Lys Leu Lys
            20

(2) INFORMATION FOR SEQ ID NO:63:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:63:

Pro Val Leu Asp Phe Phe Arg Glu Lys Leu Asn Glu Xaa Leu Glu Ala
 1               5                  10                  15

Leu Lys Gln Lys Leu Lys
            20

(2) INFORMATION FOR SEQ ID NO:64:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:64:

Pro Trp Leu Asp Glu Phe Arg Glu Lys Leu Asn Glu Xaa Leu Glu Ala
 1               5                  10                  15

Leu Lys Gln Lys Leu Lys
            20

(2) INFORMATION FOR SEQ ID NO:65:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 12
        (D) OTHER INFORMATION: Xaa = Aib (xi) SEQUENCE DESCRIPTION: SEQ ID NO:65:

Val Leu Asp Glu Phe Arg Glu Lys Leu Asn Glu Xaa Leu Glu Ala Leu
 1               5                  10                  15

Lys Gln Lys Leu Lys
            20

(2) INFORMATION FOR SEQ ID NO:66:

(i) SEQUENCE CHARACTERISTICS:
        (A) LENGTH: 22 amino acids
        (B) TYPE: amino acid
        (C) STRANDEDNESS: single -continued (D) TOPOLOGY: linear (ii) MOLECULE TYPE: None (xi) SEQUENCE DESCRIPTION: SEQ ID NO:66:

Pro Val Leu Asp Leu Phe Arg Asn Leu Leu Glu Glu Leu Leu Glu Ala
1               5                   10                  15

Leu Gln Lys Lys Leu Lys
            20

(2) INFORMATION FOR SEQ ID NO:67:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:67:

Val Leu Asp Leu Phe Arg Glu Leu Leu Asn Glu Leu Leu Glu Ala Leu
1               5                   10                  15

Lys Gln Lys Leu Lys
            20

(2) INFORMATION FOR SEQ ID NO:68:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:68:

Pro Val Leu Asp Glu Phe Arg Glu Leu Leu Lys Glu Xaa Leu Glu Ala
1               5                   10                  15

Leu Lys Gln Lys Leu Lys
            20

(2) INFORMATION FOR SEQ ID NO:69:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:69:

Pro Val Leu Asp Glu Phe Arg Lys Lys Leu Asn Glu Xaa Leu Glu Ala
1               5                   10                  15

Leu Lys Gln Lys Leu Lys
            20

(2) INFORMATION FOR SEQ ID NO:70:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:70:

Pro Val Leu Asp Glu Phe Arg Glu Leu Leu Tyr Glu Xaa Leu Glu Ala
  1               5                  10                  15

Leu Lys Gln Lys Leu Lys
            20

(2) INFORMATION FOR SEQ ID NO:71:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 14
        (D) OTHER INFORMATION: Xaa = Aib (xi) SEQUENCE DESCRIPTION: SEQ ID NO:71:

Pro Val Leu Asp Glu Phe Arg Glu Lys Leu Asn Glu Leu Xaa Glu Ala
  1               5                  10                  15

Leu Lys Gln Lys Leu Lys
            20

(2) INFORMATION FOR SEQ ID NO:72:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:72:

Pro Val Leu Asp Leu Phe Arg Glu Leu Leu Asn Glu Xaa Leu Trp Ala
  1               5                  10                  15

Leu Lys Gln Lys Leu Lys
            20

(2) INFORMATION FOR SEQ ID NO:73:

(i) SEQUENCE CHARACTERISTICS:
        (A) LENGTH: 22 amino acids
        (B) TYPE: amino acid
        (C) STRANDEDNESS: single

```
            (D) TOPOLOGY: linear (ii) MOLECULE TYPE: None (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO:73:

Pro Val Leu Asp Glu Phe Trp Glu Lys Leu Asn Glu Xaa Leu Glu Ala
 1               5                  10                  15

Leu Lys Gln Lys Leu Lys
            20

(2) INFORMATION FOR SEQ ID NO:74:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO:74:

Pro Val Leu Asp Lys Phe Arg Glu Lys Leu Asn Glu Xaa Leu Glu Ala
 1               5                  10                  15

Leu Lys Gln Lys Leu Lys
            20

(2) INFORMATION FOR SEQ ID NO:75:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:75:

Pro Val Leu Asp Glu Phe Arg Glu Lys Leu Asn Glu Glu Leu Glu Ala
 1               5                  10                  15

Leu Lys Gln Lys Leu Lys
            20

(2) INFORMATION FOR SEQ ID NO:76:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
         (A) NAME/KEY: Other
         (B) LOCATION: 13
         (D) OTHER INFORMATION: Xaa = Aib (xi) SEQUENCE DESCRIPTION: SEQ ID NO:76:

Pro Val Leu Asp Glu Phe Arg Glu Leu Leu Phe Glu Xaa Leu Glu Ala
```

-continued

```
                1               5              10              15
Leu Lys Gln Lys Leu Lys
                20
```

(2) INFORMATION FOR SEQ ID NO:77:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:77:

```
Pro Val Leu Asp Glu Phe Arg Glu Lys Leu Asn Lys Xaa Leu Glu Ala
1               5                  10                  15
Leu Lys Gln Lys Leu Lys
                20
```

(2) INFORMATION FOR SEQ ID NO:78:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:78:

```
Pro Val Leu Asp Glu Phe Arg Asp Lys Leu Asn Glu Xaa Leu Glu Ala
1               5                  10                  15
Leu Lys Gln Lys Leu Lys
                20
```

(2) INFORMATION FOR SEQ ID NO:79:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:79:

```
Pro Val Leu Asp Glu Phe Arg Glu Leu Leu Asn Glu Leu Leu Glu Ala
1               5                  10                  15
Leu Lys Gln Lys Leu Lys
                20
```

(2) INFORMATION FOR SEQ ID NO:80:

(i) SEQUENCE CHARACTERISTICS:
        (A) LENGTH: 22 amino acids
        (B) TYPE: amino acid
        (C) STRANDEDNESS: single (D) TOPOLOGY: linear (ii) MOLECULE TYPE: None (xi) SEQUENCE DESCRIPTION: SEQ ID NO:80:

Pro Val Leu Asp Leu Phe Glu Arg Leu Leu Asn Glu Leu Leu Glu Ala
 1               5                  10                  15

Leu Gln Lys Lys Leu Lys
            20

(2) INFORMATION FOR SEQ ID NO:81:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:81:

Pro Val Leu Asp Glu Phe Arg Glu Lys Leu Asn Trp Xaa Leu Glu Ala
 1               5                  10                  15

Leu Lys Gln Lys Leu Lys
            20

(2) INFORMATION FOR SEQ ID NO:82:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 11
        (D) OTHER INFORMATION: Xaa = Aib (xi) SEQUENCE DESCRIPTION: SEQ ID NO:82:

Leu Asp Glu Phe Arg Glu Lys Leu Asn Glu Xaa Leu Glu Ala Leu Lys
 1               5                  10                  15

Gln Lys Leu Lys
        20

(2) INFORMATION FOR SEQ ID NO:83:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:83:

Pro Val Leu Asp Glu Phe Arg Glu Lys Leu Asn Glu Xaa Leu Glu Ala

```
         1               5              10              15

Leu Trp Gln Lys Leu Lys
                20

(2) INFORMATION FOR SEQ ID NO:84:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:84:

Pro Val Leu Asp Glu Phe Arg Glu Lys Leu Asn Glu Leu Leu Glu Ala
  1               5                  10                  15

Leu Lys Gln Lys Leu Lys
                20

(2) INFORMATION FOR SEQ ID NO:85:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:85:

Pro Leu Asp Leu Phe Arg Glu Leu Leu Asn Glu Leu Leu Glu Ala Leu
  1               5                  10                  15

Lys Gln Lys Leu Lys
                20

(2) INFORMATION FOR SEQ ID NO:86:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:86:

Pro Val Leu Glu Leu Phe Glu Arg Leu Leu Asp Glu Leu Leu Asn Ala
  1               5                  10                  15

Leu Gln Lys Lys Leu Lys
                20

(2) INFORMATION FOR SEQ ID NO:87:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All amino acids are in the
            D-configuration
```

(xi) SEQUENCE DESCRIPTION: SEQ ID NO:87:

Pro Leu Leu Glu Leu Leu Lys Glu Leu Leu Gln Glu Leu Leu Glu Ala
1               5                  10                  15

Leu Lys Gln Lys Leu Lys
            20

(2) INFORMATION FOR SEQ ID NO:88:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:88:

Pro Val Leu Asp Lys Phe Arg Glu Leu Leu Asn Glu Xaa Leu Glu Ala
1               5                  10                  15

Leu Lys Gln Lys Leu Lys
            20

(2) INFORMATION FOR SEQ ID NO:89:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:89:

Pro Val Leu Asp Glu Phe Arg Glu Lys Leu Asn Glu Xaa Leu Trp Ala
1               5                  10                  15

Leu Lys Gln Lys Leu Lys
            20

(2) INFORMATION FOR SEQ ID NO:90:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 10
        (D) OTHER INFORMATION: Xaa = Aib (xi) SEQUENCE DESCRIPTION: SEQ ID NO:90:

Asp Glu Phe Arg Glu Lys Leu Asn Glu Xaa Leu Glu Ala Leu Lys Gln
1               5                  10                  15

Lys Leu Lys

```
(2) INFORMATION FOR SEQ ID NO:91:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:91:

Pro Val Leu Asp Glu Phe Arg Glu Leu Leu Asn Glu Xaa Leu Glu Ala
 1               5                  10                  15

Leu Lys Gln Lys Leu Lys
            20

(2) INFORMATION FOR SEQ ID NO:92:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:92:

Pro Val Leu Asp Glu Phe Arg Glu Leu Tyr Asn Glu Xaa Leu Glu Ala
 1               5                  10                  15

Leu Lys Gln Lys Leu Lys
            20

(2) INFORMATION FOR SEQ ID NO:93:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:93:

Pro Val Leu Asp Glu Phe Arg Glu Lys Leu Asn Glu Xaa Leu Lys Ala
 1               5                  10                  15

Leu Lys Gln Lys Leu Lys
            20

(2) INFORMATION FOR SEQ ID NO:94:

(i) SEQUENCE CHARACTERISTICS:
        (A) LENGTH: 22 amino acids
        (B) TYPE: amino acid
        (C) STRANDEDNESS: single
```

(D) TOPOLOGY: linear (ii) MOLECULE TYPE: None (xi) SEQUENCE DESCRIPTION: SEQ ID NO:94:

Pro Val Leu Asp Glu Phe Arg Glu Lys Leu Asn Glu Ala Leu Glu Ala
    1               5                   10                  15

Leu Lys Gln Lys Leu Lys
                20

(2) INFORMATION FOR SEQ ID NO:95:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 13
            (D) OTHER INFORMATION: Xaa = Aib (xi) SEQUENCE DESCRIPTION: SEQ ID NO:95:

Pro Val Leu Asp Leu Phe Arg Glu Leu Leu Asn Leu Xaa Leu Glu Ala
    1               5                   10                  15

Leu Lys Gln Lys Leu Lys
                20

(2) INFORMATION FOR SEQ ID NO:96:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...22
            (D) OTHER INFORMATION: All genetically encoded amino acids
                are in the D-configuration
            (A) NAME/KEY: Other
            (B) LOCATION: 13
            (D) OTHER INFORMATION: Xaa = Aib (xi) SEQUENCE DESCRIPTION: SEQ ID NO:96:

Pro Val Leu Asp Leu Phe Arg Glu Leu Leu Asn Glu Xaa Leu Glu Ala
    1               5                   10                  15

Leu Lys Gln Lys Leu Lys
                20

(2) INFORMATION FOR SEQ ID NO:97:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:97:

Pro Val Leu Asp Leu Phe Arg Glu Leu Leu Asn Glu Leu Leu Glu
    1               5                   10                  15

(2) INFORMATION FOR SEQ ID NO:98:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:98:

Pro Val Leu Asp Leu Phe Arg Glu Leu Leu Asn Glu Glu Leu Glu Ala
 1               5                  10                  15

Leu Lys Gln Lys Leu Lys
            20

(2) INFORMATION FOR SEQ ID NO:99:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:99:

Lys Leu Lys Gln Lys Leu Ala Glu Leu Leu Glu Asn Leu Leu Glu Arg
 1               5                  10                  15

Phe Leu Asp Leu Val Pro
            20

(2) INFORMATION FOR SEQ ID NO:100:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All amino acids are in the
            D-configuration (xi) SEQUENCE DESCRIPTION: SEQ ID NO:100:

Pro Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:101:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:101:

Pro Val Leu Asp Leu Phe Arg Glu Leu Leu Asn Trp Xaa Leu Glu Ala
  1               5                   10                  15

Leu Lys Gln Lys Leu Lys
            20

(2) INFORMATION FOR SEQ ID NO:102:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:102:

Pro Val Leu Asp Leu Phe Arg Glu Leu Leu Asn Leu Xaa Leu Glu Ala
  1               5                   10                  15

Leu Lys Glu Lys Leu Lys
            20

(2) INFORMATION FOR SEQ ID NO:103:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:103:

Pro Val Leu Asp Glu Phe Arg Glu Leu Leu Asn Glu Glu Leu Glu Ala
  1               5                   10                  15

Leu Lys Gln Lys Leu Lys
            20

(2) INFORMATION FOR SEQ ID NO:104:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:104:

Pro Leu Leu Asn Glu Leu Leu Glu Ala Leu Lys Gln Lys Leu Lys
  1               5                   10                  15

(2) INFORMATION FOR SEQ ID NO:105:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:105:

Pro Ala Ala Asp Ala Phe Arg Glu Ala Ala Asn Glu Ala Ala Glu Ala
1               5                   10                  15

Ala Lys Gln Lys Ala Lys
            20

(2) INFORMATION FOR SEQ ID NO:106:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:106:

Pro Val Leu Asp Leu Phe Arg Glu Lys Leu Asn Glu Glu Leu Glu Ala
1               5                   10                  15

Leu Lys Gln Lys Leu Lys
            20

(2) INFORMATION FOR SEQ ID NO:107:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: All amino acids are in the
            D-configuration (xi) SEQUENCE DESCRIPTION: SEQ ID NO:107:

Lys Leu Lys Gln Lys Leu Ala Glu Leu Leu Glu Asn Leu Leu Glu Arg
1               5                   10                  15

Phe Leu Asp Leu Val Pro
            20

(2) INFORMATION FOR SEQ ID NO:108:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:108:

Pro Val Leu Asp Leu Phe Arg Trp Leu Leu Asn Glu Xaa Leu Glu Ala
1               5                   10                  15

Leu Lys Gln Lys Leu Lys
            20

(2) INFORMATION FOR SEQ ID NO:109:

```
    (i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:109:

Pro Val Leu Asp Glu Phe Arg Glu Lys Leu Asn Glu Arg Leu Glu Ala
 1               5                  10                  15

Leu Lys Gln Lys Leu Lys
            20

(2) INFORMATION FOR SEQ ID NO:110:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib
        (A) NAME/KEY: Other
        (B) LOCATION: 14
        (D) OTHER INFORMATION: Xaa = Aib (xi) SEQUENCE DESCRIPTION: SEQ ID NO:110:

Pro Val Leu Asp Glu Phe Arg Glu Lys Leu Asn Glu Xaa Xaa Glu Ala
 1               5                  10                  15

Leu Lys Gln Lys Leu Lys
            20

(2) INFORMATION FOR SEQ ID NO:111:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:111:

Pro Val Leu Asp Glu Phe Arg Glu Lys Leu Trp Glu Xaa Trp Glu Ala
 1               5                  10                  15

Leu Lys Gln Lys Leu Lys
            20

(2) INFORMATION FOR SEQ ID NO:112:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
```

```
            (A) NAME/KEY: Other
            (B) LOCATION: 13
            (D) OTHER INFORMATION: Xaa = Aib (xi) SEQUENCE DESCRIPTION: SEQ ID NO:112:

Pro Val Leu Asp Glu Phe Arg Glu Lys Leu Asn Glu Xaa Ser Glu Ala
1               5                   10                  15

Leu Lys Gln Lys Leu Lys
            20

(2) INFORMATION FOR SEQ ID NO:113:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:113:

Pro Val Leu Asp Glu Phe Arg Glu Lys Leu Asn Glu Pro Leu Glu Ala
1               5                   10                  15

Leu Lys Gln Lys Leu Lys
            20

(2) INFORMATION FOR SEQ ID NO:114:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:114:

Pro Val Leu Asp Glu Phe Arg Glu Lys Leu Asn Glu Xaa Met Glu Ala
1               5                   10                  15

Leu Lys Gln Lys Leu Lys
            20

(2) INFORMATION FOR SEQ ID NO:115:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:115:

Pro Lys Leu Asp Glu Phe Arg Glu Lys Leu Asn Glu Xaa Leu Glu Ala
1               5                   10                  15

Leu Lys Gln Lys Leu Lys
            20
```

(2) INFORMATION FOR SEQ ID NO:116:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:116:

Pro His Leu Asp Glu Phe Arg Glu Lys Leu Asn Glu Xaa Leu Glu Ala
 1               5                  10                  15

Leu Lys Gln Lys Leu Lys
            20

(2) INFORMATION FOR SEQ ID NO:117:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:117:

Pro Glu Leu Asp Glu Phe Arg Glu Lys Leu Asn Glu Xaa Leu Glu Ala
 1               5                  10                  15

Leu Lys Gln Lys Leu Lys
            20

(2) INFORMATION FOR SEQ ID NO:118:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 13
        (D) OTHER INFORMATION: Xaa = Aib (xi) SEQUENCE DESCRIPTION: SEQ ID NO:118:

Pro Val Leu Asp Glu Phe Arg Glu Lys Leu Asn Glu Xaa Leu Glu Ala
 1               5                  10                  15

Leu Glu Gln Lys Leu Lys
            20

(2) INFORMATION FOR SEQ ID NO:119:

(i) SEQUENCE CHARACTERISTICS:
        (A) LENGTH: 22 amino acids
        (B) TYPE: amino acid
        (C) STRANDEDNESS: single

```
            (D) TOPOLOGY: linear (ii) MOLECULE TYPE: None (ix) FEATURE:
         (A) NAME/KEY: Other
         (B) LOCATION: 17
         (D) OTHER INFORMATION: Xaa = Aib (xi) SEQUENCE DESCRIPTION: SEQ ID NO:119:

Pro Val Leu Asp Glu Phe Arg Glu Lys Leu Asn Glu Glu Leu Glu Ala
1               5                   10                  15

Xaa Lys Gln Lys Leu Lys
        20

(2) INFORMATION FOR SEQ ID NO:120:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
         (A) NAME/KEY: Other
         (B) LOCATION: 16
         (D) OTHER INFORMATION: Xaa = Aib (xi) SEQUENCE DESCRIPTION: SEQ ID NO:120:

Pro Val Leu Asp Glu Phe Arg Glu Lys Leu Asn Glu Glu Leu Glu Xaa
1               5                   10                  15

Leu Lys Gln Lys Leu Lys
        20

(2) INFORMATION FOR SEQ ID NO:121:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:121:

Pro Val Leu Asp Glu Phe Arg Glu Lys Leu Asn Glu Glu Leu Glu Ala
1               5                   10                  15

Leu Trp Gln Lys Leu Lys
        20

(2) INFORMATION FOR SEQ ID NO:122:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:122:

Pro Val Leu Asp Glu Phe Arg Glu Lys Leu Asn Glu Glu Leu Glu Trp
1               5                   10                  15

Leu Lys Gln Lys Leu Lys
        20
```

(2) INFORMATION FOR SEQ ID NO:123:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:123:

```
Gln Val Leu Asp Leu Phe Arg Glu Leu Leu Asn Glu Leu Leu Glu Ala
 1               5                  10                  15

Leu Lys Gln Lys Leu Lys
            20
```

(2) INFORMATION FOR SEQ ID NO:124:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 18
        (D) OTHER INFORMATION: Xaa = Orn
        (A) NAME/KEY: Other
        (B) LOCATION: 20
        (D) OTHER INFORMATION: Xaa = Orn
        (A) NAME/KEY: Other
        (B) LOCATION: 22
        (D) OTHER INFORMATION: Xaa = Orn (xi) SEQUENCE DESCRIPTION: SEQ ID NO:124:

```
Pro Val Leu Asp Leu Phe Xaa Glu Leu Leu Asn Glu Leu Leu Glu Ala
 1               5                  10                  15

Leu Xaa Gln Xaa Leu Xaa
            20
```

(2) INFORMATION FOR SEQ ID NO:125:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:125:

```
Asn Val Leu Asp Leu Phe Arg Glu Leu Leu Asn Glu Leu Leu Glu Ala
 1               5                  10                  15

Leu Lys Gln Lys Leu Lys
            20
```

(2) INFORMATION FOR SEQ ID NO:126:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:126:

Pro Val Leu Asp Leu Phe Arg Glu Leu Leu Asn Glu Leu Gly Glu Ala
 1               5                  10                  15

Leu Lys Gln Lys Leu Lys
            20

(2) INFORMATION FOR SEQ ID NO:127:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:127:

Pro Val Leu Asp Leu Phe Arg Glu Leu Leu Asn Glu Leu Leu Glu Leu
 1               5                  10                  15

Leu Lys Gln Lys Leu Lys
            20

(2) INFORMATION FOR SEQ ID NO:128:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:128:

Pro Val Leu Asp Leu Phe Arg Glu Leu Leu Asn Glu Leu Leu Glu Phe
 1               5                  10                  15

Leu Lys Gln Lys Leu Lys
            20

(2) INFORMATION FOR SEQ ID NO:129:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:129:

Pro Val Leu Glu Leu Phe Asn Asp Leu Leu Arg Glu Leu Leu Glu Ala
 1               5                  10                  15

Leu Gln Lys Lys Leu Lys
            20

(2) INFORMATION FOR SEQ ID NO:130:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:130:

Pro Val Leu Glu Leu Phe Asn Asp Leu Leu Arg Glu Leu Leu Glu Ala 1               5               10              15

Leu Lys Gln Lys Leu Lys
            20

(2) INFORMATION FOR SEQ ID NO:131:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:131:

Pro Val Leu Glu Leu Phe Lys Glu Leu Leu Asn Glu Leu Leu Asp Ala
1               5               10              15

Leu Arg Gln Lys Leu Lys
            20

(2) INFORMATION FOR SEQ ID NO:132:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:132:

Pro Val Leu Asp Leu Phe Arg Glu Leu Leu Glu Asn Leu Leu Glu Ala
1               5               10              15

Leu Gln Lys Lys Leu Lys
            20

(2) INFORMATION FOR SEQ ID NO:133:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:133:

Pro Val Leu Glu Leu Phe Glu Arg Leu Leu Glu Asp Leu Leu Gln Ala
1               5               10              15

Leu Asn Lys Lys Leu Lys
            20

(2) INFORMATION FOR SEQ ID NO:134:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:134:

Pro Val Leu Glu Leu Phe Glu Arg Leu Leu Glu Asp Leu Leu Lys Ala
1               5               10              15

Leu Asn Gln Lys Leu Lys

20

(2) INFORMATION FOR SEQ ID NO:135:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:135:

Asp Val Leu Asp Leu Phe Arg Glu Leu Leu Asn Glu Leu Leu Glu Ala
 1               5                  10                  15

Leu Lys Gln Lys Leu Lys
            20

(2) INFORMATION FOR SEQ ID NO:136:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:136:

Pro Ala Leu Glu Leu Phe Lys Asp Leu Leu Gln Glu Leu Leu Glu Ala
 1               5                  10                  15

Leu Lys Gln Lys Leu Lys
            20

(2) INFORMATION FOR SEQ ID NO:137:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 17
        (D) OTHER INFORMATION: Xaa = Naphthylalanine (xi) SEQUENCE DESCRIPTION: SEQ ID NO:137:

Pro Val Leu Asp Leu Phe Arg Glu Leu Leu Asn Glu Gly Leu Glu Ala
 1               5                  10                  15

Xaa Lys Gln Lys Leu Lys
            20

(2) INFORMATION FOR SEQ ID NO:138:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:138:

Pro Val Leu Asp Leu Phe Arg Glu Leu Leu Asn Glu Gly Leu Glu Trp
 1               5                  10                  15

```
Leu Lys Gln Lys Leu Lys
          20

(2) INFORMATION FOR SEQ ID NO:139:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:139:

Pro Val Leu Asp Leu Phe Arg Glu Leu Trp Asn Glu Gly Leu Glu Ala
  1               5                  10                  15

Leu Lys Gln Lys Leu Lys
          20

(2) INFORMATION FOR SEQ ID NO:140:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 18
        (D) OTHER INFORMATION: Xaa = Orn
        (A) NAME/KEY: Other
        (B) LOCATION: 20
        (D) OTHER INFORMATION: Xaa = Orn
        (A) NAME/KEY: Other
        (B) LOCATION: 22
        (D) OTHER INFORMATION: Xaa = Orn (xi) SEQUENCE DESCRIPTION: SEQ ID NO:140:

Pro Val Leu Asp Leu Phe Arg Glu Leu Leu Asn Glu Gly Leu Glu Ala
  1               5                  10                  15

Leu Xaa Gln Xaa Leu Xaa
          20

(2) INFORMATION FOR SEQ ID NO:141:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:141:

Pro Val Leu Asp Phe Phe Arg Glu Leu Leu Asn Glu Gly Leu Glu Ala
  1               5                  10                  15

Leu Lys Gln Lys Leu Lys
          20

(2) INFORMATION FOR SEQ ID NO:142:

(i) SEQUENCE CHARACTERISTICS:
        (A) LENGTH: 22 amino acids
        (B) TYPE: amino acid
        (C) STRANDEDNESS: single
```

(D) TOPOLOGY: linear (ii) MOLECULE TYPE: None (xi) SEQUENCE DESCRIPTION: SEQ ID NO:142:

Pro Val Leu Glu Leu Phe Arg Glu Leu Leu Asn Glu Gly Leu Glu Ala
 1               5                   10                  15

Leu Lys Gln Lys Leu Lys
            20

(2) INFORMATION FOR SEQ ID NO:143:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...22
        (D) OTHER INFORMATION: N-terminal acetylated and
            C-terminal amidated peptide (xi) SEQUENCE DESCRIPTION: SEQ ID NO:143:

Pro Val Leu Asp Leu Phe Arg Glu Leu Leu Asn Glu Gly Leu Glu Ala
 1               5                   10                  15

Leu Lys Gln Lys Leu Lys
            20

(2) INFORMATION FOR SEQ ID NO:144:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1
        (D) OTHER INFORMATION: Xaa = D-Pro (xi) SEQUENCE DESCRIPTION: SEQ ID NO:144:

Xaa Val Leu Glu Leu Phe Glu Asn Leu Leu Glu Arg Leu Leu Asp Ala
 1               5                   10                  15

Leu Gln Lys Lys Leu Lys
            20

(2) INFORMATION FOR SEQ ID NO:145:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:145:

Gly Val Leu Glu Leu Phe Glu Asn Leu Leu Glu Arg Leu Leu Asp Ala
 1               5                   10                  15

Leu Gln Lys Lys Leu Lys
            20

(2) INFORMATION FOR SEQ ID NO:146:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:146:

Pro Val Leu Glu Leu Phe Glu Asn Leu Leu Glu Arg Leu Leu Asp Ala
1               5                  10                  15

Leu Gln Lys Lys Leu Lys
            20

(2) INFORMATION FOR SEQ ID NO:147:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:147:

Pro Val Leu Glu Leu Phe Glu Asn Leu Leu Glu Arg Leu Phe Asp Ala
1               5                  10                  15

Leu Gln Lys Lys Leu Lys
            20

(2) INFORMATION FOR SEQ ID NO:148:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:148:

Pro Val Leu Glu Leu Phe Glu Asn Leu Leu Glu Arg Leu Gly Asp Ala
1               5                  10                  15

Leu Gln Lys Lys Leu Lys
            20

(2) INFORMATION FOR SEQ ID NO:149:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:149:

Pro Val Leu Glu Leu Phe Glu Asn Leu Trp Glu Arg Leu Leu Asp Ala
1               5                  10                  15

Leu Gln Lys Lys Leu Lys
            20

(2) INFORMATION FOR SEQ ID NO:150:

```
    (i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:150:

Pro Leu Leu Glu Leu Phe Glu Asn Leu Leu Glu Arg Leu Leu Asp Ala
 1               5                  10                  15

Leu Gln Lys Lys Leu Lys
            20

(2) INFORMATION FOR SEQ ID NO:151:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:151:

Pro Val Leu Glu Leu Phe Glu Asn Leu Gly Glu Arg Leu Leu Asp Ala
 1               5                  10                  15

Leu Gln Lys Lys Leu Lys
            20

(2) INFORMATION FOR SEQ ID NO:152:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:152:

Pro Val Phe Glu Leu Phe Glu Asn Leu Leu Glu Arg Leu Leu Asp Ala
 1               5                  10                  15

Leu Gln Lys Lys Leu Lys
            20

(2) INFORMATION FOR SEQ ID NO:153:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:153:

Ala Val Leu Glu Leu Phe Glu Asn Leu Leu Glu Arg Leu Leu Asp Ala
 1               5                  10                  15

Leu Gln Lys Lys Leu Lys
            20

(2) INFORMATION FOR SEQ ID NO:154:

(i) SEQUENCE CHARACTERISTICS:
        (A) LENGTH: 22 amino acids
```

```
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:154:

Pro Val Leu Glu Leu Phe Glu Asn Leu Leu Glu Arg Gly Leu Asp Ala
 1               5                  10                  15

Leu Gln Lys Lys Leu Lys
            20

(2) INFORMATION FOR SEQ ID NO:155:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:155:

Pro Val Leu Glu Leu Phe Leu Asn Leu Trp Glu Arg Leu Leu Asp Ala
 1               5                  10                  15

Leu Gln Lys Lys Leu Lys
            20

(2) INFORMATION FOR SEQ ID NO:156:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:156:

Pro Val Leu Glu Leu Phe Leu Asn Leu Leu Glu Arg Leu Leu Asp Ala
 1               5                  10                  15

Leu Gln Lys Lys Leu Lys
            20

(2) INFORMATION FOR SEQ ID NO:157:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:157:

Pro Val Leu Glu Phe Phe Glu Asn Leu Leu Glu Arg Leu Leu Asp Ala
 1               5                  10                  15

Leu Gln Lys Lys Leu Lys
            20

(2) INFORMATION FOR SEQ ID NO:158:

(i) SEQUENCE CHARACTERISTICS:
        (A) LENGTH: 22 amino acids
        (B) TYPE: amino acid
        (C) STRANDEDNESS: single
        (D) TOPOLOGY: linear
```

(ii) MOLECULE TYPE: None (xi) SEQUENCE DESCRIPTION: SEQ ID NO:158:

Pro Val Leu Glu Leu Phe Leu Asn Leu Leu Glu Arg Leu Leu Asp Trp
  1               5                  10                  15

Leu Gln Lys Lys Leu Lys
            20

(2) INFORMATION FOR SEQ ID NO:159:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:159:

Pro Val Leu Asp Leu Phe Glu Asn Leu Leu Glu Arg Leu Leu Asp Ala
  1               5                  10                  15

Leu Gln Lys Lys Leu Lys
            20

(2) INFORMATION FOR SEQ ID NO:160:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:160:

Pro Val Leu Glu Leu Phe Glu Asn Leu Leu Glu Arg Leu Leu Asp Trp
  1               5                  10                  15

Leu Gln Lys Lys Leu Lys
            20

(2) INFORMATION FOR SEQ ID NO:161:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:161:

Pro Val Leu Glu Leu Phe Glu Asn Leu Leu Glu Arg Leu Leu Glu Ala
  1               5                  10                  15

Leu Gln Lys Lys Leu Lys
            20

(2) INFORMATION FOR SEQ ID NO:162:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: None (xi) SEQUENCE DESCRIPTION: SEQ ID NO:162:

Pro Val Leu Glu Leu Phe Glu Asn Trp Leu Glu Arg Leu Leu Asp Ala
1               5                   10                  15

Leu Gln Lys Lys Leu Lys
            20

(2) INFORMATION FOR SEQ ID NO:163:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:163:

Pro Val Leu Glu Leu Phe Glu Asn Leu Leu Glu Arg Leu Trp Asp Ala
1               5                   10                  15

Leu Gln Lys Lys Leu Lys
            20

(2) INFORMATION FOR SEQ ID NO:164:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:164:

Pro Val Leu Glu Leu Phe Glu Asn Leu Leu Glu Arg Leu Leu Asp Ala
1               5                   10                  15

Trp Gln Lys Lys Leu Lys
            20

(2) INFORMATION FOR SEQ ID NO:165:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:165:

Pro Val Leu Glu Leu Phe Glu Asn Leu Leu Glu Arg Leu Leu Asp Leu
1               5                   10                  15

Leu Gln Lys Lys Leu Lys
            20

(2) INFORMATION FOR SEQ ID NO:166:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:166:

Pro Val Leu Glu Leu Phe Leu Asn Leu Leu Glu Lys Leu Leu Asp Ala

```
                 1               5              10              15

Leu Gln Lys Lys Leu Lys
                 20

(2) INFORMATION FOR SEQ ID NO:167:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:167:

Pro Val Leu Glu Leu Phe Glu Asn Gly Leu Glu Arg Leu Leu Asp Ala
1               5                  10                  15
Leu Gln Lys Lys Leu Lys
                 20

(2) INFORMATION FOR SEQ ID NO:168:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:168:

Pro Val Leu Glu Leu Phe Glu Gln Leu Leu Glu Lys Leu Leu Asp Ala
1               5                  10                  15
Leu Gln Lys Lys Leu Lys
                 20

(2) INFORMATION FOR SEQ ID NO:169:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:169:

Pro Val Leu Glu Leu Phe Glu Asn Leu Leu Glu Lys Leu Leu Asp Ala
1               5                  10                  15
Leu Gln Lys Lys Leu Lys
                 20

(2) INFORMATION FOR SEQ ID NO:170:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 12
        (D) OTHER INFORMATION: Xaa = Orn
        (A) NAME/KEY: Other
        (B) LOCATION: 19
```

(D) OTHER INFORMATION: Xaa = Orn
            (A) NAME/KEY: Other
            (B) LOCATION: 20
            (D) OTHER INFORMATION: Xaa = Orn
            (A) NAME/KEY: Other
            (B) LOCATION: 22
            (D) OTHER INFORMATION: Xaa = Orn (xi) SEQUENCE DESCRIPTION: SEQ ID NO:170:

Pro Val Leu Glu Leu Phe Glu Asn Leu Leu Glu Xaa Leu Leu Asp Ala
 1               5                  10                  15

Leu Gln Xaa Xaa Leu Xaa
            20

(2) INFORMATION FOR SEQ ID NO:171:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:171:

Pro Val Leu Glu Leu Phe Glu Asn Leu Leu Glu Lys Leu Leu Asp Leu
 1               5                  10                  15

Leu Gln Lys Lys Leu Lys
            20

(2) INFORMATION FOR SEQ ID NO:172:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:172:

Pro Val Leu Glu Leu Phe Leu Asn Leu Leu Glu Arg Leu Gly Asp Ala
 1               5                  10                  15

Leu Gln Lys Lys Leu Lys
            20

(2) INFORMATION FOR SEQ ID NO:173:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:173:

Pro Val Leu Asp Leu Phe Asp Asn Leu Leu Asp Arg Leu Leu Asp Leu
 1               5                  10                  15

Leu Asn Lys Lys Leu Lys
            20

(2) INFORMATION FOR SEQ ID NO:174:

(i) SEQUENCE CHARACTERISTICS:
            (A) LENGTH: 22 amino acids
            (B) TYPE: amino acid (C) STRANDEDNESS: single
            (D) TOPOLOGY: linear (ii) MOLECULE TYPE: None (ix) FEATURE:
            (A) NAME/KEY: Other
            (B) LOCATION: 1...22
            (D) OTHER INFORMATION: All amino acids are in the
                D-configuration (xi) SEQUENCE DESCRIPTION: SEQ ID NO:174:

Pro Val Leu Glu Leu Phe Glu Asn Leu Leu Glu Arg Leu Leu Asp Ala
 1               5                  10                  15

Leu Gln Lys Lys Leu Lys
            20

(2) INFORMATION FOR SEQ ID NO:175:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:175:

Pro Val Leu Glu Leu Phe Glu Asn Leu Leu Glu Arg Leu Leu Glu Leu
 1               5                  10                  15

Leu Asn Lys Lys Leu Lys
            20

(2) INFORMATION FOR SEQ ID NO:176:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:176:

Pro Val Leu Glu Leu Trp Glu Asn Leu Leu Glu Arg Leu Leu Asp Ala
 1               5                  10                  15

Leu Gln Lys Lys Leu Lys
            20

(2) INFORMATION FOR SEQ ID NO:177:

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:177:

Gly Val Leu Glu Leu Phe Leu Asn Leu Leu Glu Arg Leu Leu Asp Ala
 1               5                  10                  15

Leu Gln Lys Lys Leu Lys
            20

(2) INFORMATION FOR SEQ ID NO:178:

```
    (i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:178:

Pro Val Leu Glu Leu Phe Asp Asn Leu Leu Glu Lys Leu Leu Glu Ala
1               5                   10                  15

Leu Gln Lys Lys Leu Arg
            20

(2) INFORMATION FOR SEQ ID NO:179:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:179:

Pro Val Leu Glu Leu Phe Asp Asn Leu Leu Glu Arg Leu Leu Asp Ala
1               5                   10                  15

Leu Gln Lys Lys Leu Lys
            20

(2) INFORMATION FOR SEQ ID NO:180:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:180:

Pro Val Leu Glu Leu Phe Asp Asn Leu Leu Asp Lys Leu Leu Asp Ala
1               5                   10                  15

Leu Gln Lys Lys Leu Arg
            20

(2) INFORMATION FOR SEQ ID NO:181:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:181:

Pro Val Leu Glu Leu Phe Glu Asn Leu Leu Glu Arg Trp Leu Asp Ala
1               5                   10                  15

Leu Gln Lys Lys Leu Lys
            20

(2) INFORMATION FOR SEQ ID NO:182:

(i) SEQUENCE CHARACTERISTICS:
        (A) LENGTH: 22 amino acids
        (B) TYPE: amino acid
```

```
        (C) STRANDEDNESS: single
        (D) TOPOLOGY: linear (ii) MOLECULE TYPE: None (xi) SEQUENCE DESCRIPTION: SEQ ID NO:182:

Pro Val Leu Glu Leu Phe Glu Asn Leu Leu Glu Lys Leu Leu Glu Ala
  1               5                  10                  15

Leu Gln Lys Lys Leu Lys
            20

(2) INFORMATION FOR SEQ ID NO:183:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:183:

Pro Leu Leu Glu Leu Phe Glu Asn Leu Leu Glu Lys Leu Leu Asp Ala
  1               5                  10                  15

Leu Gln Lys Lys Leu Lys
            20

(2) INFORMATION FOR SEQ ID NO:184:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:184:

Pro Val Leu Glu Leu Phe Leu Asn Leu Leu Glu Arg Leu Leu Asp Ala
  1               5                  10                  15

Trp Gln Lys Lys Leu Lys
            20

(2) INFORMATION FOR SEQ ID NO:185:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 19
        (D) OTHER INFORMATION: Xaa = Orn
        (A) NAME/KEY: Other
        (B) LOCATION: 20
        (D) OTHER INFORMATION: Xaa = Orn
        (A) NAME/KEY: Other
        (B) LOCATION: 22
        (D) OTHER INFORMATION: Xaa = Orn (xi) SEQUENCE DESCRIPTION: SEQ ID NO:185:

Pro Val Leu Glu Leu Phe Glu Asn Leu Leu Glu Arg Leu Leu Asp Ala
  1               5                  10                  15

Leu Gln Xaa Xaa Leu Xaa
```

(2) INFORMATION FOR SEQ ID NO:186:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:186:

```
Pro Val Leu Glu Leu Phe Glu Gln Leu Leu Glu Arg Leu Leu Asp Ala
 1               5                  10                  15
Leu Gln Lys Lys Leu Lys
            20
```

(2) INFORMATION FOR SEQ ID NO:187:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:187:

```
Pro Val Leu Glu Leu Phe Glu Asn Leu Leu Glu Arg Leu Leu Asp Ala
 1               5                  10                  15
Leu Asn Lys Lys Leu Lys
            20
```

(2) INFORMATION FOR SEQ ID NO:188:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:188:

```
Pro Val Leu Glu Leu Phe Glu Asn Leu Leu Asp Arg Leu Leu Asp Ala
 1               5                  10                  15
Leu Gln Lys Lys Leu Lys
            20
```

(2) INFORMATION FOR SEQ ID NO:189:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:189:

```
Asp Val Leu Glu Leu Phe Glu Asn Leu Leu Glu Arg Leu Leu Asp Ala
 1               5                  10                  15
Leu Gln Lys Lys Leu Lys
            20
```

```
(2) INFORMATION FOR SEQ ID NO:190:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:190:

Pro Val Leu Glu Phe Trp Asp Asn Leu Leu Asp Lys Leu Leu Asp Ala
 1               5                  10                  15

Leu Gln Lys Lys Leu Arg
            20

(2) INFORMATION FOR SEQ ID NO:191:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:191:

Pro Val Leu Asp Leu Leu Arg Glu Leu Leu Glu Glu Leu Lys Gln Lys
 1               5                  10                  15

Leu Lys (2) INFORMATION FOR SEQ ID NO:192:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:192:

Pro Val Leu Asp Leu Phe Lys Glu Leu Leu Glu Glu Leu Lys Gln Lys
 1               5                  10                  15

Leu Lys (2) INFORMATION FOR SEQ ID NO:193:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
```

```
        (B) LOCATION: 1...18
        (D) OTHER INFORMATION: N-terminal acetylated and
            C-terminal amidated (xi) SEQUENCE DESCRIPTION: SEQ ID NO:193:

Pro Val Leu Asp Leu Phe Arg Glu Leu Leu Glu Glu Leu Lys Gln Lys
 1               5                  10                  15

Leu Lys (2) INFORMATION FOR SEQ ID NO:194:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:194:

Pro Val Leu Glu Leu Phe Arg Glu Leu Leu Glu Glu Leu Lys Gln Lys
 1               5                  10                  15

Leu Lys (2) INFORMATION FOR SEQ ID NO:195:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:195:

Pro Val Leu Glu Leu Phe Lys Glu Leu Leu Glu Glu Leu Lys Gln Lys
 1               5                  10                  15

Leu Lys (2) INFORMATION FOR SEQ ID NO:196:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:196:

Pro Val Leu Asp Leu Phe Arg Glu Leu Leu Glu Glu Leu Lys Asn Lys
```

```
           1               5              10             15
Leu Lys (2) INFORMATION FOR SEQ ID NO:197:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:197:

Pro Leu Leu Asp Leu Phe Arg Glu Leu Leu Glu Glu Leu Lys Gln Lys
 1               5                  10                  15

Leu Lys (2) INFORMATION FOR SEQ ID NO:198:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:198:

Gly Val Leu Asp Leu Phe Arg Glu Leu Leu Glu Glu Leu Lys Gln Lys
 1               5                  10                  15

Leu Lys (2) INFORMATION FOR SEQ ID NO:199:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:199:

Pro Val Leu Asp Leu Phe Arg Glu Leu Trp Glu Glu Leu Lys Gln Lys
 1               5                  10                  15

Leu Lys (2) INFORMATION FOR SEQ ID NO:200:
```

```
    (i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:200:

Asn Val Leu Asp Leu Phe Arg Glu Leu Leu Glu Glu Leu Lys Gln Lys
 1               5                  10                  15

Leu Lys (2) INFORMATION FOR SEQ ID NO:201:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:201:

Pro Leu Leu Asp Leu Phe Lys Glu Leu Leu Glu Glu Leu Lys Gln Lys
 1               5                  10                  15

Leu Lys (2) INFORMATION FOR SEQ ID NO:202:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:202:

Pro Ala Leu Glu Leu Phe Lys Asp Leu Leu Glu Glu Leu Arg Gln Lys
 1               5                  10                  15

Leu Arg (2) INFORMATION FOR SEQ ID NO:203:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None
```

```
        (ix) FEATURE:
              (A) NAME/KEY: Other
              (B) LOCATION: 1...18
              (D) OTHER INFORMATION: N-terminal acetylated and
                  C-terminal amidated (xi) SEQUENCE DESCRIPTION: SEQ ID NO:203:

Ala Val Leu Asp Leu Phe Arg Glu Leu Leu Glu Glu Leu Lys Gln Lys
  1               5                  10                  15

Leu Lys (2) INFORMATION FOR SEQ ID NO:204:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: None (ix) FEATURE:
              (A) NAME/KEY: Other
              (B) LOCATION: 1...18
              (D) OTHER INFORMATION: N-terminal acetylated and
                  C-terminal amidated (xi) SEQUENCE DESCRIPTION: SEQ ID NO:204:

Pro Val Leu Asp Phe Phe Arg Glu Leu Leu Glu Glu Leu Lys Gln Lys
  1               5                  10                  15

Leu Lys (2) INFORMATION FOR SEQ ID NO:205:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: None (ix) FEATURE:
              (A) NAME/KEY: Other
              (B) LOCATION: 1...18
              (D) OTHER INFORMATION: N-terminal acetylated and
                  C-terminal amidated (xi) SEQUENCE DESCRIPTION: SEQ ID NO:205:

Pro Val Leu Asp Leu Phe Arg Glu Trp Leu Glu Glu Leu Lys Gln Lys
  1               5                  10                  15

Leu Lys (2) INFORMATION FOR SEQ ID NO:206:

(i) SEQUENCE CHARACTERISTICS:
              (A) LENGTH: 18 amino acids
              (B) TYPE: amino acid
              (C) STRANDEDNESS: single
              (D) TOPOLOGY: linear (ii) MOLECULE TYPE: None (ix) FEATURE:
              (A) NAME/KEY: Other
              (B) LOCATION: 1...18
              (D) OTHER INFORMATION: N-terminal acetylated and
                  C-terminal amidated
```

(xi) SEQUENCE DESCRIPTION: SEQ ID NO:206:

Pro Leu Leu Glu Leu Leu Lys Glu Leu Leu Glu Glu Leu Lys Gln Lys
 1               5                  10                  15

Leu Lys (2) INFORMATION FOR SEQ ID NO:207:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:207:

Pro Val Leu Glu Leu Leu Lys Glu Leu Leu Glu Glu Leu Lys Gln Lys
 1               5                  10                  15

Leu Lys (2) INFORMATION FOR SEQ ID NO:208:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:208:

Pro Ala Leu Glu Leu Phe Lys Asp Leu Leu Glu Glu Leu Arg Gln Arg
 1               5                  10                  15

Leu Lys (2) INFORMATION FOR SEQ ID NO:209:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:209:

Pro Val Leu Asp Leu Phe Arg Glu Leu Leu Asn Glu Leu Leu Gln Lys
 1               5                  10                  15

Leu Lys (2) INFORMATION FOR SEQ ID NO:210:

(i) SEQUENCE CHARACTERISTICS:
        (A) LENGTH: 18 amino acids
        (B) TYPE: amino acid

```
        (C) STRANDEDNESS: single
        (D) TOPOLOGY: linear (ii) MOLECULE TYPE: None (xi) SEQUENCE DESCRIPTION: SEQ ID NO:210:

Pro Val Leu Asp Leu Phe Arg Glu Leu Leu Glu Glu Leu Lys Gln Lys
 1               5                  10                  15

Leu Lys (2) INFORMATION FOR SEQ ID NO:211:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated
        (A) NAME/KEY: Other
        (B) LOCATION: 14
        (D) OTHER INFORMATION: Xaa = Orn
        (A) NAME/KEY: Other
        (B) LOCATION: 16
        (D) OTHER INFORMATION: Xaa = Orn
        (A) NAME/KEY: Other
        (B) LOCATION: 18
        (D) OTHER INFORMATION: Xaa = Orn (xi) SEQUENCE DESCRIPTION: SEQ ID NO:211:

Pro Val Leu Asp Leu Phe Arg Glu Leu Leu Glu Glu Leu Xaa Gln Xaa
 1               5                  10                  15

Leu Xaa (2) INFORMATION FOR SEQ ID NO:212:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated
        (A) NAME/KEY: Other
        (B) LOCATION: 7
        (D) OTHER INFORMATION: Xaa = Orn
        (A) NAME/KEY: Other
        (B) LOCATION: 14
        (D) OTHER INFORMATION: Xaa = Orn
        (A) NAME/KEY: Other
        (B) LOCATION: 16
        (D) OTHER INFORMATION: Xaa = Orn (xi) SEQUENCE DESCRIPTION: SEQ ID NO:212:

Pro Val Leu Asp Leu Phe Xaa Glu Leu Leu Glu Glu Leu Xaa Gln Xaa
 1               5                  10                  15

Leu Lys
```

-continued (2) INFORMATION FOR SEQ ID NO:213:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:213:

Pro Ala Leu Glu Leu Phe Lys Asp Leu Leu Glu Glu Phe Arg Gln Arg
1               5                   10                  15

Leu Lys (2) INFORMATION FOR SEQ ID NO:214:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated
        (A) NAME/KEY: Other
        (B) LOCATION: 1
        (D) OTHER INFORMATION: D-configuration of Pro (xi) SEQUENCE DESCRIPTION: SEQ ID NO:214:

Pro Val Leu Asp Leu Phe Arg Glu Leu Leu Glu Glu Leu Lys Gln Lys
1               5                   10                  15

Leu Lys (2) INFORMATION FOR SEQ ID NO:215:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:215:

Pro Val Leu Asp Leu Phe Arg Glu Leu Leu Glu Glu Trp Lys Gln Lys
1               5                   10                  15

Leu Lys (2) INFORMATION FOR SEQ ID NO:216:

(i) SEQUENCE CHARACTERISTICS:
        (A) LENGTH: 18 amino acids

```
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:216:

Pro Val Leu Glu Leu Phe Lys Glu Leu Leu Glu Glu Leu Lys Gln Lys
  1               5                  10                  15

Leu Lys (2) INFORMATION FOR SEQ ID NO:217:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:217:

Pro Val Leu Asp Leu Phe Arg Glu Leu Leu Glu Leu Leu Lys Gln Lys
  1               5                  10                  15

Leu Lys (2) INFORMATION FOR SEQ ID NO:218:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:218:

Pro Val Leu Asp Leu Phe Arg Glu Leu Leu Asn Glu Leu Leu Gln Lys
  1               5                  10                  15

Leu Lys (2) INFORMATION FOR SEQ ID NO:219:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:219:

Pro Val Leu Asp Leu Phe Arg Glu Leu Leu Asn Glu Leu Trp Gln Lys
  1               5                  10                  15

Leu Lys (2) INFORMATION FOR SEQ ID NO:220:

(i) SEQUENCE CHARACTERISTICS:
            (A) LENGTH: 18 amino acids
            (B) TYPE: amino acid
```

```
            (C) STRANDEDNESS: single
            (D) TOPOLOGY: linear (ii) MOLECULE TYPE: None (xi) SEQUENCE DESCRIPTION: SEQ ID NO:220:

Pro Val Leu Asp Leu Phe Arg Glu Leu Leu Glu Glu Leu Gln Lys Lys
 1               5                  10                  15

Leu Lys (2) INFORMATION FOR SEQ ID NO:221:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:221:

Asp Val Leu Asp Leu Phe Arg Glu Leu Leu Glu Glu Leu Lys Gln Lys
 1               5                  10                  15

Leu Lys (2) INFORMATION FOR SEQ ID NO:222:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:222:

Pro Val Leu Asp Ala Phe Arg Glu Leu Leu Glu Ala Leu Leu Gln Leu
 1               5                  10                  15

Lys Lys (2) INFORMATION FOR SEQ ID NO:223:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:223:

Pro Val Leu Asp Ala Phe Arg Glu Leu Leu Glu Ala Leu Ala Gln Leu
 1               5                  10                  15

Lys Lys (2) INFORMATION FOR SEQ ID NO:224:

(i) SEQUENCE CHARACTERISTICS:
            (A) LENGTH: 18 amino acids
            (B) TYPE: amino acid
            (C) STRANDEDNESS: single
```

```
            (D) TOPOLOGY: linear (ii) MOLECULE TYPE: None (xi) SEQUENCE DESCRIPTION: SEQ ID NO:224:

Pro Val Leu Asp Leu Phe Arg Glu Gly Trp Glu Glu Leu Lys Gln Lys
  1               5                  10                  15

Leu Lys (2) INFORMATION FOR SEQ ID NO:225:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:225:

Pro Val Leu Asp Ala Phe Arg Glu Leu Ala Glu Ala Leu Ala Gln Leu
  1               5                  10                  15

Lys Lys (2) INFORMATION FOR SEQ ID NO:226:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:226:

Pro Val Leu Asp Ala Phe Arg Glu Leu Gly Glu Ala Leu Leu Gln Leu
  1               5                  10                  15

Lys Lys (2) INFORMATION FOR SEQ ID NO:227:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:227:

Pro Val Leu Asp Leu Phe Arg Glu Leu Gly Glu Glu Leu Lys Gln Lys
  1               5                  10                  15

Leu Lys (2) INFORMATION FOR SEQ ID NO:228:

(i) SEQUENCE CHARACTERISTICS:
        (A) LENGTH: 18 amino acids
        (B) TYPE: amino acid
        (C) STRANDEDNESS: single
        (D) TOPOLOGY: linear
```

(ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:228:

Pro Val Leu Asp Leu Phe Arg Glu Gly Leu Glu Glu Leu Lys Gln Lys
 1               5                  10                  15

Leu Lys (2) INFORMATION FOR SEQ ID NO:229:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:229:

Pro Val Leu Asp Leu Phe Arg Glu Leu Leu Glu Glu Gly Lys Gln Lys
 1               5                  10                  15

Leu Lys (2) INFORMATION FOR SEQ ID NO:230:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:230:

Pro Val Leu Glu Leu Phe Glu Arg Leu Leu Glu Asp Leu Gln Lys Lys
 1               5                  10                  15

Leu Lys (2) INFORMATION FOR SEQ ID NO:231:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:231:

Pro Val Leu Asp Leu Phe Arg Glu Leu Leu Glu Lys Leu Glu Gln Lys
 1               5                  10                  15

Leu Lys (2) INFORMATION FOR SEQ ID NO:232:

```
    (i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:232:

Pro Leu Leu Glu Leu Phe Lys Glu Leu Leu Glu Glu Leu Lys Gln Lys
 1               5                  10                  15

Leu Lys (2) INFORMATION FOR SEQ ID NO:233:

(i) SEQUENCE CHARACTERISTICS:

(xi) SEQUENCE DESCRIPTION: SEQ ID NO:233:

This sequence has been intentionally skipped (2) INFORMATION FOR SEQ ID NO:234:

(i) SEQUENCE CHARACTERISTICS:

(xi) SEQUENCE DESCRIPTION: SEQ ID NO:234:

This sequence has been intentionally skipped (2) INFORMATION FOR SEQ ID NO:235:

(i) SEQUENCE CHARACTERISTICS:

(xi) SEQUENCE DESCRIPTION: SEQ ID NO:235:

This sequence has been intentionally skipped (2) INFORMATION FOR SEQ ID NO:236:

(i) SEQUENCE CHARACTERISTICS:

(xi) SEQUENCE DESCRIPTION: SEQ ID NO:236:

This sequence has been intentionally skipped (2) INFORMATION FOR SEQ ID NO:237:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:237:

Leu Asp Asp Leu Leu Gln Lys Trp Ala Glu Ala Phe Asn Gln Leu Leu
 1               5                  10                  15

Lys Lys (2) INFORMATION FOR SEQ ID NO:238:

(i) SEQUENCE CHARACTERISTICS:
```

```
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:238:

Glu Trp Leu Lys Ala Phe Tyr Glu Lys Val Leu Glu Lys Leu Lys Glu
 1               5                  10                  15

Leu Phe (2) INFORMATION FOR SEQ ID NO:239:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:239:

Glu Trp Leu Glu Ala Phe Tyr Lys Lys Val Leu Glu Lys Leu Lys Glu
 1               5                  10                  15

Leu Phe (2) INFORMATION FOR SEQ ID NO:240:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None (ix) FEATURE:
            (A) NAME/KEY: Other
            (B) LOCATION: 1...18
            (D) OTHER INFORMATION: N-terminal acetylated and
                C-terminal amidated (xi) SEQUENCE DESCRIPTION: SEQ ID NO:240:

Asp Trp Leu Lys Ala Phe Tyr Asp Lys Val Ala Glu Lys Leu Lys Glu
 1               5                  10                  15

Ala Phe (2) INFORMATION FOR SEQ ID NO:241:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: None
```

```
    (xi) SEQUENCE DESCRIPTION: SEQ ID NO:241:

Asp Trp Phe Lys Ala Phe Tyr Asp Lys Val Phe Glu Lys Phe Lys Glu
1               5                  10                  15

Phe Phe (2) INFORMATION FOR SEQ ID NO:242:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:242:

Gly Ile Lys Lys Phe Leu Gly Ser Ile Trp Lys Phe Ile Lys Ala Phe
1               5                  10                  15

Val Gly (2) INFORMATION FOR SEQ ID NO:243:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:243:

Asp Trp Phe Lys Ala Phe Tyr Asp Lys Val Ala Glu Lys Phe Lys Glu
1               5                  10                  15

Ala Phe (2) INFORMATION FOR SEQ ID NO:244:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:244:

Asp Trp Leu Lys Ala Phe Tyr Asp Lys Val Ala Glu Lys Leu Lys Glu
1               5                  10                  15

Ala Phe (2) INFORMATION FOR SEQ ID NO:245:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:245:

Asp Trp Leu Lys Ala Phe Tyr Asp Lys Val Phe Glu Lys Phe Lys Glu
1               5                  10                  15

Phe Phe
```

(2) INFORMATION FOR SEQ ID NO:246:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:246:

Glu Trp Leu Glu Ala Phe Tyr Lys Lys Val Leu Glu Lys Leu Lys Glu
 1               5                  10                  15

Leu Phe (2) INFORMATION FOR SEQ ID NO:247:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:247:

Asp Trp Phe Lys Ala Phe Tyr Asp Lys Phe Phe Glu Lys Phe Lys Glu
 1               5                  10                  15

Phe Phe (2) INFORMATION FOR SEQ ID NO:248:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:248:

Glu Trp Leu Lys Ala Phe Tyr Glu Lys Val Leu Glu Lys Leu Lys Glu
 1               5                  10                  15

Leu Phe (2) INFORMATION FOR SEQ ID NO:249:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:249:

Glu Trp Leu Lys Ala Glu Tyr Glu Lys Val Glu Glu Lys Leu Lys Glu
 1               5                  10                  15

Leu Phe (2) INFORMATION FOR SEQ ID NO:250:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:250:

Glu Trp Leu Lys Ala Glu Tyr Glu Lys Val Leu Glu Lys Leu Lys Glu
 1               5                  10                  15

Leu Phe (2) INFORMATION FOR SEQ ID NO:251:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...18
        (D) OTHER INFORMATION: N-terminal acetylated and
            C-terminal amidated (xi) SEQUENCE DESCRIPTION: SEQ ID NO:251:

Glu Trp Leu Lys Ala Phe Tyr Lys Lys Val Leu Glu Lys Leu Lys Glu
 1               5                  10                  15

Leu Phe (2) INFORMATION FOR SEQ ID NO:252:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...15
        (D) OTHER INFORMATION: N-terminal acetylated and
            C-terminal amidated (xi) SEQUENCE DESCRIPTION: SEQ ID NO:252:

Pro Val Leu Asp Leu Phe Arg Glu Leu Leu Glu Gln Lys Leu Lys
 1               5                  10                  15

(2) INFORMATION FOR SEQ ID NO:253:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None

```
    (ix) FEATURE:
         (A) NAME/KEY: Other
         (B) LOCATION: 1...16
         (D) OTHER INFORMATION: N-terminal acetylated and
             C-terminal amidated (xi) SEQUENCE DESCRIPTION: SEQ ID NO:253:

Pro Val Leu Asp Leu Phe Arg Glu Leu Leu Glu Glu Leu Lys Gln Lys
1               5                  10                  15

(2) INFORMATION FOR SEQ ID NO:254:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 1...16
         (D) OTHER INFORMATION: N-terminal acetylated and
             C-terminal amidated (xi) SEQUENCE DESCRIPTION: SEQ ID NO:254:

Pro Val Leu Asp Leu Phe Arg Glu Leu Leu Glu Lys Leu Lys Gln Lys
1               5                  10                  15

(2) INFORMATION FOR SEQ ID NO:255:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 1...15
         (D) OTHER INFORMATION: N-terminal acetylated and
             C-terminal amidated (xi) SEQUENCE DESCRIPTION: SEQ ID NO:255:

Pro Val Leu Asp Leu Phe Arg Glu Leu Leu Glu Lys Leu Gln Lys
1               5                  10                  15

(2) INFORMATION FOR SEQ ID NO:256:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: None (ix) FEATURE:
         (A) NAME/KEY: Other
         (B) LOCATION: 1...16
         (D) OTHER INFORMATION: N-terminal acetylated and
             C-terminal amidated (xi) SEQUENCE DESCRIPTION: SEQ ID NO:256:

Pro Val Leu Asp Leu Phe Arg Glu Leu Leu Glu Ala Leu Lys Gln Lys
1               5                  10                  15
```

(2) INFORMATION FOR SEQ ID NO:257:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...16
        (D) OTHER INFORMATION: N-terminal acetylated and
            C-terminal amidated (xi) SEQUENCE DESCRIPTION: SEQ ID NO:257:

```
Pro Val Leu Asp Leu Phe Glu Asn Leu Leu Glu Arg Leu Lys Gln Lys
1               5                   10                  15
```

(2) INFORMATION FOR SEQ ID NO:258:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...16
        (D) OTHER INFORMATION: N-terminal acetylated and
            C-terminal amidated (xi) SEQUENCE DESCRIPTION: SEQ ID NO:258:

```
Pro Val Leu Asp Leu Phe Arg Glu Leu Leu Asn Glu Leu Lys Gln Lys
1               5                   10                  15
```

(2) INFORMATION FOR SEQ ID NO:259:

(i) SEQUENCE CHARACTERISTICS:
        (A) LENGTH: 842 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...801
        (D) OTHER INFORMATION:

(xi) SEQUENCE DESCRIPTION: SEQ ID NO:259:

```
ATG AAA GCT GCG GTG CTG ACC TTG GCC GTG CTC TTC CTG ACG GGG AGC     48
Met Lys Ala Ala Val Leu Thr Leu Ala Val Leu Phe Leu Thr Gly Ser
1               5                   10                  15

CAG GCT CGG CAT TTC TGG CAG CAA GAT GAA CCC CCC CAG AGC CCC TGG     96
Gln Ala Arg His Phe Trp Gln Gln Asp Glu Pro Pro Gln Ser Pro Trp
                20                  25                  30

GAT CGA GTG AAG GAC CTG GCC ACT GTG TAC GTG GAT GTG CTC AAA GAC    144
Asp Arg Val Lys Asp Leu Ala Thr Val Tyr Val Asp Val Leu Lys Asp
            35                  40                  45

AGC GGC AGA GAC TAT GTG TCC CAG TTT GAA GGC TCC GCC TTG GGA AAA    192
Ser Gly Arg Asp Tyr Val Ser Gln Phe Glu Gly Ser Ala Leu Gly Lys
        50                  55                  60

CAG CTA AAC CTA AAG CTC CTT GAC AAC TGG GAC AGC GTG ACC TCC ACC    240
Gln Leu Asn Leu Lys Leu Leu Asp Asn Trp Asp Ser Val Thr Ser Thr
65                  70                  75                  80
```

```
TTC AGC AAG CTG CGC GAA CAG CTC GGC CCT GTG ACC CAG GAG TTC TGG      288
Phe Ser Lys Leu Arg Glu Gln Leu Gly Pro Val Thr Gln Glu Phe Trp
            85                  90                  95

GAT AAC CTG GAA AAG GAG ACA GAG GGC CTG AGG CAG GAG ATG AGC AAG      336
Asp Asn Leu Glu Lys Glu Thr Glu Gly Leu Arg Gln Glu Met Ser Lys
                100                 105                 110

GAT CTG GAG GAG GTG AAG GCC AAG GTG CAG CCC TAC CTG GAC GAC TTC      384
Asp Leu Glu Glu Val Lys Ala Lys Val Gln Pro Tyr Leu Asp Asp Phe
        115                 120                 125

CAG AAG AAG TGG CAG GAG GAG ATG GAG CTC TAC CGC CAG AAG GTG GAG      432
Gln Lys Lys Trp Gln Glu Glu Met Glu Leu Tyr Arg Gln Lys Val Glu
    130                 135                 140

CCG CTG CGC GCA GAG CTC CAA GAG GGC GCG CGC CAG AAG CTG CAC GAG      480
Pro Leu Arg Ala Glu Leu Gln Glu Gly Ala Arg Gln Lys Leu His Glu
145                 150                 155                 160

CTG CAA GAG AAG CTG AGC CCA CTG GGC GAG GAG ATG CGC GAC CGC GCG      528
Leu Gln Glu Lys Leu Ser Pro Leu Gly Glu Glu Met Arg Asp Arg Ala
                165                 170                 175

CGC GCC CAT GTG GAC GCG CTG CGC ACG CAT CTG GCC CCC TAC AGC GAC      576
Arg Ala His Val Asp Ala Leu Arg Thr His Leu Ala Pro Tyr Ser Asp
            180                 185                 190

GAG CTG CGC CAG CGC TTG GCC GCG CGC CTT GAG GCT CTC AAG GAG AAC      624
Glu Leu Arg Gln Arg Leu Ala Ala Arg Leu Glu Ala Leu Lys Glu Asn
        195                 200                 205

GGC GGC GCC AGA CTG GCC GAG TAC CAC GCC AAG GCC ACC GAG CAT CTG      672
Gly Gly Ala Arg Leu Ala Glu Tyr His Ala Lys Ala Thr Glu His Leu
    210                 215                 220

AGC ACG CTC AGC GAG AAG GCC AAG CCC GCG CTC GAG GAC CTC CGC CAA      720
Ser Thr Leu Ser Glu Lys Ala Lys Pro Ala Leu Glu Asp Leu Arg Gln
225                 230                 235                 240

GGC CTG CTG CCC GTG CTG GAG AGC TTC AAG GTC AGC TTC CTG AGC GCT      768
Gly Leu Leu Pro Val Leu Glu Ser Phe Lys Val Ser Phe Leu Ser Ala
                245                 250                 255

CTC GAG GAG TAC ACT AAG AAG CTC AAC ACC CAG TGAGGCGCCC GCCGCCGCCC    821
Leu Glu Glu Tyr Thr Lys Lys Leu Asn Thr Gln
            260                 265

CCCTTCCCGG TGCTCAGAAT A                                              842
```

(2) INFORMATION FOR SEQ ID NO:260:

(i) SEQUENCE CHARACTERISTICS:
        (A) LENGTH: 267 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:260:

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80
```

```
Phe Ser Lys Leu Arg Glu Gln Leu Gly Pro Val Thr Gln Glu Phe Trp
            85                  90                  95
Asp Asn Leu Glu Lys Glu Thr Glu Gly Leu Arg Gln Glu Met Ser Lys
               100                 105                 110
Asp Leu Glu Glu Val Lys Ala Lys Val Gln Pro Tyr Leu Asp Asp Phe
           115                 120                 125
Gln Lys Lys Trp Gln Glu Glu Met Glu Leu Tyr Arg Gln Lys Val Glu
       130                 135                 140
Pro Leu Arg Ala Glu Leu Gln Glu Gly Ala Arg Gln Lys Leu His Glu
145                 150                 155                 160
Leu Gln Glu Lys Leu Ser Pro Leu Gly Glu Glu Met Arg Asp Arg Ala
               165                 170                 175
Arg Ala His Val Asp Ala Leu Arg Thr His Leu Ala Pro Tyr Ser Asp
           180                 185                 190
Glu Leu Arg Gln Arg Leu Ala Ala Arg Leu Glu Ala Leu Lys Glu Asn
       195                 200                 205
Gly Gly Ala Arg Leu Ala Glu Tyr His Ala Lys Ala Thr Glu His Leu
   210                 215                 220
Ser Thr Leu Ser Glu Lys Ala Lys Pro Ala Leu Glu Asp Leu Arg Gln
225                 230                 235                 240
Gly Leu Leu Pro Val Leu Glu Ser Phe Lys Val Ser Phe Leu Ser Ala
               245                 250                 255
Leu Glu Glu Tyr Thr Lys Lys Leu Asn Thr Gln
           260                 265

(2) INFORMATION FOR SEQ ID NO:261:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:261:

CCTGTTCTTG ACCTCTTCCG TGAACTTCTT AACGAAGGCC TCGAGGCACT GAAACAGAAA      60

CTAAAA                                                                66

(2) INFORMATION FOR SEQ ID NO:262:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO:262:

GGTGTTCTGG ACCTCTTCCG TGAACTTCTT AACGAAGGCC TAGCGCTAAA ACAAAAACTA      60

AAA                                                                   63

(2) INFORMATION FOR SEQ ID NO:263:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:263:

CCCGTGTTGG ACTTGTTCCG AGAACTACTA AACGAAGGAC TAGAATGGTT GAAACTAAAA      60
```

CTAAAA  66

(2) INFORMATION FOR SEQ ID NO:264:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:264:

GGTGTTTTGG AACTTTTCGA AAACTTATTG GAAAGATTGT TGGACGCACT GCAAAAAAAA  60

TTGAAA  66

(2) INFORMATION FOR SEQ ID NO:265:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:265:

CCAGTCTTGG AACTTTTCGA GAACTTGTGG GAGCGATTGT TGGATGCTTT GCAAAAAAAA  60

TTGAAA  66

(2) INFORMATION FOR SEQ ID NO:266:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:266:

GCCGTGTTGG AGCTGTTCGA AAACTTATTA GAGCGATTAT TAGACGCATT ACAGAAAAAA  60

TTGAAA  66

(2) INFORMATION FOR SEQ ID NO:267:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:267:

CCTGTGTTGG ACTTGTTCCG CGAGTTATTA AACGAGTTAT TACAGAAATT AAAA  54

(2) INFORMATION FOR SEQ ID NO:268:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:268:

CCTGTGTTGG ACTTGTTGCG AGAATTATTA GAGGAATTAA AACAAAAACT AAAA  54

(2) INFORMATION FOR SEQ ID NO:269:

(i) SEQUENCE CHARACTERISTICS:
        (A) LENGTH: 54 base pairs (B) TYPE: nucleic acid
        (C) STRANDEDNESS: single
        (D) TOPOLOGY: linear (xi) SEQUENCE DESCRIPTION: SEQ ID NO:269:

CCATTATTAG AATTATTTAA GGAATTATTG GAGGAGCTGG AACAGGAACT AGAA            54

(2) INFORMATION FOR SEQ ID NO:270:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:270:

Met Lys Ala Ala Val Leu Thr Leu Ala Val Leu Phe Leu Thr Gly Ser
 1               5                  10                  15

Gln Ala (2) INFORMATION FOR SEQ ID NO:271:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:271:

Met Lys Ala Ala Val Leu Ala Val Ala Leu Val Phe Leu Thr Gly Cys
 1               5                  10                  15

Gln Ala (2) INFORMATION FOR SEQ ID NO:272:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:272:

Arg His Phe Trp Gln Gln
 1               5

(2) INFORMATION FOR SEQ ID NO:273:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:273:

Xaa Glu Phe Xaa Gln Gln
 1               5

(2) INFORMATION FOR SEQ ID NO:274:

-continued (i) SEQUENCE CHARACTERISTICS:
    (A) LENGTH: 16 base pairs
    (B) TYPE: nucleic acid
    (C) STRANDEDNESS: single
    (D) TOPOLOGY: linear (xi) SEQUENCE DESCRIPTION: SEQ ID NO:274:

TGAACCCTTG ACCCCT                                                         16

GENE THERAPY APPROACHES TO SUPPLY APOLIPOPROTEIN A-I AGONISTS AND THEIR USE TO TREAT DYSLIPIDEMIC DISORDERS

CROSS-REFERENCE TO RELATED APPLICATIONS

This application is a continuation of application U.S. Ser. No. 10/283,599, filed on Oct. 29, 2002 now U.S. Pat. No. 6,844,327, which is a continuation of U.S. Ser. No. 08/940,136, filed on Sep. 29, 1997, now U.S. Pat. No. 6,518,412, which are each incorporated herein by reference in their entirety.

1. INTRODUCTION

The invention relates to gene therapy approaches to supply nucleotide sequences encoding modified forms of the native forms of apolipoprotein A-I (ApoA-I) i.e., mature ApoA-I, preproApoA-I and proApoA-I; ApoA-I peptides; ApoA-I agonists and superagonists, peptides which mimic or exceed the activity of native ApoA-I; and the native ApoA-I gene for the treatment of disorders associated with dyslipoproteinemia, including cardiovascular disease, atherosclerosis, restenosis, hyperlipidemia, and other disorders such as septic shock.

2. BACKGROUND OF THE INVENTION

Circulating cholesterol is carried by plasma lipoproteins—particles of complex lipid and protein composition that transport lipids in the blood. Low density lipoproteins (LDL), and high density lipoproteins (HDL) are the major cholesterol carriers. LDL are believed to be responsible for the delivery of cholesterol from the liver (where it is synthesized or obtained from dietary sources) to extrahepatic tissues in the body. The term "reverse cholesterol transport" describes the transport of cholesterol from extrahepatic tissues to the liver where it is catabolized and eliminated. It is believed that plasma HDL particles play a major role in the reverse transport process, acting as scavengers of tissue cholesterol.

The evidence linking elevated serum cholesterol to coronary heart disease is overwhelming. For example, atherosclerosis is a slowly progressive disease characterized by the accumulation of cholesterol within the arterial wall. Compelling evidence supports the concept that lipids deposited in atherosclerotic lesions are derived primarily from plasma LDL; thus, LDLs have popularly become known as the "bad" cholesterol. In contrast, HDL serum levels correlate inversely with coronary heart disease—indeed, high serum levels of HDL are regarded as a negative risk factor. It is hypothesized that high levels of plasma HDL are not only protective against coronary artery disease, but may actually induce regression of atherosclerotic plaques (e.g., see Badimon et al., 1992, Circulation 86 (Suppl. III):86–94). Thus, HDL have popularly become known as the "good" cholesterol.

2.1. Cholesterol Transport

The fat-transport system can be divided into two pathways: an exogenous one for cholesterol and triglycerides absorbed from the intestine, and an endogenous one for cholesterol and triglycerides entering the bloodstream from the liver and other non-hepatic tissue.

In the exogenous pathway, dietary fats are packaged into lipoprotein particles called chylomicrons which enter the bloodstream and deliver their triglycerides to adipose tissue (for storage) and to muscle (for oxidation to supply energy). The remnant of the chylomicron, containing cholesteryl esters, is removed from the circulation by a specific receptor found only on liver cells. This cholesterol then becomes available again for cellular metabolism or for recycling to extrahepatic tissues as plasma lipoproteins.

In the endogenous pathway, the liver secretes a large, very-low-density lipoprotein particle (VLDL) into the bloodstream. The core of VLDLs consists mostly of triglycerides synthesized in the liver, with a smaller amount of cholesteryl esters (either synthesized in the liver or recycled from chylomicrons). Two predominant proteins are displayed on the surface of VLDLs, apoprotein B-100 and apoprotein E. When a VLDL reaches the capillaries of adipose tissue or of muscle, its triglycerides are extracted resulting in a new kind of particle, decreased in size and enriched in cholesteryl esters but retaining its two apoproteins, called intermediate-density lipoprotein (IDL).

In human beings, about half of the IDL particles are removed from the circulation quickly (within two to six hours of their formation), because they bind tightly to liver cells which extract their cholesterol to make new VLDL and bile acids. The IDL particles which are not taken up by the liver remain in the circulation longer. In time, the apoprotein E dissociates from the circulating particles, converting them to LDL having apoprotein B-100 as their sole protein.

Primarily, the liver takes up and degrades most of the cholesterol to bile acids, which are the end products of cholesterol metabolism. The uptake of cholesterol containing particles is mediated by LDL receptors, which are present in high concentrations on hepatocytes. The LDL receptor binds both apoprotein E and apoprotein B-100, and is responsible for binding and removing both IDLs and LDLs from the circulation. However, the affinity of apoprotein E for the LDL receptor is greater than that of apoprotein B-100. As a result, the LDL particles have a much longer circulating life span than IDL particles—LDLs circulate for an average of two and a half days before binding to the LDL receptors in the liver and other tissues. High serum levels of LDL (the "bad" cholesterol) are positively associated with coronary heart disease. For example, in atherosclerosis, cholesterol derived from circulating LDLs accumulates in the walls of arteries leading to the formation of bulky plaques that inhibit the flow of blood until a clot eventually forms, obstructing the artery causing a heart attack or stroke.

Ultimately, the amount of intracellular cholesterol liberated from the LDLs controls cellular cholesterol metabolism. The accumulation of cellular cholesterol derived from VLDLs and LDLs controls three processes: first, it reduces the cell's ability to make its own cholesterol by turning off the synthesis of HMGCOA reductase—a key enzyme in the cholesterol biosynthetic pathway. Second, the incoming LDL-derived cholesterol promotes storage of cholesterol by activating ACAT—the cellular enzyme which converts cholesterol into cholesteryl esters that are deposited in storage droplets. Third, the accumulation of cholesterol within the cell drives a feedback mechanism that inhibits cellular synthesis of new LDL receptors. Cells, therefore, adjust their complement of LDL receptors so that enough cholesterol is brought in to meet their metabolic needs, without overloading. (For a review, see Brown & Goldstein, In, The Pharmacological Basis Of Therapeutics, 8th Ed., Goodman & Gilman, Pergamon Press, NY, 1990, Ch. 36, pp. 874–896).

2.2. Reverse Cholesterol Transport

In sum, peripheral (non-hepatic) cells obtain their cholesterol from a combination of local synthesis and the uptake of preformed sterol from VLDLs and LDLs. In contrast, reverse cholesterol transport (RCT) is the pathway by which peripheral cell cholesterol can be returned to the liver for recycling to extrahepatic tissues, or excretion into the intestine in bile. The RCT pathway represents the only means of eliminating cholesterol from most extrahepatic tissues, and is crucial to maintenance of the structure and function of most cells in the body.

The RCT consists mainly of three steps: (a) cholesterol efflux, the initial removal of cholesterol from various pools of peripheral cells; (b) cholesterol esterification by the action of lecithin:cholesterol acyltransferase (LCAT), preventing a re-entry of effluxed cholesterol into cells; and (c) uptake/delivery of HDL cholesteryl ester to liver cells. The RCT pathway is mediated by HDLS. HDL is a generic term for lipoprotein particles which are characterized by their high density. The main lipidic constituents of HDL complexes are various phospholipids, cholesterol (ester) and triglycerides. The most prominent apolipoprotein components are A-I and A-II which determine the functional characteristics of HDL; furthermore minor amounts of apolipoproteins C-I, C-II, C-III, D, E, J, etc. have been observed. HDL can exist in a wide variety of different sizes and different mixtures of the above-mentioned constituents dependent on the status of remodeling during the metabolic RCT cascade.

The key enzyme involved in the RCT pathway is LCAT. LCAT is produced mainly in the liver and circulates in plasma associated with the HDL fraction. Cholesteryl ester transfer protein (CETP) and another lipid transfer protein, phospholipid transfer protein (PLTP) contribute to further remodeling the circulating HDL population. CETP can move cholesteryl esters made by LCAT to other lipoproteins, particularly ApoB-containing lipoproteins, such as VLDL. HDL triglycerides can be catabolized by the extracellular hepatic triglyceride lipase, and lipoprotein cholesterol is removed by the liver via several mechanisms.

Each HDL particle contains at least one copy (and usually two to four copies) of ApoA-I. ApoA-I is synthesized by the liver and small intestine as preproapolipoprotein which is secreted as a proprotein that is rapidly cleaved to generate a mature polypeptide having 243 amino acid residues. ApoA-I consists mainly of 6 to 8 different 22 amino acid repeats spaced by a linker moiety which is often proline, and in some cases consist of a stretch made up of several residues. ApoA-I forms three types of stable structures with lipids: small, lipid-poor complexes referred to as pre-beta-1 HDL; flattened discoidal particles containing only polar lipids (phospholipid and cholesterol) referred to as pre-beta-2 HDL; and spherical particles containing both polar and nonpolar lipids, referred to as spherical or mature HDL ($HDL_3$ and $HDL_2$). Most HDL in the circulating population contain both ApoA-I and ApoA-II (the second major HDL protein) and are referred to herein as the AI/AII-HDL fraction of HDL. However, the fraction of HDL containing only ApoA-I (referred to herein as the AI-HDL fraction) appear to be more effective in RCT. Certain epidemiologic studies support the hypothesis that the AI-HDL fraction is antiartherogenic. (Parra et al., 1992, Arterioscler. Thromb. 12:701–707; Decossin et al., 1997, Eur. J. Clin. Invest. 27:299–307)

Although the mechanism for cholesterol transfer from the cell surface is unknown, it is believed that the lipid-poor complex, pre-beta-1 HDL is the preferred acceptor for cholesterol transferred from peripheral tissue involved in RCT. Cholesterol newly transferred to pre-beta-1 HDL from the cell surface rapidly appears in the discoidal pre-beta-2 HDL. PLTP may increase the rate of disc formation, but data indicating a role for PLTP in RCT is lacking. LCAT reacts preferentially with discoidal and spherical HDL, transferring the 2-acyl group of lecithin or other phospholipids to the free hydroxyl residue of fatty alcohols, particularly cholesterol to generate cholesteryl esters (retained in the HDL) and lysolecithin. The LCAT reaction requires ApoA-I as activator; i.e., ApoA-I is the natural cofactor for LCAT. The conversion of cholesterol to its ester sequestered in the HDL prevents re-entry of cholesterol into the cell, the result being that cholesteryl esters are destined for removal. Cholesteryl esters in the mature HDL particles in the AI-HDL fraction (i.e., containing ApoA-I and no ApoA-II) are removed by the liver and processed into bile more effectively than those derived from HDL containing both ApoA-I and ApoA-II (the AI/AII-HDL fraction). This may be due, in part, to the more effective binding of AI-HDL to the hepatocyte membrane. The existence of an HDL receptor has been hypothesized, and recently a scavenger receptor, SR-BI, was identified as an HDL receptor. (Acton et al., 1996, Science 271:518–520). The SR-BI is expressed most abundantly in steroidogenic tissues (e.g., the adrenals), and in the liver. (Landshulz et al., 1996, J. Clin. Invest. 98:984–995; Rigotti et al., 1996, J. Biol. Chem. 271:33545–33549).

CETP does not appear to play a major role in RCT, and instead is involved in the metabolism of VLDL-and LDL-derived lipids. However, changes in CETP activity or its acceptors, VLDL and LDL, play a role in "remodeling" the HDL population. For example, in the absence of CETP, the HDLs become enlarged particles which are not cleared. (For reviews on RCT and HDLs, see Fielding & Fielding, 1995, J. Lipid Res. 36:211–228; Barrans et al., 1996, Biochem. Biophys. Acta. 1300:73–85; Hirano et al., 1997, Arterioscler. Thromb. Vasc. Biol. 17(b):1053–1059.

2.3. Current Treatments for Lowering Serum Cholesterol

A number of treatments are currently available for lowering serum cholesterol and triglycerides (see, e.g., Brown & Goldstein, supra). However, each has its own drawbacks and limitations in terms of efficacy, side-effects and qualifying patient population.

Bile-acid-binding resins are a class of drugs that interrupt the recycling of bile acids from the intestine to the liver; e.g., cholestyramine (Questran Light®, Bristol-Myers Squibb), and colestipol hydrochloride (Colestid®, The Upjohn Company). When taken orally, these positively-charged resins bind to the negatively charged bile acids in the intestine. Because the resins cannot be absorbed from the intestine, they are excreted carrying the bile acids with them. The use of such resins, however, at best only lowers serum cholesterol levels by about 20%, and is associated with gastrointestinal side-effects, including constipation and certain vitamin deficiencies. Moreover, since the resins bind other drugs, other oral medications must be taken at least one hour before or four to six hours subsequent to ingestion of the resin; thus, complicating heart patient's drug regimens.

The statins are cholesterol lowering agents that block cholesterol synthesis by inhibiting AMGCoA reductase—the key enzyme involved in the cholesterol biosynthetic pathway. The statins, e.g., lovastatin (Mevacor®, Merck & Co., Inc.) and pravastatin (Pravachol®, Bristol-Myers Squibb Co.) are sometimes used in combination with bileacid-binding resins. The statins significantly reduce serum cholesterol and LDL-serum levels, and slow progression of coronary atherosclerosis. However, serum HDL cholesterol levels are only slightly increased. The mechanism of the LDL lowering effect may involve both reduction of VLDL concentration and induction of cellular expression of LDL-receptor, leading to reduced production and/or increased catabolism of LDLs. Side effects, including liver and kidney dysfunction are associated with the use of these drugs (Physicians Desk Reference, Medical Economics Co., Inc., Montvale, N.J. 1997). Recently, the FDA has approved atorvasatatin (an HMGroA reductase inhibitor developed by Parke-Davis) (Warner Lambert) for the treatment of rare but urgent cases of familial hypercholesterolemia (1995, Scrip 20 (19):10).

Niacin, or nicotinic acid, is a water soluble vitamin B-complex used as a dietary supplement and antihyperlipidemic agent. Niacin diminishes production of VLDL and is effective at lowering LDL. It is used in combination with bile-acid binding resins. Niacin can increase HDL when used at adequate doses, however, its usefulness is limited by serious side effects when used at such doses.

Fibrates are a class of lipid-lowering drugs used to treat various forms of hyperlipidemia, (i.e., elevated serum triglycerides) which may also be associated with hypercholesterolemia. Fibrates appear to reduce the VLDL fraction and modestly increase HDL—however the effects of these drugs on serum cholesterol is variable. In the United States, fibrates have been approved for use as antilipidemic drugs but have not received approval as hypercholerolemia agents. For example, clofibrate (Atromid-S®, Wyeth-Ayerest Laboratories) is an antilipidemic agent which acts (via an unknown mechanism) to lower serum triglycerides by reducing the VLDL fraction. Although serum cholesterol may be reduced in certain patient subpopulations, the biochemical response to the drug is variable, and is not always possible to predict which patients will obtain favorable results. Atromid-S® has not been shown to be effective for prevention of coronary heart disease. The chemically and pharmacologically related drug, gemfibrozil (Lopid®, Parke-Davis) is a lipid regulating agent which moderately decreases serum triglycerides and VLDL cholesterol, and increases HDL cholesterol—the $HDL_2$ and $HDL_3$ subfractions as well as both ApoA-I and A-II (i.e., the AI/AII-HDL fraction). However, the lipid response is heterogeneous, especially among different patient populations. Moreover, while prevention of coronary heart disease was observed in male patients between 40–55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates including toxicity such as malignancy, (especially gastrointestinal cancer), gallbladder disease and an increased incidence in non-coronary mortality. These drugs are not indicated for the treatment of patients with high LDL or low HDL as their only lipid abnormality (Physicians' Desk Reference, 1997, Medical Economics Co., Inc., Montvale, N.J.)

Oral estrogen replacement therapy may be considered for moderate hypercholesterolemia in post-menopausal women. However, increases in HDL may be accompanied with an increase in triglycerides. Estrogen treatment is, of course, limited to a specific patent population (postmenopausal women) and is associated with serious side effects including induction of malignant neoplasms, gall bladder disease, thromboembolic disease, hepatic adenoma, elevated blood pressure, glucose intolerance, and hypercalcemia.

Thus, there is a need to develop safer drugs that are efficacious in lowering serum cholesterol, increasing HDL serum levels, preventing coronary heart disease, and/or treating existing disease.

2.4. ApoA-I as a Target

None of the currently available drugs for lowering cholesterol safely elevate HDL levels and stimulate RCT—most appear to operate on the cholesterol transport pathway, modulating dietary intake, recycling, synthesis of cholesterol, and the VLDL population.

While it is desirable to find drugs that stimulate cholesterol efflux and removal, several potential targets in the RCT exist—e.g., LCAT, HDL and its various components (ApoA-I, ApoA-II and phospholipids), LTP, and CETP—and it is not known which target would be most effective at achieving desirable lipoprotein profiles and protective effects. Perturbation of any single component in the RCT pathway ultimately affects the composition of circulating lipoprotein populations, and the efficiency of RCT.

Several lines of evidence based on data obtained in vivo implicate the HDL and its major protein component, ApoA-I, in the prevention of atherosclerotic lesions, and potentially, the regression of plaques—making these attractive targets for therapeutic intervention. First, an inverse correlation exists between serum ApoA-I (HDL) concentration and atherogenesis in man (Gordon & Rifkind, 1989, N. Eng. J. Med. 321:1311–1316; Gordon et al., 1989, Circulation 79:8–15). Indeed, specific subpopulations of HDL have been associated with a reduced risk for atherosclerosis in humans. (Miller, 1987, Amer. Heart 113:589–597; Cheung et al., 1991, Lipid Res. 32:383–394).

Second, animal studies support the protective role of ApoA-I (HDL). Treatment of cholesterol fed rabbits with ApoA-I or HDL reduced the development and progression of plaque (fatty streaks) in cholesterol-fed rabbits. (Koizumi et al., 1988, J. Lipid Res. 29:1405–1415; Badimon et al., 1989, Lab. Invest. 60:455–461; Badimon et al., 1990, J. Clin. Invest. 85:1234–1241). However, the efficacy varied depending upon the source of HDL (Beitz et al., 1992, Prostaglandins, Leukotrienes and Essential Fatty Acids 47:149–152; Mezdour et al., 1995, Atherosclerosis 113:237–246).

Third, direct evidence for the role of ApoA-I was obtained from experiments involving transgenic animals. The expression of the human gene for ApoA-I transferred to mice genetically predisposed to diet-induced atherosclerosis protected against the development of aortic lesions (Rubin et al., 1991, Nature 353:265–267). The ApoA-I transgene was also shown to suppress atherosclerosis in ApoE-deficient mice and in Apo(a) transgenic mice (Paszty et al., 1994, J. Clin. Invest. 94:899–903; Plump et al., 1994, Proc. Natl. Acad. Sci. USA 91:9607–9611, Lin et al., 1994, J. Lipid Res. 35:2263–2266). Similar results were observed in transgenic rabbits expressing human ApoA-I (Duverger, 1996, Circulation 94:713–717; Duverger et al., 1996, Arterioscler. Thromb. Vasc. Biol. 16:1424–1429; Emmanuel et al., 1997, Artheriosclerosis 1035:144), and in transgenic rats where elevated levels of human ApoA-I protected against atherosclerosis and inhibited restenosis following balloon angioplasty (Burkey et al., 1992, Circulation, Supplement I, 86:I-472, Abstract No. 1876; Burkey et al., 1995, J. Lipid Res. 36:1463–1473).

The AI-HDL appear to be more efficient at RCT than the AI/AII-HDL fraction. Studies with mice transgenic for human ApoA-I or ApoA-I and ApoA-II (AI/AII) showed that the protein composition of HDL significantly affects its role—AI-HDL is more anti-atterogenic than AI/AII-HDL (Schultz et al., 1993, Nature 365:762–764). Parallel studies involving transgenic mice expressing the human LCAT gene demonstrate that moderate increases in LCAT activity significantly change lipoprotein cholesterol levels, and that LCAT has a significant preference for HDL containing ApoA-I (Francone et al., 1995, J. Clinic. Invest. 96:1440–1448; Beard et al., 1997, Nature Medicine 3,7: 744–749). While these data support a significant role for ApoA-I in activating LCAT and stimulating RCT, additional studies demonstrate a more complicated scenario: a major component of HDL that modulates efflux of cell cholesterol is the phospholipid (Fournier et al., 1996, J. Lipid Res. 37:1704–1711).

In view of the potential role of HDL, i.e., both ApoA-I and its associated phospholipid, in the protection against atherosclerotic disease, human clinical trials utilizing recombinantly produced ApoA-I were commenced, discontinued and apparently recommenced by UCB Belgium (Pharma Projects, Oct. 27, 1995; IMS R&D Focus, Jun. 30, 1997; Drug Status Update, 1997, Atherosclerosis 2(6):261–265); see also M. Eriksson at Congress, "The Role of HDL in Disease Prevention," Nov. 7–9, 1996, Fort Worth; Lacko & Miller, 1997, J. Lipid Res. 38:1267–1273; and WO94/13819) and were commenced and discontinued by Bio-Tech (Pharmaprojects, Apr. 7, 1989). Trials were also attempted using ApoA-I to treat septic shock (Opal, "Reconstituted HDL as a Treatment Strategy for Sepsis," IBCs 7th Annual International Conference on Sepsis, Apr. 28–30, 1997, Washington, D.C.; Gouni et al., 1993, J. Lipid Res. 94:139–146; Levine WO96/04916). However, there are many pitfalls associated with the production and use of ApoA-I making it less than ideal as a drug; e.g., ApoA-I is a large protein that is difficult and expensive to produce; significant manufacturing and reproducibility problems must be overcome with respect to stability during storage, delivery of an active product and half-life in vivo.

In view of these drawbacks, attempts have been made to prepare peptides that mimic ApoA-I. Since the key activities of ApoA-I have been attributed to the presence of multiple repeats of a unique secondary structural feature in the protein—a class A amphipathic α-helix (Segrest, 1974, FEBS Lett. 38:247–253), most efforts to design peptides which mimic the activity of ApoA-I have focused on designing peptides which form class A-type amphipathic α-helices.

Class A-type amphipathic α-helices are unique in that positively charged amino acid residues are clustered at the hydrophobic-hydrophilic interface and negatively charged amino acid residues are clustered at the center of the hydrophilic face. Furthermore, Class A β-helical peptides have a hydrophobic angle of less than 180° (Segrest et al., PROTEINS, 1990; Structure, Function and Genetics 8:103–117). The initial de novo strategies to design ApoA-I mimics were not based upon the primary sequences of naturally occurring apolipoproteins, but rather upon incorporating these unique Class A helix features into the sequences of the peptide analogues as well as some of the properties of the ApoA-I domains (see, e.g., Davidson et al., 1996, Proc. Natl. Acad. Sci. USA 93:13605–13610; Rogers et al., 1997, Biochemistry 36:288–300; Lins et al., 1993, Biochim. Biophys. Acta biomembranes 1151:137–142; Ji and Jonas, 1995, J. Biol. Chem. 270:11290–11297; Collet et al., 1997, Journal of Lipid Research, 38:634–644; Sparrow and Gotto, 1980, Ann. N.Y. Acad. Sci. 348:187–211; Sparrow and Gotto, 1982, CRC Crit. Rev. Biochem. 13:87–107; Sorci-Thomas et al., 1993, J. Biol. Chem. 268:21403–21409; Wang et al., 1996, Biochim. Biophys. Acta 174–184; Minnich et al., 1992, J. Biol. Chem. 267: 16553–16560; Holvoet et al., 1995, Biochemistry 34:13334–13342; Sorci-Thomas et al., 1997, J. Biol. Chem. 272 (11):7278–7284; and Frank et al., 1997, Biochemistry 36:1798–1806).

In one study, Fukushima et al. synthesized a 22-residue peptide composed entirely of Glu, Lys and Leu residues arranged periodically so as to form an amphipathic α-helix with equal hydrophilic and hydrophobic faces ("ELK peptide") (Fukushima et al., 1980, J. Biol. Chem. .255:10651–10657; Fukushima et al., 1979, J. Amer. Chem. Soc. 101(13):3703–3704). The ELK peptide shares 41% sequence homology with the 198–219 fragment of ApoA-I. As studied by quantitative ultrafiltration, gel permeation chromatography and circular dichroism, this ELK peptide was shown to effectively associate with phospholipids and mimic some of the physical and chemical properties of ApoA-I (Kaiser et al., 1983, Proc. Natl. Acad. Sci. USA 80:1137–1140; Kaiser et al., 1984, Science 223:249–255; Fukushima et al., 1980, supra; Nakagawa et al., 1985, J. Am. Chem. Soc. 107:7087–7092). Yokoyama et al. concluded from such studies that the crucial factor for LCAT activation is simply the presence of a large enough amphipathic structure (Yokoyama et al., 1980, J. Biol. Chem. 255(15): 7333–7339). A dimer of this 22-residue peptide was later found to more closely mimic ApoA-I than the monomer; based on these results, it was suggested that the 44-mer which is punctuated in the middle by a helix breaker (either Gly or Pro), represented the minimal functional domain in ApoA-I (Nakagawa et al., 1985, supra).

Another study involved model amphipathic peptides called "LAP peptides" (Pownall et al., 1980, Proc. Natl. Acad. Sci. USA 77(b):3154–3158; Sparrow et al., 1981, In: Peptides:Synthesis-Structure-Function, Roch and Gross, Eds., Pierce Chem. Co., Rockford, Ill., 253–256). Based on lipid binding studies with fragments of native apolipoproteins, several LAP peptides were designed, designated LAP-16, LAP-20 and LAP-24 (containing 16, 20 and 24 amino acid residues, respectively). These model amphipathic peptides share no sequence homology with the apolipoproteins and were designed to have polar faces organized in a manner unlike the class A-type amphipathic helical domains associated with apolipoproteins. From these studies, the authors concluded that a minimal length of 20 residues is necessary to confer lipid-binding properties to model amphipathic peptides.

Studies with mutants of LAP20 containing a proline residue at different positions in the sequence indicated that a direct relationship exists between lipid binding and LCAT activation, but that the helical potential of a peptide alone does not lead to LCAT activation (Ponsin et al., 1986 J. Biol. Chem. 261(20):9202–9205). Moreover, the presence of this helix breaker (Pro) close to the middle of the peptide reduced its affinity for phospholipid surfaces as well as its ability to activate LCAT. While certain of the LAP peptides were shown to bind phospholipids (Sparrow et al., supra), controversy exists as to the extent to which LAP peptides are helical in the presence of lipids (Buchko et al., 1996, J. Biol. Chem. 271(6):3039–3045; Zhong et al., 1994, Peptide Research 7(2):99–106).

Segrest et al. have synthesized peptides composed of 18 to 24 amino acid residues that share no sequence homology with the helices of ApoA-I (Kannelis et al., 1980, J. Biol.

Chem. 255(3):11464–11472; Segrest et al., 1983, J. Biol. Chem. 258:2290–2295). The sequences were specifically designed to mimic the amphipathic helical domains of class A exchangeable apolipoproteins in terms of hydrophobic moment (Eisenberg et al., 1982, Nature 299:371–374) and charge distribution (Segrest et al., 1990, Proteins 8:103–117; U.S. Pat. No. 4,643,988). One 18-residue peptide, the "18A" peptide, was designed to be a model class-A α-helix (Segrest et al., 1990, supra). Studies with these peptides and other peptides having a reversed charged distribution, like the "18R" peptide, have consistently shown that charge distribution is critical for activity; peptides with a reversed charge distribution exhibit decreased lipid affinity relative to the 18A class-A mimics and a lower helical content in the presence of lipids (Kanellis et al., 1980, J. Biol. Chem. 255:11464–11472; Anantharamaiah et al., 1985, J. Biol. Chem. 260:10248–10255; Chung et al., 1985, J. Biol. Chem. 260:10256–10262; Epand et al., 1987, J. Biol. Chem. 262: 9389–9396; Anantharamaiah et al., 1991, Adv. Exp. Med. Biol. 285:131–140).

Other synthetic peptides sharing no sequence homology with the apolipoproteins which have been proposed with limited success include dimers and trimers. of the 18A peptide (Anatharamaiah et al., 1986, Proteins of Biological Fluids 34:63–66), GALA and EALA peptides (Subbarao et al., 1988, Proteins: Structure, Function and Genetics 3:187–198) and ID peptides (Labeur et al., 1997, Arteriosclerosis, Thrombosis, and Vascular Biology 17:580–588) and the 18AM4 peptide (Brasseur et al., 1993, Biochem. Biophys. Acta 1170:1–7).

A "consensus" peptide containing 22-amino acid residues based on the sequences of human ApoA-I has also been designed (Venkatachalapathi et al., 1991, Mol. Conformation and Bio. Interactions B:585–596). The sequence was constructed by identification of the most prevalent residue at each position of the helices of ApoA-I. Like the peptides described above, the helix formed by this peptide has positively charged amino acid residues clustered at the hydrophilic:hydrophobic interface, negatively charged amino acid residues clustered at the center of the hydrophilic face and hydrophobic angle of less than 180°. While a dimer of this peptide is somewhat effective in activating LCAT, the monomer exhibited poor lipid binding properties (Vekatachalapathi et al., 1991, supra).

Based primarily on in vitro studies with the peptides described above, a set of "rules" has emerged for designing peptides which mimic the function of ApoA-I. significantly, it is thought that an amphipathic α-helix having positively charged residues clustered at the hydrophilic-hydrophobic interface and negatively charged amino acid residues clustered at the center of the polar face is required for lipid affinity and LCAT activation (Venkatachalapathi et al., 1991, supra). Anantharamaiah et al., have also indicated that the negatively charged Glu residue at position 13 of the consensus 22-mer peptide, which is positioned within the hydrophobic face of the α-helix, plays an important role in LCAT activation (Anantharamaiah et al., 1991, supra). Furthermore, Brasseur has indicated that a hydrophobic angle (pho angle) of less than 180° is required for optimal lipid-apolipoprotein complex stability, and also accounts for the formation of discoidal particles having the peptides around the edge of a lipid bilayer (Brasseur, 1991, J. Biol. Chem. 66(24):16120–16127). Rosseneu et al., have also insisted that a hydrophobic angle of less than 180° is required for LCAT activation (WO93/25581).

However, despite these "rules" to date, no one has designed or produced a peptide as active as ApoA-I—the best having less than 40% of the activity of ApoA-I as measured by the LCAT activation assay described herein. None of the peptide "mimetics" described in the literature have not been demonstrated to be useful as a drug.

In view of the foregoing, there is a need for the development of a stable ApoA-I agonist that mimics the activity of ApoA-I, which is relatively simple and cost-effective to produce. However, the "rules" for designing efficacious ApoA-I mimetics have not been unraveled and the principles to devise organic molecules with the function of ApoA-I are unknown.

3. SUMMARY OF THE INVENTION

The invention relates to genetic approaches to supply nucleotide sequences encoding modified forms of the native forms of apolipoprotein A-I (ApoA-I): mature ApoA-I, preproApoA-I and proApoA-I; including native. ApoA-I modified to contain ApoA-I agonists, peptides which mimic the activity of ApoA-I; ApoA-I superagonists, peptides which exceed the activity of native ApoA-I; and modified native ApoA-I having one or more amphipathic helices replaced by the nucleotide sequences of one or more ApoA-I agonists; for the treatment of disorders associated with dyslipoproteinemia, including cardiovascular disease, atherosclerosis, restenosis, hyperlipidemia, and other disorders such as septic shock.

In particular, the invention relates to genetic approaches. to supply nucleotide sequences encoding modified native forms of the ApoA-I protein and peptides which act as ApoA-I agonists capable of forming amphipathic α-helices (in the presence of lipids) that approach or surpass the activity of native ApoA-I, e.g., formation of pre-β-like or HDL-like complexes, promotion of cholesterol efflux, binding to lipids, increasing the activity of LCAT, and increasing serum levels of HDL.

The present invention also relates to nucleotide sequences encoding a modified native ApoA-I having one or more amphipathic helices replaced by the nucleotide sequences of one or more ApoA-I agonists.

The present invention relates to DNA vectors or cassettes that contain nucleotide sequences encoding modified ApoA-I or peptides which act as ApoA-I agonists or superagonists. The invention further relates to DNA vectors or cassettes that contain nucleotide sequences encoding modified forms of the native ApoA-I gene. The DNA vectors or cassettes may encode modified forms of native ApoA-I or ApoA-I agonists under the control of strong regulatory elements which result in high levels of ApoA-I expression. To increase efficiency of production, the DNA expression vectors or cassettes may be designed to encode multiple units of the peptide, e.g., the cassettes may contain nucleotide sequences encoding several ApoA-I peptides in tandem, separated by an internal ribosome binding site, so that several peptides may be encoded by the same cassette. The vectors or cassettes may also express ApoA-I peptides as monopolymers (repeating peptide units) or heteropolymers (different peptide units). The cassettes of the present invention may also additionally encode prepropeptide or propeptide ApoA-I sequences so that the peptides of the present invention are processed in the same way as the native ApoA-I protein.

The present invention further relates to genetically engineered host cells which express the modified native forms of ApoA-I: mature ApoA-I, preproform or proform, peptides which mimic ApoA-I activity or the native ApoA-I gene product. The host cells may be genetically engineered in vitro or in vivo. The present invention also relates to transgenic animals engineered to express the ApoA-I peptides of the present invention.

The invention also relates to in vivo delivery applications for gene therapy, including administering engineered viral vectors or liposomes which contain DNA sequences encoding ApoA-I or ApoA-I agonist peptides in monomeric or heteromeric forms. The invention relates to ex vivo gene therapy approaches to provide engineered cells derived from a patient, or a compatible host, to express modified forms of the native ApoA-I gene,-ApoA-I agonists in monomeric or heteromeric form. Ex vivo gene therapy approaches may also encompass delivery of "sacs of cells" which have been genetically engineered to express the ApoA-I gene of the present invention, including, ApoA-I agonists in monomeric or heteromeric form and additional ApoA-I prosequences. In a preferred embodiment, human hepatocytes may be engineered to express ApoA-I agonists.

The invention is based, in part, on the Applicants' design and discovery of peptides that mimic the helical structure and amphipathic properties of the helical amphipathic domains of ApoA-I. Surprisingly, the peptides of the invention have a ApoA-I activity, i.e., formation of HDL-like complexes and promotion of cholesterol efflux, well above those reported for ApoA-I-derived peptides described in the literature. Indeed, some embodiments of the invention approach 100% of the activity of native ApoA-I, whereas superagonists described herein exceed the specific activity of ApoA-I.

The invention is illustrated by way of working examples that describe the in vitro and in vivo activity and efficacy of the ApoA-I peptides and agonists encoded by the nucleic acids of the present invention. Based upon the structure and activity of the exemplified embodiments, the Applicants have devised a set of "rules" which can be used to design altered or mutated forms that are also within the scope of the invention.

The invention also relates to pharmaceutical formulations containing such cell lines and vectors encoding modified forms of the native ApoA-I, i.e., mature ApoA-I, preproform of ApoA-I or proform of ApoA-I, or ApoA-I agonists (either as peptides or peptide-lipid complexes) as the active ingredient, as well as methods for preparing such formulations and their use to treat diseases associated with dyslipoproteinemia (e.g., cardiovascular diseases, atherosclerosis), restenosis, hyperlipidemia, hypertriglyceridemia, and/or endotoxinemia (e.g., septic shock).

3.1. Abbreviations

As used herein, the abbreviations for the genetically encoded amino acids are as follows:

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |

-continued

| Amino Acid | One-Letter Symbol | Common Abbreviation |
| --- | --- | --- |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

3.2. Definitions

As used herein, the following terms shall have the following meanings:

"Hydrophophilic Amino Acid" refers to an amino acid having a side chain that tends to associate with the aqueous phase or polar head of a phospholipid when in the presence of lipids. Genetically encoded hydrophilic amino acids include Asp (D), Glu (E), His (H), Lys (K), Arg (R), Asn (N), Gln (Q), Ser (S) and Thr (T).

"Acidic Amino Acid" refers to an amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to an amino acid having a side chain pK value of greater than 7. Basic amino acids typically have positively charged side chains at physiological pH due to association with hydronium ion. Genetically encoded basic amino acids include Arg (R) and Lys (K).

"Polar Amino Acid" refers to an amino acid having a side chain that is uncharged at physiological pH, but which has at least one bond wherein the pair of electrons shared in common by two atoms is held more closely by one of the atoms. Genetically encoded polar amino acids include Asn (N) and Gln (Q).

"Hydrophobic Amino Acid" refers to an amino acid having a side chain that tends to associate with the acyl chains of a phospholipid when in the presence of lipids. Genetically encoded hydrophobic amino acids include Phe (F), Tyr (Y), Trp (W), Leu (L), Val (V), Ile (I), Met (M), Gly (G), Ala (A) and Pro (P).

"Aromatic Amino Acid" refers to a hydrophobic amino acid with a side chain having at least one aromatic or heteroaromatic ring. The aromatic or heteroaromatic ring may contain one or more substituents. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds wherein the pair of electrons shared in common by two atoms is generally held equally by each at the two atoms (i.e., the side chain is not polar).

"AliPhatic Amino Acid" refers to a hydrophobic amino acid having an aliphatic hydrocarbon side chain. Genetically encoded aliphatic amino acids include Ala (A), Val (V), Leu (L) and Ile (I).

4. BRIEF DESCRIPTION OF THE FIGURES

FIG. 1. The nucleotide sequence (SEQ. ID NO.: 259) and amino acid sequence (SEQ. ID NO.: 260) for human ApoAI.

FIG. 2. Nucleotide sequences which encode core peptides of structure I (SEQ ID NOS.: 261, 262, & 263).

FIG. 3. Nucleotide sequences which encode core peptide of structure II (SEQ. ID NOS.: 264, 265, & 266).

FIG. 4. Nucleotide sequences which encode core peptides of structure III (SEQ. ID NOS.: 267, 268, & 269).

5. DETAILED DESCRIPTION OF THE INVENTION

The present invention relates to gene therapy approaches to provide nucleotide sequences encoding modified forms of the native ApoA-I gene, nucleotide sequences encoding ApoA-I agonists which mimic ApoA-I function and activity or surpass native ApoA-I function and activity, for the treatments of disorders associated with hypercholesterolemia.

The nucleotide sequences of the present invention encode peptides which form amphipathic helices (in the presence of lipids), bind lipids, form pre-β like or HDL-like complexes, activate LCAT, increase serum HDL concentration and promote cholesterol efflux.

The biological function of encoded peptides appears to correlate with their helical structures, or conversion to helical structures in the presence of lipids.

At least three types of DNA vectors or cassettes can be designed and constructed in accordance with the present invention, to contain nucleotide sequences of the native human ApoA-I gene; modified forms of the native or proform of ApoA-I; nucleotide sequences encoding ApoA-I agonists in preform and proform; and nucleotide sequences encoding ApoA-I agonists and superagonists. The DNA vectors or cassettes may also express the ApoA-I peptides as homopolymers (repeating peptide units) or heteropolymers (different peptide units) in order to increase efficiency of production.

The invention further relates to genetically engineered host cells which express the ApoA-I peptide agonists of the present invention. The host cells may be engineered in vivo or in vitro. The present invention further relates to in vivo and in vitro gene therapy approaches to express ApoA-I peptide agonists in a host. The present invention also relates to transgenic animals engineered to express the modified forms of the native or proform of ApoA-I and ApoA-I peptide agonists of the present invention.

The nucleotide sequences encoding ApoA-I agonists of the invention can be provided as naked RNA or DNA sequences, in vectors, such as viral vectors or by transfected cells. The invention includes the pharmaceutical formulations and the use of such preparations in the treatment of dyslipoproteinemia, hyperlipidemia, hypercholesterolemia, coronary heart disease, atherosclerosis, and other conditions such as endotoxinemia/septic shock.

The invention is based, in part, on the Applicant's discovery that the ApoA-I agonists of the invention associate with the HDL component of plasma, and can increase the concentration of HDL and pre-β particles. The ApoA-I agonists of the invention increase cholesterol efflux from extrahepatic tissues. The agonists are also extremely efficient at activating LCAT, and thus promote RCT. Use of the ApoA-I agonists of the invention in vivo in animal models results in an increase in serum HDL concentration.

The invention is set forth in more detail in the subsections below, which describe: the nucleotide sequences encoding the native form of ApoA-I, the preproform of ApoA-I, modified forms of the native or proform of ApoA-I and ApoA-I peptide agonists, the vectors and cell lines which may be designed to express these nucleotide sequences; in vivo and ex vivo gene therapy approaches to provide these nucleotide sequences; and methods of preparation of bulk and unit dosage formulations; and methods of use.

5.1. Nucleotide Sequences Encoding ApoA-I and ApoA-I Agonists

The nucleotide sequences of the present invention encode ApoA-I peptides or ApoA-I agonists which are capable of forming regions of amphipathic α-helices in the presence of lipids and which mimic the activity of ApoA-I. Nucleotide sequences encoding the ApoA-I agonists and ApoA-I peptides are described herein.

The present invention also encompasses nucleotide sequences encoding the full lengthApoA-I gene (SEQ. ID NO.: 259 (FIG. 1)) which have been modified to enhance or increase the ApoA-I like activities of the expressed gene product, i.e., form amphipathic helices (in the presence of lipids), bind lipids, form pre-β-like or HDL-like complexes, activate LCAT, increase serum HDL concentration and promote cholesterol efflux. The present invention also encompasses nucleotide sequences which encode modified forms of native ApoA-I, i.e., nucleotide sequences encoding a modified ApoA-I, having one, two or more amphipathic helices replaced by at least two ApoA-I agonists.

The present invention also relates to nucleotide sequences which encode modified forms of ApoA-II, ApoA-III, ApoA-IV, ApoB, ApoC-I, ApoC-II, ApoC-III, ApoD and ApoE which have been modified to encode one, two or more ApoA-I agonists of the present invention (see e.g., Lusis, 1988, J of Lipid Res. 29:397–428, incorporated herein by reference in its entirety).

The nucleotide sequences of the present invention also encompass nucleotide sequences encoding core peptides of Structure I (e.g., SEQ ID NOS.: 261, 262, & 263 (FIG. 2)), core peptides of Structure II (e.g., SEQ ID NOS.: 264, 265, & 266 (FIG. 3)) or core peptides of Structure III (e.g., SEQ ID NOS. :267, 268, & 269 (FIG. 4)).

The invention also encompasses:

(a) DNA vectors that contain any of the foregoing ApoA-I coding sequences and/or their complements (i.e., antisense);

(b) DNA expression vectors that contain any of the foregoing ApoA-I coding sequences operatively associated with a regulatory element that directs the expression of the coding sequences;

(c) DNA expression vectors or cassettes encoding ApoA-I agonists in tandem separated by a internal ribosome binding site so that several of the same coding sequence may be expressed from the same cassette or several different coding sequences expressing different ApoA-I agonists may be expressed from the same cassette;

(d) genetically engineered host cells that contain any of the foregoing ApoA-I coding sequences operatively associated with a regulatory element that directs the expression of the coding sequences in the host cell.

As used herein, regulatory elements include, but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of the SV40 adenovirus, the lac system, the trp system, the TAC system, the TRC system, the major operator and promoter regions of phage A, the control regions of the fd coat protein, the promoter for 3-phosphoglycerate kinase, the promoters of acid phosphatase, and the promoters of the yeast α-mating factors.

5.1.1. The Native APoA-I Gene

The ApoA-I gene encodes the principal protein constituent of HDL and is associated with the regulation of cholesterol efflux and the serum HDL concentration. Nucleic acids encoding the ApoA-I gene of the present invention are described herein for use in gene therapy approaches for treating disorders associated with dyslipidemia. As used herein the ApoA-I gene of the present invention includes, but is not limited to:

(a) a nucleic acid molecule containing the cDNA encoding human ApoA-I, the full length human ApoA-I cDNA comprises 842 nucleotides (SEQ ID NO.: 259 (FIG. 1)) (see Shoulders et al., 1983, Nucleic Acids Research 11:2827–2837, incorporated herein by reference in its entirety) in which nucleotide sequences encoding at least one of the 22 amino acid repeats are replaced by nucleotide sequences encoding the ApoA-I agonists of the present invention;

(b) a nucleic acid molecule containing the genomic sequence of human ApoA-I which contains at least two introns of 185 and 588 nucleotides (see Shoulders et al., 1983, Nucleic Acids Research 11:2827–2837, incorporated herein by reference in its entirety);

(c) a nucleic acid molecule containing the DNA sequences encoding 1 to 8 of the different 22 amino acid repeats found in the native human ApoA-I, and may further contain the DNA sequences encoding the linker or spacer moieties found between one or more of the repeats;

(d) a nucleic acid molecule containing the DNA sequences encoding a modified ApoA-I in which at least one amphipathic helix is replaced by the sequence of at least one ApoA-I agonist;

(e) a nucleic acid molecule containing all or a portion of (a), (b), (c) or (d) and additionally the DNA sequences encoding the prepropeptide segment or leader peptide which encompasses the first 18 amino acids of the amino terminus of ApoA-I. The leader peptide of human ApoA-I, 5'MKAAVLTLAVLFLTGSQA3' (SEQ ID NO.: 270), is cleaved following secretion of ApoA-I from the host cell (f) a nucleic acid molecule containing all or a portion of (a), (b), (c), (d) or (e) and additionally the DNA sequences encoding the propeptide segment which encompasses a 6 amino acid sequence, 5'RHFWQQ3' (SEQ ID NO.:272), which is cleaved by specific proteases resulting in a mature ApoA-I; and or (g) a nucleic acid molecule containing a DNA sequence encoding a gene product functionally equivalent to an ApoA-I peptide.

The term "functionally equivalent to an ApoA-I peptide" as used herein, refers to a gene product that exhibits one of the biological activities of an ApoA-I peptide including formation of amphipathic helices (in the presence of lipids), binding to lipids, formation of pre-β-like or HDL-like complexes, activation of LCAT, increasing serum HDL concentration and promotion of cholesterol efflux. According to this aspect, the invention also includes nucleotide sequences which encode modified forms of ApoA-II, ApoA-III, ApoA-IV, ApoB, ApoC-I, ApoC-II, ApoC-III, ApoD and ApoE which have been modified to encode one, two or more ApoA-I agonists of the present invention.

The invention also includes nucleic acid molecules, preferably DNA molecules, that hybridize to, and are therefore the complements of, the DNA sequences described above encoding native ApoA-I. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as ApoA-I agonist antisense molecules, useful, for example, in ApoA-I gene regulation, for and/or as antisense primers in amplification reactions of ApoA-I nucleic acid sequences. With respect to ApoA-I gene regulation, such techniques may be used to regulate, for example a hypercholesterolemia disorder. Further, such sequences may be used as part of ribozyme and/or triple helix sequences, also useful for gene regulation of mutant forms of ApoA-I which may display ApoA-I antagonist properties. Still further, such molecules may be used as components of diagnostic methods whereby, for example, the presence of a particular mutant ApoA-I allele responsible for causing a hypercholesterolemia disorder may be detected.

In addition to those human sequences described herein, additional ApoA-I gene sequences can be identified and readily isolated, with out undue experimentation, by molecular biological techniques well known in the art.

5.1.2. ApoA-I Peptides and ApoA-I Agonists

The nucleotide sequences may encode ApoA-I peptides or agonists which have as their main feature a "core" peptide. composed of 15 to 23 amino acid residues. The amino acid sequence of this core peptide is based upon the amino acid sequences of a family of peptides which the Applicants have discovered mimic the structure and amphipathic helical properties of ApoA-I, and which exhibit specific activities that approach, or in some embodiments even exceed, the specific activity of native ApoA-I.

The nucleotide sequences of the present invention encoding ApoA-I peptides and agonists may be expressed on their own, in multimeric form or may be expressed as a chimeric with nucleotide sequences encoding native or proform of ApoA-I.

The ApoA-I agonists of the invention are based, in part, on the Applicants' surprising discovery that altering certain amino acid residues in the primary sequence of the 22-mer consensus sequence of Venkatachalapathi et al., 1991, Mol. Conformation and Biol. Interactions B:585–596 (PVLDE-FREKLNEELEALKQKLK; SEQ ID NO: 75; hereinafter "Segrest's consensus 22-mer" or "consensus 22-mer") that were thought to be critical for activity yields synthetic peptides that exhibit activities that approach, or in some embodiments even exceed, the activity of native ApoA-I. In particular, the Applicants have discovered that replacing three charged amino acid residues in Segrest's consensus 22-mer peptide (Glu-5, Lys-9 and Glu-13) with a hydrophobic. Leu residue provides peptides that mimic the structural and functional properties of ApoA-I to a degree that is unprecedented in the art.

While not intending to be bound by any particular theory, it is believed that the helix formed by the ApoA-I agonists of the invention more closely mimics the structural and functional properties of the amphipathic helical regions of native ApoA-I that are important for effecting lipid-binding, cholesterol efflux and LCAT activation than does the α-helix formed by the ApoA-I mimetic peptides described in the literature, thereby resulting in peptides that exhibit significantly higher ApoA-I-like activity than these other peptides. Indeed, whereas many of the ApoA-I agonists of the invention approach, and in some embodiments even exceed, the activity of ApoA-I, to date, the best peptide ApoA-I mimics described in the literature—peptide 18AM4 (SEQ ID NO: 246); Corinjn et al., 1993, Biochim. Biophys. Acta 1170: 8–16; Labeur et al., October 1994, Arteriosclerosis: Abstract Nos. 186 and 187; and N-acetylated, C-amidated peptide 18AM4 (SEQ ID NO: 239) (Brasseur, 1993, Biochim. Biophys. Acta 1170:1–7)—exhibit less than 4% and 11%, respectively, of the activity of ApoA-I as measured by the LCAT activation assay described herein.

In an illustrative embodiment of the invention, the nucleotide sequences encode core peptides (or analogues thereof) that compose the ApoA-I agonists of the invention having the following structural formula:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}X_{22} \quad (I)$$

wherein:
$X_1$ is Pro (P), Ala (A), Gly (G), Gln (Q), Asp (D) or Asn (N);
$X_2$ is an aliphatic amino acid;
$X_3$ is Leu (L) or Phe (F);
$X_4$ is an acidic amino acid;
$X_5$ is Leu (L) or Phe (F);
$X_6$ is Leu (L) or Phe (F);
$X_7$ is a hydrophilic amino acid;
$X_8$ is an acidic or a basic amino acid;
$X_9$ is Leu (L) or Gly (G);
$X_{10}$ is Leu (L), Trp (W) or Gly (G);
$X_{11}$ is a hydrophilic amino acid;
$X_{12}$ is a hydrophilic amino acid;
$X_{13}$ is Gly (G) or an aliphatic amino acid;
$X_{14}$ is Leu (L), Trp (W) or Gly (G);
$X_{15}$ is a hydrophilic amino acid;
$X_{16}$ is a hydrophobic amino acid;
$X_{17}$ is a hydrophobic amino acid;
$X_{18}$ is a basic amino acid, Gln (Q) or Asn (N);
$X_{19}$ is a basic amino acid, Gln (Q) or Asn (N);
$X_{20}$ is a basic amino acid;
$X_{21}$ is an aliphatic amino acid; and
$X_{22}$ is a basic amino acid.

In the core peptides of structure (I), the symbol "-" between amino acid residues generally designates a ackbone constitutive linking function. Thus, the symbol "-" sually represents a peptide bond or amide linkage.

The present invention encompasses nucleotide sequences which encode peptides which are functionally equivalent to the peptides of structure (I), for a more detailed description see U.S. patent application Ser. No. 08/940,095, now U.S. Pat. No. 6,004,925, page 25, line 6 to page 58, line 21, incorporated herein by reference in its entirety.

In a further illustrative embodiment of the present invention, the nucleotide sequences encode core peptides (or analogues thereof) that compose the ApoA-I agonists of the invention having the following structural formula:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18}\text{-}X_{19}\text{-}X_{20}\text{-}X_{21}\text{-}X_{22} \quad (II)$$

wherein:
$X_1$ is Pro (P), Ala (A), Gly (G), Gln (Q), Asn (N) or Asp (D);
$X_2$ is an aliphatic amino acid;
$X_3$ is Leu (L) or Phe (F);
$X_4$ is Glu (E);
$X_5$ is an aliphatic amino acid;
$X_6$ is Leu (L) or Phe (F);
$X_7$ is Glu (E) or Leu (L);
$X_8$ is Asn (N) or Gln (Q);
$X_9$ is Leu (L);
$X_{10}$ is Leu (L), Trp (W) or Gly (G);
$X_{11}$ is an acidic amino acid;
$X_{12}$ is Arg (R);
$X_{13}$ is Leu (L) or Gly (G);
$X_{14}$ is Leu (L), Phe (F) or Gly (G);
$X_{15}$ is Asp (D);
$X_{16}$ is Ala (A);
$X_{17}$ is Leu (L);
$X_{18}$ is Asn (N) or Gln (Q);
$X_{19}$ is a basic amino acid;
$X_{20}$ is a basic amino acid;
$X_{21}$ is Leu (L); and
$X_{22}$ is a basic amino acid.

Each "-" independently designates a peptide bond or amide linkage.

The present invention encompasses nucleotide sequences which encode peptides which are functionally equivalent to the peptides of structure (II), for a more detailed description see U.S. patent application Ser. No. 08/940,096, now U.S. Pat. No. 6,046,166, page 25, line 6 to page 58, line 21, incorporated herein by reference in its entirety.

In yet a further illustrative embodiment of the present invention, the nucleotide sequences encode core peptides (or analogues thereof) that compose the ApoA-I agonists of the invention having the following structural formula:

$$X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-}X_{13}\text{-}X_{14}\text{-}X_{15}\text{-}X_{16}\text{-}X_{17}\text{-}X_{18} \quad (III)$$

$X_1$ is Pro (P), Ala (A), Gly (G), Asn (N) or Gln (Q);
$X_2$ is an aliphatic amino acid;
$X_3$ is Leu (L);
$X_4$ is an acidic amino acid;
$X_5$ is Leu (L) or Phe (F);
$X_6$ is Leu (L) or Phe (F);
$X_7$ is a basic amino acid;
$X_8$ is an acidic amino acid;
$X_9$ is Leu (L) or Trp (W);
$X_{10}$ is Leu (L) or Trp (W);
$X_{11}$ is an acidic amino acid or Asn (N);
$X_{12}$ is an acidic amino acid;
$X_{13}$ is Leu (L), Trp (W) or Phe (F);
$X_{14}$ is a basic amino acid or Leu (L);
$X_{15}$ is Gln (Q) or Asn (N);
$X_{16}$ is a basic amino acid;
$X_{17}$ is Leu (L); and
$X_{18}$ is a basic amino acid.

Each "-" independently designates a peptide bond or amide linkage.

The present invention encompasses nucleotide sequences which encode peptides which are functionally equivalent to the peptides of structure (III), for a more detailed description see U.S. patent application Ser. No. 08/940,097, now U.S. Pat. No. 6,037,323, page 24, line 31 to page 58, line 3, incorporated herein by reference in its entirety.

The core peptides of structure (I), (II) and (III) are defined, in part, in terms of amino acids of designated classes. The definitions of the various designated classes are provided infra in connection with the description of mutated or altered embodiments of structure (I), (II) and (III).

All other letters in structures (I), (II) and (III) refer to the one-letter amino acid abbreviations commonly employed in the art, as previously described. The nucleotide sequence of the peptides may be deduced as follows:

TABLE I

|   | SECOND BASE | | | |
|---|---|---|---|---|
|   | U | C | A | G |
| U | UUU } Phe<br>UUC<br>UUA } Leu<br>UUG | UUU }<br>UCC } Ser<br>UCA<br>UCG | UAU } Tyr<br>UAC<br>UAA } TERM<br>UAG | UGU } Cys<br>UGC<br>UGA TERM<br>UGG Trp |
| C | CUU }<br>CUC } Leu<br>CUA<br>CUG | CCU }<br>CCC } Pro<br>CCA<br>CCG | CAU } His<br>CAC<br>CAA } Gln<br>CAG | CGU }<br>CGC } Arg<br>CGA<br>CGG |
| A | AUU } Ile<br>AUC<br>AUA<br>AUG Met | ACU }<br>ACC } Thr<br>ACA<br>ACG | AAU } Asn<br>AAC<br>AAA } Lys<br>AAG | AGU } Ser<br>AGC<br>AGA } Arg<br>AGG |
| G | GUU }<br>GUC } Val<br>GUA<br>GUG | GCU }<br>GCC } Ala<br>GCA<br>GCG | GAU } Asp<br>GAC<br>GAA } Glu<br>GAG | GGU }<br>GGC } Gly<br>GGA<br>GGG |

While not intending to be bound by any particular theory, it is believed that the nucleotide sequences of the present invention encode peptides which form an amphipathic α-helix formed in the presence of lipids more closely mimics the structural and amphipathic properties of the helical regions of native ApoA-I that are important for effecting lipid-binding, cholesterol efflux and LCAT activation than does the α-helix formed by the peptides described in the literature, thereby resulting in peptides that exhibit significantly higher ApoA-I-like activity than these other peptides. Indeed, whereas many of the core peptides of structure (I), (II) and (III) approach, and in some embodiments even exceed, the activity of ApoA-I, to date the best peptide ApoA-I mimic described in the literature has less than 40% of the activity of ApoA-I as measured by the LCAT activation assay described herein.

While not intending to be bound by any particular theory, it is believed that certain structural and/or physical properties of the amphipathic helix formed by the core peptides of structure (I), (II) and (III) are important for activity. These properties include the degree of amphipathicity, overall hydrophobicity, mean hydrophobicity, hydrophobic and hydrophilic angles, hydrophobic moment, mean hydrophobic moment, net charge and dipole moment.

A summary of the preferred physical and structural properties of the core peptides of structure (I), (II) and (III) is provided in TABLES II, III and IV below:

TABLE II

PHYSICAL PROPERTIES OF PREFERRED
ApoA-I AGONISTS OF STRUCTURE (I)

| PROPERTY | RANGE | PREFERRED RANGE |
|---|---|---|
| % hydrophobic amino acids | 40–70 | 50–60 |
| $<H_o>$ | −0.050 to −0.070 | −0.030 to −0.055 |
| $<H_o^{pho}>$ | 0.90–1.2 | 0.94–1.1 |
| $<\mu_H>$ | 0.45–0.65 | 0.50–0.60 |
| pho angle | 160°–220° | 180°–200° |
| # positively charged amino acids | 3–5 | 4 |
| # negatively charged amino acids | 3–5 | 4 |
| net charge | −1 to +1 | 0 |

TABLE II-continued

PHYSICAL PROPERTIES OF PREFERRED
ApoA-I AGONISTS OF STRUCTURE (I)

| PROPERTY | RANGE | PREFERRED RANGE |
|---|---|---|
| hydrophobic cluster | positions 3, 6, 9, 10 are hydrophobic amino acids | |
| acidic cluster | at least 1 acidic amino acid per turn except for last 5 C-terminal amino acids | |
| basic cluster | at least 3 basic amino acids in last 5 C-terminal amino acids | |

TABLE III

PHYSICAL PROPERTIES OF PREFERRED
ApoA-I AGONISTS OF STRUCTURE (II)

| PROPERTY | RANGE | PREFERRED RANGE |
|---|---|---|
| % hydrophobic amino acids | 40–70 | 50–60 |
| $<H_o>$ | −0.050 to −0.070 | −0.030 to −0.055 |
| $<H_o^{pho}>$ | 0.90–1.2 | 0.94–1.1 |
| $<\mu_H>$ | 0.45–0.65 | 0.50–0.60 |
| pho angle | 160°–220° | 180°–200° |
| # positively charged amino acids | 3–5 | 4 |
| # negatively charged amino acids | 3–5 | 4 |
| net charge | −1 to +1 | 0 |
| hydrophobic cluster | positions 3, 6, 9, 10 are hydrophobic amino acids | |
| acidic cluster | at least 1 acidic amino acid per turn except for last 5 C-terminal amino acids | |
| basic cluster | at least 3 basic amino acids in last 5 C-terminal amino acids | |

TABLE IV

PHYSICAL PROPERTIES OF PREFERRED
ApoA-I AGONISTS OF STRUCTURE (III)

| PROPERTY | RANGE | PREFERRED RANGE |
|---|---|---|
| % hydrophobic amino acids | 40–70 | 50–60 |
| $<H_o>$ | −0.150 to −0.070 | −0.130 to −0.050 |
| $<H_o^{pho}>$ | 0.90–1.2 | 0.95–1.10 |
| $<\mu_H>$ | 0.55–0.65 | 0.58–0.62 |
| pho angle | 120°–160° | 130°–150° |
| # positively charged amino acids | 3–5 | 4 |
| # negatively charged amino acids | 3–5 | 4 |
| net charge | −1 to +1 | 0 |
| hydrophobic cluster | positions 3, 6, 9, 10 are hydrophobic amino acids | |
| acidic cluster | at least 1 acidic amino acid per turn except for last 5 C-terminal amino acids | |
| basic cluster | at least 2 basic amino acids in last 5 C-terminal amino acids | |

The properties of the amphipathic α-helices formed by the core peptides of the invention differ significantly from the properties of class A amphipathic α-helices, particularly the class A α-helix of Segrest's 18A and consensus 22-mer peptides. These differences are illustrated with exemplary core peptide 210 (SEQ ID NO: 210).

A comparison of the physical and structural properties of peptide 210 (SEQ ID NO:210) and Segrest's 18A peptide (SEQ ID NO:244) and consensus 22-mer peptide (SEQ ID NO:75) is provided in TABLE V, below:

TABLE V

COMPARISON OF PROPERTIES OF EXEMPLARY
CORE PEPTIDE 210 (SEQ ID NO: 210) WITH
SEGREST'S CONSENSUS 22-MER (SEQ ID NO: 75)
AND 18A PEPTIDE (SEQ ID NO: 244)

| PROPERTY | 18A | CONSENSUS 22-MER | PEPTIDE 210 |
|---|---|---|---|
| # amino acids | 18 | 22 | 18 |
| # hydrophilic amino acids | 9 | 13 | 9 |
| # hydrophobic amino acids | 9 | 9 | 9 |
| % hydrophobic amino acids | 50 | 41 | 50 |
| $<H_o>$ | −0.43 | −0.293 | −0.125 |
| $<H_o^{pho}>$ | 0.778 | 0.960 | 1.081 |
| $<\mu_H>$ | 0.485 | 0.425 | 0.597 |
| pho angle | 100° | 100° | 140° |
| # positively charged amino acids | 4 | 5 | 4 |
| # negatively charged amino acids | 4 | 6 | 4 |
| net charge | 0 | −1 | 0 |

These differences in properties lead to significant differences in activity. Whereas Segrest's 18A peptide (SEQ ID NO:244) and consensus 22-mer peptide (SEQ ID NO:75) exhibit only 5% and 10% LCAT activation, respectively, as compared with native ApoA-I in the assays described herein, peptide 210 (SEQ ID NO:210) exhibits 46% activation as compared with native ApoA-I in the same assays.

Certain amino acid residues in the core peptides of structure (I), (II) and (III) can be replaced with other amino acid residues without significantly deleteriously affecting, and in many cases even enhancing, the activity of the peptides. Thus, also contemplated by the present invention are mutated forms of the core peptides of structure (I), (II) and (III) wherein at least one defined amino acid residue in the structure is substituted with another amino acid. As one of the critical features affecting the activity of the core peptides of the invention is believed to be their ability to form α-helices in the presence of lipids that exhibit the amphipathic and other properties described above, it will be recognized that in preferred embodiments of the invention, the amino acid substitutions are conservative, i.e., the replacing amino acid residue has physical and chemical properties that are similar to the amino acid residue being replaced.

For purposes of determining conservative amino acid substitutions, the amino acids can be conveniently classified into two main categories—hydrophilic and hydrophobic—depending primarily on the physical-chemical characteristics of the amino acid side chain. These two main categories can be further classified into subcategories that more distinctly define the characteristics of the amino acid side chains. For example, the class of hydrophilic amino acids can be further subdivided into acidic, basic and polar amino acids. The class of hydrophobic amino acids can be further subdivided into apolar and aromatic amino acids. The definitions of the various categories of amino acids that define structure (I), (II) and (III) are as follows:

"Hydrophophilic Amino Acid" refers to an amino acid exhibiting a hydrophobicity of less than zero according to the consensus hydrophobicity scale of Eisenberg, 1984, Ann. Rev. Biochem. 53:595–623. Genetically encoded hydrophilic amino acids include Pro (P), Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Cys (C), Asn (N), Gln (Q) Ser (S) and Thr (T).

"Hydrophobic Amino Acid" refers to an amino acid exhibiting a hydrophobicity of greater than zero according to the consensus hydrophobicity scale of Eisenberg, 1984, Ann. Rev. Biochem. 53:595–623. Genetically encoded hydrophobic amino acids include Ile (I), Phe (F), Val (V), Leu (L), Trp (W), Met (M), Ala (A), Gly (G) and Tyr (Y).

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$–$C_6$) alkyl, substituted ($C_1$–$C_6$) alkyl, ($C_1$–$C_6$) alkenyl, substituted ($C_1$–$C_6$) alkenyl, ($C_1$–$C_6$) alkynyl, substituted ($C_1$–$C_6$) alkynyl, ($C_5$–$C_{20}$) aryl, substituted ($C_5$–$C_{20}$) aryl, ($C_6$–$C_{26}$) alkaryl, substituted ($C_6$–$C_{26}$) alkaryl, 5–20 membered heteroaryl or substituted 5–20 membered heteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfanyl-containing amino acids. The ability of Cys (C) residues (and other amino acids with —SH containing side chains) to exist in a peptide in either the reduced free —SH or oxidized disulfide-bridged form affects whether Cys (C) residues contribute net hydrophobic or hydrophilic character to a peptide. While Cys (C) exhibits a hydrophobicity of 0.04 according to the consensus scale of Eisenberg (Eisenberg, 1984, supra), it is to be understood that for purposes of the present invention Cys (C) is categorized as a polar hydrophilic amino acid, notwithstanding the general classifications defined above.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

Certain amino acid residues, called "helix breaking" amino acids, have a propensity to disrupt the structure of α-helices when contained at internal positions of the helix. Amino acid residues exhibiting helix-breaking properties are well-known in the art (see, e.g., Chou and Fasman, Ann. Rev. Biochem. 47:251–276) and include Pro (P), D-Pro (p) and Gly (G). While these amino acids conveniently fall into the categories defined above, with the exception of Gly (G) these residues should not be used to substitute amino acids at internal positions within the helix—they should only be used to substitute 1–3 amino acid residues at the N-terminus and/or C-terminus of the peptide.

The native structure of ApoA-I contains eight helical units that are thought to act in concert to bind lipids (Nakagawa et al., 1985, J. Am. Chem. Soc. 107:7087–7092; Ananthara-maiah et al., 1985, J. Biol. Chem. 260:10248–10262; Vanloo et al., 1991, J. Lipid Res. 32:1253–1264; Mendez et al., 1994, J. Clin. Invest. 94:1698–1705; Palgunari et al., 1996, Arterioscler. Thromb. Vasc. Biol. 16:328–338; Demoor et al., 1996, Eur. J. Biochem. 239:74–84). Thus, also included in the present invention are ApoA-I agonists comprised of dimers, trimers, tetramers and even higher order polymers ("multimers") of the core peptides described herein. Such multimers may be in the form of tandem repeats, branched networks or combinations thereof. The core peptides may be directly attached to one another or separated by one or more linkers.

The core peptides that comprise the multimers may be the peptides of structure (I), (II) or (III) analogues of structure (I), (II) or (III), mutated forms of structure (I), (II) or (III) truncated or internally deleted forms of structure (I), (II) or (III) extended forms of structure (I), (II) or (III) and/or combinations thereof. The core peptides can be connected in a head-to-tail fashion (i.e., N-terminus to C-terminus), a head-to-head fashion, (i.e., N-terminus to N-terminus), a tail-to-tail fashion (i.e., C-terminus to C-terminus), or combinations thereof.

In one embodiment of the invention, the multimers are tandem repeats of two, three, four and up to about ten core peptides. Preferably, the multimers are tandem repeats of from 2 to 8 core peptides. Thus, in one embodiment, the ApoA-I agonists of the invention comprise multimers having the following structural formula:

HH-[LL$_m$-HH]$_n$LL$_m$-HH         (IV)

wherein:

each m is independently an integer from 0 to 1, preferably 1;

n is an integer from 0 to 10, preferably 0 to 8;

each "HH" independently represents a core peptide or peptide analogue of structure (I) or a mutated, truncated, internally deleted or extended form thereof as described herein;

each "LL" independently represents a linker, e.g., Pro (P), Gly (G) and Cys-Cys.

In a preferred embodiment of the invention, the tandem repeats are internally punctuated by a single proline residue.

To this end, in those instances where the core peptides are terminated at their N- or C-terminus with proline, such as, e.g., where $X_1$ in structure (I) is Pro (P). In those instances where the core peptides do not contain an N- or C-terminal proline, LL is preferably Pro (P).

In certain embodiments of the invention, it may be desirable to employ cleavable linkers that permit the release of one or more helical segments (HH) under certain conditions. Suitable cleavable linkers include peptides having amino acid sequences that are recognized by proteases, oligonucleotides that are cleaved by endonucleases. Preferably, the cleavage conditions will be relatively mild so as not to denature or otherwise degrade the helical segments and/or non-cleaved linkers composing the multimeric ApoA-I agonists.

Peptide and oligonucleotide linkers that can be selectively cleaved, as well as means for cleaving the linkers are well known and will be readily apparent to those of skill in the art.

In a preferred embodiment, the linkers employed are peptides that are substrates for endogenous circulatory enzymes, thereby permitting the multimeric ApoA-I agonists to be selectively cleaved in vivo. Endogenous enzymes suitable for cleaving the linkers include, for example, proapolipoprotein A-I propeptidase. Appropriate enzymes, as well as peptide segments that act as substrates for such enzymes, are well-known in the art (see, e.g., Edelstein et al., 1983, J. Biol. Chem. 258:11430–11433; Zanis, 1983, Proc. Natl. Acad. Sci. USA 80:2574–2578).

As discussed above, a key feature of the core peptides of the invention is their ability to form intermolecular hydrogen-bonds or salt bridges when arranged in an antiparallel fashion. Thus, in a preferred embodiment of the invention, linkers of sufficient length and flexibility are used so as to permit the helical segments (HH) of structure (II) to align in an antiparallel fashion and form intermolecular hydrogen-bonds or salt bridges in the presence of lipids. Linkers of sufficient length and flexibility include, but are not limited to, Pro (P), Gly (G), Cys-Cys.

Alternatively, as the native apolipoproteins permit cooperative binding between antiparallel helical segments, peptide linkers which correspond in primary sequence to the peptide segments connecting adjacent helices of the native apolipoproteins, including, for example, ApoA-I, ApoA-II, ApoA-IV, ApoC-I, ApoC-II, ApoC-III, ApoD, ApoE and ApoJ can be conveniently used to link the core peptides. These sequences are well known in the art (see, e.g., Rosseneu et al., "Analysis of the Primary and of the Secondary Structure of the Apolipoproteins," In: Structure and Function of Lipoproteins, Ch. 6, 159–183, CRC Press, Inc., 1992).

Other linkers which permit the formation of intermolecular hydrogen bonds or salt bridges between tandem repeats of antiparallel helical segments include peptide reverse turns such as β-turns and γ-turns. Generally, reverse turns are segments of peptide that reverse the direction of the polypeptide chain so as to allow a single polypeptide chain to adopt regions of antiparallel β-sheet or antiparallel α-helical structure. β-turns generally are composed of four amino acid residues and γ-turns are generally composed of three amino acid residues.

The conformations and sequences of many peptide β-turns have been well-described in the art and include, by way of example and not limitation, type-I, type-I', type-II, type-II', type-III, type-III', type-IV, type-V, type-V', type-VIa, type-VIb, type-VII and type-VIII (see, Richardson, 1981, Adv. Protein Chem. 34:167–339; Rose et al., 1985, Adv. Protein Chem. 37:1–109; Wilmot et al., 1988, J. Mol. Biol. 203:221–232; Sibanda et al., 1989, J. Mol. Biol. 206:759–777; Tramontano et al., 1989, Proteins: Struct. Funct. Genet. 6:382–394).

The specific conformations of short peptide turns such as β-turns depend primarily on the positions of certain amino acid residues in the turn (usually Gly, Asn or Pro). Generally, the type-I β-turn is compatible with any amino acid residue at positions 1 through 4 of the turn, except that Pro cannot occur at position 3. Gly predominates at position 4 and Pro predominates at position 2 of both type-I and type-II turns. Asp, Asn, Ser and Cys residues frequently occur at position 1, where their side chains often hydrogen-bond to the NH of residue 3.

In type-II turns, Gly and Asn occur most frequently at position 3, as they adopt the required backbone angles most easily. Ideally, type-I' turns have Gly at positions 2 and 3, and type-II' turns have Gly at position 2. Type-III turns generally can have most amino acid residues, but type-III' turns usually require Gly at positions 2 and 3. Type-VIa and VIb turns generally have a cis peptide bond and Pro as an internal residue. For a review of the different types and sequences of β-turns in proteins and peptides the reader is referred to Wilmot et al., 1988, J. Mol. Biol. 203:221–232.

The conformation and sequences of many peptide γ-turns have also been well-described in the art (see, e.g., Rose et al., 1985, Adv. Protein Chem. 37:1–109; Wilmer-White et al., 1987, Trends Biochem. Sci. 12:189–192; Wilmot et al., 1988, J. Mol. Biol. 203:221–232; Sibanda et al., 1989, J. Mol. Biol. 206:759–777; Tramontano et al., 1989, Proteins: Struct. Funct. Genet. 6:382–394). All of these types of β-turns and γ-turn structures and their corresponding sequences, as well as later discovered peptide β-turns and γ-turn structures and sequences, are specifically contemplated by the invention.

While structure (I), (II) and (III) contains 22 specified amino acid residue positions, it is to be understood that the core peptides of the invention can contain fewer than 22 amino acid residues. Indeed, truncated or internally deleted forms of structure (I), (II) and (III) containing as few as 18 or even 15 amino acid residues that substantially retain the overall characteristics and properties of the amphipathic helix formed by the core peptides of structure (I), (II) and (III) are considered to be within the scope of the present invention.

Truncated forms of the peptides of structure (I) are obtained by deleting one or more amino acids from the N- and/or C-terminus of structure (I), (II) and (III). Internally deleted forms of structure (I), (II) and (III) are obtained by deleting one or more amino acids from internal positions within the peptide of structure (I), (II) and (III). The internal amino acid residues deleted may or may not be consecutive residues.

Those of skill in the art will recognize that deleting an internal amino acid residue from a core peptide of structure (I), (II) and (III) will cause the plane of the hydrophilic-hydrophobic interface of the helix to rotate by 100° at the point of the deletion. As such rotations can significantly alter the amphipathic properties of the resultant helix, in a preferred embodiment of the invention amino acid residues are deleted so as to substantially retain the alignment of the plane of the hydrophilic-hydrophobic interface along the entire long axis of the helix.

This can be conveniently achieved by deleting a sufficient number of consecutive or non-consecutive amino acid residues such that one complete helical turn is deleted. An idealized α-helix contains 3.6 residues per turn. Thus, in a preferred embodiment, groups of 3–4 consecutive or non-consecutive amino acid residues are deleted. Whether 3 amino acids or 4 amino acids are deleted will depend upon the position within the helix of the first residue to be deleted. Determining the appropriate number of consecutive or non-consecutive amino acid residues that constitute one complete helical turn from any particular starting point within an amphipathic helix is well within the capabilities of those of skill in the art.

Due to the surmised importance of the basic cluster at the C-terminus of the core peptides of structure (I), (II) and (III) in stabilizing the helix and the importance of the hydrophobic cluster in effecting lipid binding and LCAT activation, in preferred embodiments of the invention, residues comprising the basic and hydrophobic clusters are not deleted. Thus, in preferred embodiments, residues 19, 20 and 22 (basic cluster) and residues 3, 6, 9 and 10 (hydrophobic cluster) are not deleted.

The core peptides of structure (I), (II) and (III) can also be extended at one or both termini or internally with additional amino acid residues that do not substantially interfere with, and in some embodiments even enhance, the structural and/or functional properties of the peptides. Indeed, extended core peptides containing as many as 23, 25, 26, 29 or even more amino acid residues are considered to be within the scope of the present invention. Preferably, such extended peptides will substantially retain the net amphipathicity and other properties of the peptides of structure (I), (II) and (III). Of course, it will be recognized that adding amino acids internally will rotate the plane of the hydrophobic-hydrophilic interface at the point of the insertion in a manner similar to that described above for internal deletions. Thus, the considerations discussed above in connection with internal deletions apply to internal additions, as well.

In one embodiment, the core peptides are extended at the N- and/or C-terminus by least one helical turn. Preferably, such extensions will stabilize the helical secondary structure in the presence of lipids, such as the end-cap amino acids and segments previously described.

In a particularly preferred embodiment, the core peptide of structure (I), (II) and (III) is extended at the C-terminus by a single basic amino acid residue, preferably Lys (K).

5.1.3. PREFERRED EMBODIMENETS

The ApoA-I agonists encoded by the nucleotide sequences of the present invention can be further defined by way of preferred embodiments.

In one preferred embodiment, the nucleotide sequences of the invention encode ApoA-I agonists composed of core peptides of structure (I) containing 22 amino acid residues in which:

$X_1$ is Pro (P), Gly (G) or Ala (A);
$X_2$ is Val (V) or Leu (L);
$X_3$ is Leu (L);
$X_4$ is Asp (D) or Glu (E);
$X_5$ is Leu (L) or Phe (F);
$X_6$ is Leu (L) or Phe (F);
$X_7$ is Lys (K) or Arg (R);
$X_8$ is Glu (E);
$X_9$ is Leu (L);
$X_{10}$ is Leu (L) or Trp (W);
$X_{11}$ is Asn (N) or Gln (Q);
$X_{12}$ is Glu (E);
$X_{13}$ is Leu (L);
$X_{14}$ is Leu (L) or Trp (W);

$X_{15}$ is Glu (E);
$X_{16}$ is Ala (A) or Trp (W);
$X_{17}$ is Leu (L);
one of $X_{18}$ or $X_{19}$ is Gln (Q) and the other is Lys (K);
$X_{20}$ is Lys (K);
$X_{21}$ is Leu (L); and
$X_{22}$ is Lys (K).

In yet another preferred embodiment, the nucleotide sequences of the present invention encode ApoA-I agonists composed of core peptides of structure (I) containing 22 amino acid residues in which:
$X_1$ is Pro (P), Gly (G) or Ala (A);
$X_2$ is Val (V);
$X_3$ is Leu (L);
$X_4$ is Asp (D) or Glu (E);
$X_5$ is Leu (L) or Phe (F);
$X_6$ is Phe (F);
$X_7$ is Arg (R);
$X_8$ is Glu (E);
$X_9$ is Leu (L);
$X_{10}$ is Leu (L) or Trp (W);
$X_{11}$ is Asn (N);
$X_{12}$ is Glu (E);
$X_{13}$ is Gly (G);
$X_{14}$ is Leu (L);
$X_{15}$ is Glu (E);
$X_{16}$ is Ala (A) or Trp (W);
$X_{17}$ is Leu (L);
$X_{18}$ is Lys (K);
$X_{19}$ is Gln (Q);
$X_{20}$ is Lys (K);
$X_{21}$ is Leu (L); and
$X_{22}$ is Lys (K).

Particularly preferred nucleotide sequences according to this aspect of the invention are those that encode core peptides selected from the group consisting of:

```
peptide 3

PVLDLFRELLNEGLEALKQKLK;    (SEQ ID NO: 3)

peptide 13

GVLDLFRELLNEGLEALKQKLK;    (SEQ ID NO: 13)

peptide 138

PVLDLFRELLNEGLEWLKQKLK;    (SEQ ID NO: 138)

peptide 139

PVLDLFRELWNEGLEALKQKLK;    (SEQ ID NO: 139)

peptide 141

PVLDFFRELLNEGLEALKQKLK;    (SEQ ID NO: 141)

peptide 142

PVLELFRELLNEGLEALKQKLK.    (SEQ ID NO: 142)
```

In still another preferred embodiment, the nucleotide sequences encode ApoA-I agonists which are 22-amino acid residue peptides according to structure (I), in which $X_9$ is Gly (G) and each of $X_{10}$, $X_{13}$, $X_{14}$, $X_{16}$ and $X_{17}$ is other than Gly (G). A particularly preferred ApoA-I agonist according to this aspect of the invention is peptide 20:

```
PVLDLFREGLNELLEALKQKLK.    (SEQ ID NO: 20)
```

In still another preferred embodiment, the nucleotide sequences encode ApoA-I agonists which are 22-amino acid residue peptides according to structure (I), in which $X_{10}$ is Gly (G) and each of $X_9$, $X_{13}$, $X_{14}$, $X_{16}$ and $X_{17}$ is other than Gly (G). A particularly preferred ApoA-I agonist according to this aspect of the invention is peptide 9:

```
PVLDLFRELGNELLEALKQKLK.    (SEQ ID NO: 9)
```

In still another preferred embodiment, the nucleotide sequences encode ApoA-I agonists which are 22-amino acid residue peptides according to structure (I), in which $X_{14}$ is Gly (G) and each of $X_9$, $X_{10}$, $X_{13}$, $X_{16}$ and $X_{17}$ is other than Gly (G). A particularly preferred ApoA-I agonist according to this aspect of the invention is peptide 126:

```
PVLDLFRELLNELGEALKQKLK.    (SEQ ID NO: 26)
```

In still another preferred embodiment, the nucleotide sequences are ApoA-I agonists which are 22-amino acid residue peptides according to structure (I), in which $X_{16}$ is Gly (G) and each of $X_9$, $X_{10}$, $X_{13}$, $X_{14}$ and $X_{17}$ is other than Gly (G). A particularly preferred ApoA-I agonist according to this aspect of the invention is peptide 22:

```
PVLDLFRELLNELLEGLKQKLK.    (SEQ ID NO: 22)
```

In still another preferred embodiment, the nucleotide sequences are ApoA-I agonists which are 22-amino acid residue peptides according to structure (I), in which $X_{17}$ is Gly (G) and each of $X_9$, $X_{10}$, $X_{13}$, $X_{14}$ and $X_{16}$ is other than Gly (G). A particularly preferred ApoA-I agonist according to this aspect of the invention is peptide 12:

```
PVLDLFRELLNELLEAGKQKLK.    (SEQ ID NO: 12)
```

In yet another preferred embodiment, the nucleotide sequences are ApoA-I agonists which are 22-amino acid residue peptides according to structure (I), in which each of $X_9$, $X_{10}$, $X_{13}$, $X_{14}$, $X_{16}$ and $X_{17}$ is other than Gly (G).

Agonists are 22-amino acid residue peptides according to structure (I), in which:
$X_1$ is Pro (P), Gly (G), Ala (A);
$X_2$ is Val (V) or Leu (L);
$X_3$ is Leu (L);
$X_4$ is Asp (D) or Glu (E);
$X_5$ is Leu (L) or Phe (F);
$X_6$ is Leu (L) or Phe (F);
$X_7$ is Arg (R) or Lys (K);
$X_8$ is Glu (E);
$X_9$ is Leu (L);
$X_{10}$ is Leu (L) or Trp (W);
$X_{11}$ is Asn (N) or Gln (Q);
$X_{12}$ is Glu (E);
$X_{13}$ is Leu (L);
$X_{14}$ is Leu (L) or Trp (W);
$X_{15}$ is Glu (E);
$X_{16}$ is Ala (A), Leu (L) or Trp (W);
$X_{17}$ is Leu (L);
one of $X_{18}$ or $X_{19}$ is Gln (Q) and the other is Lys (K);
$X_{20}$ is Lys (K);
$X_{21}$ is Leu (L); and
$X_{22}$ is Lys (K).

In a particularly preferred embodiment according to this aspect of the invention, $X_2$ is Val (V); $X_4$ is Asp (D); $X_5$ is Leu (L); $X_6$ is Phe (F); $X_7$ is Arg R); $X_{10}$ is Leu (L); $X_{11}$ is Asn (N); $X_{13}$ is Leu (L); $X_{14}$ is Leu (L); $X_{16}$ is Ala (A); $X_{17}$ is Leu (L); $X_{18}$ is Lys (K); $X_{19}$ is Gln (Q); $X_{20}$ is Lys (K) and/or $X_{22}$ is Lys (K).

In still another preferred embodiment, the nucleotide sequences encode ApoA-I agonists which are altered or mutated forms of the peptides of structure (I) in which:

$X_1$ is other than Val (V) or Leu (L);
$X_5$ is other than Lys (K), Glu (E) or Trp (W);
$X_6$ is other than Trp (W);
$X_7$ is other than Trp (W) or Leu (L);
$X_8$ is other than Trp (W);
$X_9$ is other than Lys (K) or Trp (W);
$X_{11}$ is other than Trp (W);
$X_{12}$ is other than Trp (W) or Leu (L);
$X_{13}$ is other than Glu (E) or Trp (W);
$X_{15}$ is other than Trp (W); and/or
$X_{21}$ is other than Lys (K).

In yet another preferred embodiment, the nucleotide sequences of the invention encode ApoA-I agonists which are selected from the group of peptides set forth below:

```
peptide 2
GVLDLFRELLNELLEALKQKLKK;    (SEQ ID NO: 2)

peptide 3
PVLDLFRELLNELLEWLKQKLK;     (SEQ ID NO: 3)

peptide 4
PVLDLFRELLNELLEALKQKLK;     (SEQ ID NO: 4)

peptide 7
PVLDLFKELLNELLEALKQKLK;     (SEQ ID NO: 7)

peptide 8
PVLDLFRELLNEGLEALKQKLK;     (SEQ ID NO: 7)

peptide 9
PVLDLFRELGNELLEALKQKLK;     (SEQ ID NO: 8)

peptide 11
PVLDLFKELLQELLEALKQKLK;     (SEQ ID NO: 9)

peptide 12
PVLDLFRELLNELLEAGKQKLK;     (SEQ ID NO: 10)

peptide 13
GVLDLFRELLNEGLEALKQKLK;     (SEQ ID NO: 11)

peptide 15
PVLDLFRELWNELLEALKQKLK;     (SEQ ID NO: 12)

peptide 16
PVLDLLRELLNELLEALKQKLK;     (SEQ ID NO: 13)

peptide 17
PVLELFKELLQELLEALKQKLK;     (SEQ ID NO: 14)

peptide 18
GVLDLFRELLNELLEALKQKLK;     (SEQ ID NO: 15)

peptide 20
PVLDLFREGLNELLEALKQKLK;     (SEQ ID NO: 16)

peptide 22
PVLDLFRELLNELLEGLKQKLK;     (SEQ ID NO: 17)

peptide 23
PLLELFKELLQELLEALKQKLK;     (SEQ ID NO: 18)

peptide 24
PVLDLFRELLNELLEALQKKLK;     (SEQ ID NO: 19)

peptide 26
PVLDLFRELLNELLELLKQKLK;     (SEQ ID NO: 21)

peptide 28
PVLDLFRELLNELWEALKQKLK;     (SEQ ID NO: 23)

peptide 29
AVLDLFRELLNELLEALKQKLK;     (SEQ ID NO: 24)

peptide 123
QVLDLFRELLNELLEALKQKLK;     (SEQ ID NO: 123)

peptide 125
NVLDLFRELLNELLEALKQKLK;     (SEQ ID NO: 124)

peptide 126
PVLDLFRELLNELGEALKQKLK;     (SEQ ID NO: 125)

peptide 127
PVLDLFRELLNELLELLKQKLK;     (SEQ ID NO: 126)

peptide 128
PVLDLFRELLNELLEFLKQKLK;     (SEQ ID NO: 127)

peptide 129
PVLELFNDLLRELLEALQKKLK;     (SEQ ID NO: 128)

peptide 130
PVLELFNDLLRELLEALKQKLK;     (SEQ ID NO: 129)

peptide 131
PVLELFKELLNELLDALRQKLK;     (SEQ ID NO: 130)

peptide 132
PVLDLFRELLENLLEALQKKLK;     (SEQ ID NO: 131)

peptide 133
PVLELFERLLEDLLQALNKKLK;     (SEQ ID NO: 132)

peptide 134
PVLELFERLLEDLLKALNQKLK;     (SEQ ID NO: 133)

peptide 135
DVLDLFRELLNELLEALKQKLK;     (SEQ ID NO: 134)

peptide 136
PALELFKDLLQELLEALKQKLK;     (SEQ ID NO: 135)
```

```
peptide 138

PVLDLFRELLNEGLEWLKQKLK;        (SEQ ID NO: 136)

peptide 139

PVLDLFRELWNEGLEALKQKLK;        (SEQ ID NO: 137)

peptide 141

PVLDFFRELLNEGLEALKQKLK;        (SEQ ID NO: 138)

peptide 142

PVLELFRELLNEGLEALKQKLK.        (SEQ ID NO: 139)
```

In preferred embodiment, the nucleotide sequences encode ApoA-I agonists which are 22 amino acid residue peptides according to structure (II), in which:
$X_1$ is Pro (P), Gly (G), Ala (A) or Asn (N);
$X_2$ is Ala (A), Val (V) or Leu (L);
$X_5$ is Leu (L);
$X_6$ is Phe (F);
$X_{11}$ is Glu (E);
$X_{19}$ is Lys (K);
$X_{20}$ is Lys (K); and/or
$X_{22}$ is Lys (K), and each of $X_3$, $X_4$, $X_7$, $X_8$, $X_9$, $X_{10}$, $X_{12}$, $X_{13}$, $X_{14}$, $X_{15}$, $X_{16}$, $X_{17}$, $X_{18}$ and $X_{21}$ are as previously defined for structure (II).

Particularly preferred ApoA-I agonists according to this aspect of the invention are those in which $X_2$ is Val (V); and/or $X_{18}$ is Gln (Q).

In still another preferred embodiment, the ApoA-I agonists are 22 amino acid residue peptides according to structure (II), in which one of $X_{10}$, $X_{13}$ or $X_{14}$ is Gly (G) and the others of $X_{10}$, $X_{13}$ and $X_{14}$ are other than Gly (G). When $X_{14}$ is Gly (G), $X_7$ is preferably Glu (E).

Particularly preferred nucleotide sequences according to this aspect of the invention encode ApoA-I agonists which are peptides selected from the group consisting of:

```
peptide 148:

PVLELFENLLERLGDALQKKLK;        (SEQ ID NO: 148)

peptide 151:

PVLELFENLGERLLDALQKKLK;        (SEQ ID NO: 151)

peptide 154:

PVLELFENLLERGLDALQKKLK.        (SEQ ID NO: 154)
```

In still another preferred embodiment, the ApoA-I agonists are 22-amino acid residue peptides according to structure (II), in which each of $X_{10}$, $X_{13}$ and $X_{14}$ is other than Gly (G).

In still another preferred embodiment, the nucleotide sequences encode ApoA-I agonists which are altered or mutated forms of the peptides according to structure (II), in which:
$X_4$ is other than Asp (D);
$X_5$ is other than Phe (F);
$X_6$ is other than Trp (W);
$X_7$ is other than Leu (L) or Asp (D);
$X_9$ is other than Gly (G) or Trp (W);
$X_{12}$ is other than Lys (K);
$X_{13}$ is other than Trp (W);
$X_{14}$ is other than Trp (W);
$X_{15}$ is other than Glu (E);
$X_{16}$ is other than Trp (W) or Leu (L); and/or
$X_{17}$ is other than Trp (W).

In still another preferred embodiment, the ApoA-I agonists are 22 amino acid residue peptides according to structure (II), in which when $X_7$ is Leu (L), $X_{10}$ is Trp (W), $X_1$ is other than Gly (G) and/or $X_{14}$ is other than Gly (G). A particularly preferred peptide according to this aspect of the invention is peptide 155 (PVLELFLNLWERLLDALQKKLK; SEQ ID NO: 155).

In still another preferred embodiment, the nucleotide sequences encode ApoA-I agonists which are selected from the group of peptides set forth below:

```
peptide 145:

GVLELFENLLERLLDALQKKLK;        (SEQ ID NO: 145)

peptide 146:

PVLELFENLLERLLDALQKKLK;        (SEQ ID NO: 146)

peptide 147:

PVLELFENLLERLFDALQKKLK;        (SEQ ID NO: 147)

peptide 148:

PVLELFENLLERLGDALQKKLK;        (SEQ ID NO: 148)

peptide 149:

PVLELFENLWERLLDALQKKLK;        (SEQ ID NO: 149)

peptide 150:

PLLELFENLLERLLDALQKKLK;        (SEQ ID NO: 150)

peptide 151:

PVLELFENLGERLLDALQKKLK;        (SEQ ID NO: 151)

peptide 152:

PVFELFENLLERLLDALQKKLK;        (SEQ ID NO: 152)

peptide 153:

AVLELFENLLERLLDALQKKLK;        (SEQ ID NO: 153)

peptide 154:

PVLELFENLLERGLDALQKKLK;        (SEQ ID NO: 154)

peptide 155:

PVLELFLNLWERLLDALQKKLK;        (SEQ ID NO: 155)

peptide 186:

PVLELFEQLLERLLDALQKKLK;        (SEQ ID NO: 186)

peptide 187:

PVLELFENLLERLLDALNKKLK;        (SEQ ID NO: 187)

peptide 188:

PVLELFENLLDRLLDALQKKLK;        (SEQ ID NO: 188)

peptide 189:

DVLELFENLLERLLDALQKKLK.        (SEQ ID NO: 189)
```

In one preferred embodiment, the ApoA-I agonists are 18 amino acid residue peptides according to structure (III).

In another preferred embodiment, the nucleotide sequences encode ApoA-I agonists which are 18 amino acid residue peptides according to structure (III) in which:

$X_2$ is Ala (A), Val (V) or Leu (L);
$X_4$ is Asp (D) or Glu (E);
$X_7$ is Arg (R) or Lys (K);
$X_8$ is Asp (D) or Glu (E);
$X_{11}$ is Glu (E) or Asn (N);
$X_{12}$ is Glu (E);
$X_{14}$ is Arg (R), Lys (K) or Leu (L);
$X_{16}$ is Arg (R) or Lys (K); and/or
$X_{18}$ is Arg (R) or Lys (K) and $X_1$, $X_3$, $X_5$, $X_6$, $X_9$, $X_{10}$, $X_{13}$, $X_{15}$ and $X_{17}$ are as previously defined for structure (III).

In another preferred embodiment, the ApoA-I agonists are 18 amino acid residue peptides according to structure (III), in which when $X_{11}$ is Asn (N), $X_{14}$ is Leu (L) and when $X_{11}$ is other than Asn (N), $X_{14}$ is other than Leu (L). An exemplary particularly preferred embodiment according to this aspect of the invention is the peptide 209 (PVLDLFRELLNELLQKLK; SEQ ID NO: 209).

In still another preferred embodiment, the ApoA-I agonists are altered or mutated forms of the peptides according to structure (III), in which
$X_1$ is other than Asp (D);
$X_9$ is other than Gly (G);
$X_{10}$ is other than Gly (G);
$X_{12}$ is other than Leu (L); and
$X_{13}$ is other than Gly (G).

In still another preferred embodiment, the nucleotide sequences encode ApoA-I agonists which are selected from the group of peptides set forth below:

```
peptide 191   PVLDLLRELLEELKQKLK*;   (SEQ ID NO: 191)
peptide 192   PVLDLFKELLEELKQKLK*;   (SEQ ID NO: 192)
peptide 193   PVLDLFRELLEELKQKLK*;   (SEQ ID NO: 193)
peptide 194   PVLELFRELLEELKQKLK*;   (SEQ ID NO: 194)
peptide 195   PVLELFKELLEELKQKLK*;   (SEQ ID NO: 195)
peptide 196   PVLDLFRELLEELKNKLK*;   (SEQ ID NO: 196)
peptide 197   PLLDLFRELLEELKQKLK*;   (SEQ ID NO: 197)
peptide 198   GVLDLFRELLEELKQKLK*;   (SEQ ID NO: 198)
peptide 199   PVLDLFRELWEELKQKLK*;   (SEQ ID NO: 199)
peptide 200   NVLDLFRELLEELKQKLK*;   (SEQ ID NO: 200)
peptide 201   PLLDLFKELLEELKQKLK*;   (SEQ ID NO: 201)
peptide 202   PALELFKDLLEELRQKLR*;   (SEQ ID NO: 202)
peptide 203   AVLDLFRELLEELKQKLK*;   (SEQ ID NO: 203)
peptide 204   PVLDFFRELLEELKQKLK*;   (SEQ ID NO: 204)
peptide 205   PVLDLFREWLEELKQKLK*;   (SEQ ID NO: 205)
peptide 206   PLLELLKELLEELKQKLK*;   (SEQ ID NO: 206)
peptide 207   PVLELLKELLEELKQKLK*;   (SEQ ID NO: 207)
peptide 208   PALELFKDLLEELRQRLK*;   (SEQ ID NO: 208)
peptide 209   PVLDLFRELLNELLQKLK;    (SEQ ID NO: 209)
peptide 210   PVLDLFRELLEELKQKLK;    (SEQ ID NO: 210)
peptide 213   PALELFKDLLEEFRQRLK*;   (SEQ ID NO: 213)
peptide 215   PVLDLFRELLEEWKQKLK*;   (SEQ ID NO: 215)
peptide 229   PVLELFERLLEDLQKKLK;    (SEQ ID NO: 229)
peptide 230   PVLDLFRELLEKLEQKLK;    (SEQ ID NO: 230)
peptide 231   PLLELFKELLEELKQKLK*.   (SEQ ID NO: 231)
```

In yet another preferred embodiment, the nucleotide sequences of the present invention encode ApoA-I agonists which are multimeric forms according to structure IV in which each HH is independently a peptide according to structure (I), (II) or (III), or any of the preferred peptides according to structure (I), (II) or (III) described herein.

In a final preferred embodiment, the ApoA-I agonists are not any of the peptides listed in Table VIII which are composed of amino acids not genetically encoded or which exhibit an LCAT activation activity of less than 38% as compared with native human ApoA-I.

5.1.4. Analysis of Structure and Function

The structure and function of the core peptides or peptide analogues of the invention, as well as ApoA-I agonists composed of such core peptides, including the multimeric forms described above, can be assayed in order to select active agonists or mimetics of ApoA-I. For example, the core peptides or peptide analogues can be assayed for their ability to form α-helices in the presence of lipids, to bind lipids, to form complexes with lipids, to activate LCAT, to promote cholesterol efflux, etc.

Methods and assays for analyzing the structure and/or function of the peptides are well-known in the art. Preferred methods are provided in the working examples, infra. For example, the circular dichroism (CD) and nuclear magnetic resonance (NMR) assays described in Section 7, infra, can be used to analyze the structure of the peptides or peptide analogues—particularly the degree of helicity in the presence of lipids. The ability to bind lipids can be determined using the fluorescence spectroscopy assay described in Section 7, infra. The ability of the peptides and/or peptide analogues to activate LCAT can be readily determined using the LCAT activation described in Section 8, infra. The in vitro and in vivo assays described in Section 9 and 10, infra, can be used to evaluate the half-life, distribution, cholesterol efflux and effects on RCT.

Generally, core peptides and/or peptide analogues according to the invention which exhibit the properties listed in TABLE VI, infra, are considered to be active.

TABLE VI

PROPERTIES OF ACTIVE PEPTIDES

| PROPERTY | RANGE | PREFERRED RANGE |
|---|---|---|
| % Helicity in the presence of lipids (Ri = 30) (unblocked 22-amino acid residue peptides) | ≧60% | ≧80% |
| % Helicity in the presence of lipids (Ri = 30) (unblocked 18-amino acid residue peptides) | ≧40% | ≧60% |
| % Helicity in the presence of lipids (Ri = 30) (blocked 18-amino acid residue peptides and shorter peptides) | ≧60% | ≧80% |
| Lipid Binding (in the presence of SUVs) | 0.5–10 μM peptide $R_i$ = 1–50 | |
| LCAT activation | ≧38% | ≧80% |

$R_i$ is lipid:peptide molar ratio.

As illustrated in the working examples, infra, core peptides which exhibit a high degree of LCAT activation (≧38%) generally possess significant α-helical structure in the presence of lipidic small unilamellar vesicles (SUVs) (≧60% helical structure in the case of unblocked peptides containing 22 or more amino acid residues and blocked peptides containing 18 or fewer amino acid residues; ≧40% helical structure in the case of unblocked peptides containing 18 or fewer amino acids), and those peptides which exhibit little or no LCAT activation possess little α-helical structure. However, in certain instances, peptides which exhibit significant helical structure in the presence of lipids do not effect significant LCAT.

Similarly, while core peptides that exhibit significant LCAT activation typically bind lipids, in certain instances peptides which exhibit lipid binding do not effect significant LCAT activation.

As a consequence, it will be recognized by those of skill in the art that while the ability of the core peptides described herein to form α-helices (in the presence of lipids) and to bind lipids is critical for activity, in many instances these properties may not be sufficient. Thus, in a preferred embodiment core peptides of the invention are subjected to a series of screens to select for core peptides exhibiting significant pharmacological activity.

In a first step, a core peptide is screened for its ability to form an α-helix in the presence of lipids using the CD assay described in Section 7, infra. Those peptides which are at least 40% helical or 60% helical in the presence of lipids (at a conc. of about 5 μM and a lipid:peptide molar ratio of about 30) are then screened for their ability to bind lipids using the fluorescence assay described in Section 7, infra. Of course, only those core peptides which contain a fluorescent Trp (W) residue are screened for lipid binding via fluorescence. However, for peptides which do not contain fluorescent residues, binding to lipids is obvious when helicity increases in the presence of lipids.

Core peptides which exhibit lipid binding in the presence of SUVs (0.5–10 μM peptide; lipid:peptide molar ratio in the range of 1 to 50) are then screened for pharmacological activity. Of course, the pharmacological activity screened for will depend upon the desired use of the ApoA-I agonists. In a preferred embodiment, the core peptides are screened for their ability to activate LCAT, as peptides which activate LCAT are particularly useful in the methods described herein. Core peptides which exhibit at least about 38% LCAT activation as compared with native human ApoA-I (as determined using the LCAT activation assay described in Section 8, infra), are preferred, with core peptides exhibiting 50%, 60%, 70%, 80% or even 90% or more being particularly preferred.

5.2. DNA Vectors and Cassettes Encoding ApoA-1

In accordance with the present invention the nucleotide sequences encoding native ApoA-I, modified forms of ApoA-I or peptides with ApoA-I activity, including ApoA-I agonists and superagonists, are inserted into a cassette or an appropriate expression vehicle, i.e., a vector which contains the necessary elements for the transcription and translation of the inserted coding sequence, or in the case of an RNA viral vector, the necessary elements for replication and translation. The nucleotide sequences of the present invention may be administered as "naked" DNA constructs for both ex vivo and in vivo gene therapy protocols. Naked DNA plasmids encoding the ApoA-I peptides and agonists may be injected into a subject and successfully taken up by cells and expressed as peptides (Felgner et al. U.S. Pat. No. 5,580,859, incorporated herein by reference in its entirety).

"Naked" DNA may also be administered in complexes with nonlipid cationic polymers or in complexes with liposomes to enhance cellular uptake.

In another embodiment of the present invention the expression vehicle is transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y.).

In accordance with the present invention, the DNA cassettes contain nucleotide sequences encoding the prepro form and the proform of ApoA-I to ensure that teh ApoA-I peptides are correctly processes and secreted from the host cell. The preproform of ApoA-I contains an 18aa leader or signal sequence at teh amino terminus cleaved upon secretion of the ProApoA-I from the host cell. The leader sequence of ApoA-I is of the standard length and hydrophobicity (see, Davis et al. 1980 Nature 283:433–438) and ends in an amino acid with a small side chain, e.g., alanine. By way of example and not by limitation, the following leader sequences may be incorporated into the DNA cassettes and vectors of the present invention: 5'MKAAVLT-LAVLFLTGSQA3' (SEQ ID NO.: 270) or 5'MKAAVLA-VALVFLTGCQA3' (SEQ ID NO.: 271). Any sequence which results in the secretion of the peptide from the host cell may be used in accordance with the present invention.

The proform of ApoA-I, ProApoA-I contains a six-amino acid amino-terminal extension with the sequence: R-H-F-W-Q-Q (SEQ ID NO.: 272) or X-E-F-X-Q-Q (SEQ ID NO.: 273). The extracellular cleavage of the prosegment by a specific protease generates the plasma form of ApoA-I. In accordance with the present invention, the sequences encoding the six-amino acid extension my be incorporated into the DNA cassettes and vectors of the invention to ensure that the encoded ApoA-I peptides are correctly processed once they are secreted from the host cell.

To increase efficiency of production, the polynucleotide can be designed to encode multiple units of the peptide separated by enzymatic cleavage sites—either homopolymers (repeating peptide units) or heteropolymers (different peptides strung together) can be engineered in this way. The resulting polypeptide can be cleaved (e.g., by treatment with the appropriate enzyme) in order to recover the peptide units. This can increase the yield of peptides driven by a single promoter. In a preferred embodiment, a polycistronic polynucleotide can be designed so that a single mRNA is transcribed which encodes multiple peptides (i.e., homopolymers or heteropolymers) each coding region operatively linked to a cap-independent translation control sequence; e.g., an internal ribosome entry site (IRES), such as the sequences described by Pelletier et al. 1988 Nature 334:320–325. In a preferred embodiment, the IRES is derived from the 5' noncoding region of the human immunoglobulin heavy-chain-binding protein (BiP) mRNA (Macejak et al. 1991 Nature 353: 90–94). Preferably, the IRES region is derived from a picornavirus IRES region sequence; the IRES sequence is selected from the group consisting of an enterovirus, rhinovirus, cardiovirus, and aphthovirus IRES sequence; a hepatitis A virus IRES sequence, a hepatitis B virus sequence and a hepatitis C virus IRES sequence. When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

A variety of host-expression vector systems may be utilized to express the peptides described herein. Any host-expression system may be used in accordance with the present invention that the system (1) expresses the ApoA-I peptides of the invention; (2) utilizes expression control elements (e.g., promoters and enhancers) that are operable in mammalian cells; and (3) expresses the ApoA-I nucleotide sequences at high copy numbers. In a preferred embodiment, any expression system which result in an increased copy number of the nucleotide sequences encoding ApoA-I peptides and agonists in human cells when engineered using ex vivo or in vivo gene therapy protocols. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of transcription and translation elements operable in mammalian, preferably human, host cell systems, including constitutive and inducible promoters, may be used in the expression vector, in a preferred embodiment, the expression elements incorporated into the vectors and cassettes of the present invention are the cis- and trans-regulatory elements which regulate expression of the native ApoA-I gene. In particular, transcriptional regulatory and enhancer elements are found in the nucleotide sequences located -222 to -110 upstream of the ApoA-I gene, for example, the binding site for ApoA-I regulatory protein-1 (ARP-1) a member of the steroid hormone receptor superfamily is within the liver-specific transcriptional enhancer, located -222 to -110 DNA region upstream of the ApoA-I gene. The consensus sequence for ARP-1 binding is 5'TGAACCCTTGACCCCT3' (SEQ ID NO:274) (see, Ladias et al. 1991 Science 251:561–565). Additional ApoA-I transcriptional regulation sequences and enhancer elements are disclosed in Sorci-Thomas et al. 1991 *Journal of Biol. Chem.* 266: 18045–18050, Dai et al. 1990 *Eur. J. Biochem.* 190:305–310, Rottman et al. 1991 *Molecular and Cell Biology* 11:3814–3820.

When cloning in bacterial, plant, insect or mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In mammalian host cells, a number of viral-based expression systems may be utilized. In cases where an adenovirus is used as an expression vector, the ApoA-I peptide coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing an ApoA-I peptide in infected hosts. (e.g., See Logan and Shenk, 1984, Proc. Natl. Acad. Sci. USA 81, 3655–3659). Specific initiation signals may also be required for efficient translation of inserted ApoA-I peptide coding sequences. These signals include the ATG initiation codon and adjacent sequences. In cases where an entire ApoA-I, including its own initiation codon and adjacent sequences, is inserted into the appropriate expression vector, no additional translational control signals may be needed. However, in cases where only a portion of the ApoA-I peptide coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

Other expression systems for producing the peptides of the invention will be apparent to those having skill in the art.

5.2.1. Viral Vectors Encoding ApoA-I

In accordance with the present invention, the nucleotide sequences and DNA cassettes described above encoding ApoA-I agonists or peptides with ApoA-I activity may be engineered into appropriate viral vectors. The viral vectors described herein are particularly useful for in vivo genetic approaches to supply the nucleotide sequences of the present invention. In accordance with the present invention, the viral vectors engineered to express native ApoA-I are not encompassed by the present invention.

For the practice of the present invention, viruses which display a suitable tropism for disease target cells, e.g., liver cells, cells of large and small intestine, endothelial cells, etc., or which are genetically engineered to display a suitable tropism for the target cells, are genetically engineered to contain nucleotide sequences that encode ApoA-I agonist peptides. For the practice of the present invention, viruses which display a tropism for liver cells and cells of the small and large intestine are a particularly preferred embodiment of the present invention. Viral vectors which can be used in accordance with the invention include, but are not limited to hepadnavirus, adenovirus, adeno-associated virus, herpes virus, retrovirus, parvovirus, vaccinia virus, etc.

In a specific embodiment, attenuated viruses, such as hepadnaviruses, which have a natural tropism for hepatocytes, may be engineered and used for gene therapy in accordance with the present invention. Hepadnaviruses may be engineered to deliver the nucleotide sequences encoding native ApoA-I and ApoA-I to the cells and organs where it is naturally expressed. There are regions of the hepadnavirus genome which can serve as regions to insert foreign DNA sequences. In particular, sequences encoding the hepatitis B virus (HBV) surface antigen proteins, pre-S1 and pre-S2, can be targeted for the insertion of DNA sequences encoding ApoA-I peptides and agonists. For example, nucleotide sequences encoding the ApoA-I peptides may be insert downstream of the TATA-like sequence (at position 278) which is the promoter for the pre-S1 mRNA or may be inserted downstream of the SV40 like promoter (at position 3166) which is the promoter for the pre-S2 mRNA. The insertion of foreign coding sequences downstream of these regions places them under the regulation of viral gene expression without disruption of other essential viral activities.

Adenoviruses are other viral vectors that can be used in gene therapy. Adenoviruses are especially attractive vehicles for delivering genes to liver and respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current opinion in Genetics and Development 3:499–503 present a review of adenovirus-based gene therapy. In addition, Gerard et al., 1996, Current Opin. in Lipidology 7:105–111 describes adenovirus-mediated gene transfer as a means of delivering ApoA-I. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest, 91:225–234. Adeno-associated virus (AAV) has also been proposed for use in gene therapy (Walsh et al., 1993, Proc. Soc. Exp. Biol. Med. 204:289–300.

For example, the cassettes encoding heteropolymers of ApoA-I peptides (i.e., heteropolymers containing ApoA-I agonists and superagonists separated by enzyme cleavage sites or by IRES sequences) may be advantageously engineered into adenoviruses. Gene sequences required for regulating adenoviral gene expression which can be manipulated in accordance with the invention include region E1, region E3, or between the right ITR and region E4. These regions may be replaced with the TRE of interest and incorporated into viral particles by packaging of the recombinant adenoviral genome.

There are three regions of adenovirus which would be preferred sites for the insertion of foreign DNA sequences for the purpose of engineering recombinant viruses. These regions include (a) the EIA region and the major late promoter (MLP); (2) the MLP, together with the tripartite leader; and (3) the replacement of the E3 region. The E3 region has been shown to be dispensable for viral packaging in tissue culture. Chimeric viruses resulting from insertion of foreign DNA sequences in the EIA and MLP regions may be rescued by growth in 293 cells or be co-transfection with a helper virus providing the missing function in trans.

The herpes simplex virus which displays a natural tropism for the nervous system, may be modified to infect hepatocytes or endothelial cells and to contain desired nucleotide sequences that encode ApoA-I peptides. For example, the cassettes encoding heteropolymers of ApoA-I peptides may be advantageously engineered downstream of an early promoter region of HSV such as the ICP4 gene sequences or the VP16 gene sequences in order to enhance expression of these sequences. Several structural genes of HSV can be targeted for the insertion of foreign DNA sequences for the purpose of engineering recombinant viruses. For example, the nucleotide sequences encoding the structural glycoproteins, gB, gD and gH can serve as regions to insert foreign DNA sequences. However, those gene products which have been replaced and/or disrupted would be supplied in trans, either by vector and/or expressed by host cells in order to produce virus stocks of the resulting recombinant viruses.

Human retroviruses may be used to, e.g. HTLV-1 and HTLV-2 or animal retroviruses which display a tropism for human lymphocytes, e.g., Bovine leukemia virus, Moloney murine leukemia virus, Rous-associated virus, and feline leukemia virus, may be used to target liver cells. Sequences required for retroviral replication are located in the LTR, therefore, foreign DNA sequences, i.e., coding sequences of the ApoA-I peptide of interest may be inserted downstream. In retrovirus-infected cells, viral transcription occurs from the integrated viral DNAs, the provirus, which represents a transcriptional unit that contains its own regulatory sequences. Expression of the provirus depends on (1) the site into which the provirus has integrated; (2) the physiological state of the cell; and (3) the viral LTR. The expression of the provirus depends almost entirely on host-encoded enzymes.

The viral LTR is derived from three segments of the viral RNA: the R, U5 and U3 sequences. The R or redundant sequence is a short segment (30 to 60 nucleotides) that is present twice in the viral RNA, at the extreme left (5') and right (3') termini. The U5 sequences are present at the 5' end of the viral RNA. The U3 sequences are located upstream from the R sequences and have the most variation in size (0.2 to 1.2 kb) and sequence homology.

Viral specific regulation of expression depends principally on the long terminal repeat (LTR) which contains signals for enhancement, promotion, initiation and polyadenylation of RNA synthesis. Transcription is initiated at the left end of the R sequences in the left-hand LTR. Viral transcription is catalyzed by a cellular type II RNA polymerase and is polyadenylated post-transcriptionally near the right hand end of the right LTR. The U3 regions of all LTRs possess CCAAT and TATAA boxes. Enhancer function has been localized to a repeat sequence of variable length (72 to 101 nucleotides) that is found in U3, upstream from the promoter domain. Sequences in U3 of the Moloney murine leukemia virus (MMTV) LTR have also been found to be responsible for the enhanced level of virus expression in response to glucocorticoid treatment of MMTV-infected cells.

Murine parvovirus (MVM) which displays a natural tropism for human T cells, may be modified to infect hepatocytes or the endothelial cells of the gut. In the case of MVM, the major cis-acting factors that are essential for the first steps in viral DNA replication are found upstream of the "early" promoter, P4 (Cotmore et. al., 1992, Virology 190: 365–377). The early promoter is the initiating promoter for viral transcription, and its TATAA box is located 4 map units from the left end of the MVM genome, at around nucleotide 150. The essential cis-acting functions for the origin of MVM DNA replication are also found in this region. The insertion of foreign DNA sequences such as the coding sequences for the ApoA-1 peptides just downstream of this region places them under the regulation of viral gene expression without disruption of other essential viral activities, i.e., DNA replication.

Vesicular stomatitis virus (VSV), the prototypic rhabdovirus, can be used in gene therapy to express the ApoA-I peptides of the invention in mammalian cells. VSV is the simplest of enveloped animal viruses, grows to very high titers and can be prepared in large quantities. Foreign glycoproteins may be incorporated into the VSV G envelope protein to target the viral vector to liver cells or cells of the small and large intestine. The VSV G gene is large enough to accommodate nucleotide sequences encoding the ApoA-I peptides of the invention. (See Schnell et al., 1996, Proc. Natl. Acad. Sci. USA 93:11359–11365).

Alphavirus-based expression vectors, a prototype of enveloped positive-strand RNA viruses, can also be engineered to mediate efficient expression of the nucleotides encoding the ApoA-I peptides of the invention. Although normally cytocidal for vertebrate cells, variants of alphavirus with adaptive mutations allow noncytopathic replication of alphaviral vectors. Nucleotide sequences encoding the ApoA-I peptides may be engineered into the structural gene of the replication defective alphavirus genome. Defective helper RNAs containing the cis-acting sequences required for replication as well as the RNA promoter to package the replication defective alphaviral vector (Frolov et al., 1996, Proc. Natl. Acad. Sci. USA 93:11371–11377). In addition to VSV and alphavirus and viruses, including influenza, rhababviruses, parainfluenza virus and bunya virus, may also be engineered using similar techniques for the delivery and expression of the nucleotide sequences encoding the ApoA-I peptides of the present invention.

The viral vectors described above are by way of example, and not by way of limitation of the present invention. Any viral vector which may be genetically engineered to safely administer the nucleotide sequences encoding ApoA-I peptides and agonists to the target cells may be used in accordance with the present invention.

5.2.2. Host Cells Expressing APoA-I

The present invention encompasses the expression of ApoA-I and peptides exhibiting ApoA-1 activity as described above, in animal cells or cell lines, preferably human cell or cell lines which may then be administered in vivo. The host cells which may be used in accordance with the invention to express ApoA-I and peptides exhibiting ApoA-I activity, including, but are not limited to, fibroblasts, Caco-2 cells, epithelial cells, endothelial cells, muscle cells, hepatocytes, cells isolated from large and small intestine etc. In a preferred embodiment of the invention, hepatocytes and cells isolated from the small intestine are used as host cells to express ApoA-I and peptides exhibiting ApoA-I activity. The host cells of the present invention also have utility as a model system to further understand the role of ApoAI in lipid metabolism.

The host cells of the present invention also have utility as a model system to further understand the role of ApoA-I in lipid metabolism.

In one embodiment of the present invention, host cells are obtained from the recipient, that is the individual who is to receive the transduced cells, or from a donor. Examples of cells which may be genetically engineered in accordance with the present invention, include, but are not limited to, hepatocytes, gall bladder cells, cells of the small intestine, epithelial cells, and endothelial cells, including cells isolated from small and large blood vessels. The isolate cells may be transfected or transduced with the DNA and viral vectors described herein. The transduced cells may subsequently be grafted or transplanted into the recipient.

In another embodiment of the present invention, both transient and permanent recombinant cell lines may be engineered in which the native apolipoprotein A, or any other apolipoprotein, coding sequence is replaced by the coding sequence for a modified preproapolipoprotein A-I, a modified proapolipoprotein A-I, a modified ApoA-I or an Apo A-I agonist.

A host cell strain may be chosen which modulates the expression of the inserted sequences, or modifies and processes the gene product in the specific fashion desired. Such modification (e.g., glycosylation) and processing (e.g. cleavage) of protein products may be important for the function of the protein. Different host cells have characteristic and specific mechanisms for the post-translational processing and modification of proteins and gene products. Appropriate cell lines or host systems can be chosen to ensure the correct modification of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38 cell lines.

For long term, high-yield production of native ApoA-I or peptides having ApoA-I agonist activity mammalian host cells stably expressing these peptides may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines. This method may advantageously be used to engineer cell lines which express the ApoA-I and ApoA-I peptide gene products. Such cell lines would be particularly useful in screening and evaluation of compounds that affect the endogenous activity of the ApoA-I and ApoA-I peptide gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

For example, the cassettes encoding heteropolymers of ApoA-I peptides may be advantageously engineered into adenoviruses as described in detail above.

5.2.3. Transgenis Animals Expressing APOA-I

The invention also encompasses the expression of the ApoA-I nucleotide sequences of the present invention transgenic animals as a model system to further understand the role of ApoA-I in lipid metabolism in addition to having utility for gene therapy. Animals of any species, including, but not limited to, mice, rats, rabbits, guinea pigs, micropigs, goats, and non-human primates, e.g., baboons, monkeys, and chimpanzees may be used to generate ApoA-I transgenic animals.

Any technique known in the art may be used to introduce the ApoA-I transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the ApoA-I transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the ApoA-I transgene be integrated into the chromosomal site of the endogenous ApoA-I gene, gene targeting is preferred. Briefly, when such a technique is to be utilized, vectors containing some nucleotide sequences homologous to the endogenous ApoA-I gene are designed for the purpose of integrating, via homologous recombination with chromosomal sequences, into and disrupting the function of the nucleotide sequence of the endogenous ApoA-I gene. The transgene may also be selectively introduced into a particular cell type, thus inactivating the endogenous ApoA-I gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

5.3. Gene Therapy Approaches to Deliver ApoA-I Peptides

Gene therapy approaches may also be used in accordance with the present invention to deliver nucleotide sequences encoding native ApoA-I or ApoA-I peptides.

The gene therapy approaches of the present invention can be used to treat any disorder in animals, especially mammals, including humans, for which increasing serum HDL concentration, activating LCAT, and promoting cholesterol efflux and RCT is beneficial. Such conditions include, but are not limited to hyperlipidemia, and especially hypercholesteremia, and cardiovascular disease such as atherosclerosis (including prevention of atherosclerosis and treatment of existing disease); restenosis (e.g., preventing or treating atherosclerotic plaques which develop as a consequence of medical procedures such as balloon angioplasty); and other disorders, such as endotoxemia which often results in septic shock (e.g., Gouni et al., 1993, J. Lipid Research 94:139–146; Levine, WO96/04914).

The gene therapy approaches of the present invention can be used alone or in combination therapy with other drugs used to treat the foregoing conditions. Such therapies include, but are not limited to simultaneous or sequential administration of the drugs involved.

5.3.1. Gene Replacement Therapy

With respect to an increase in the level of normal ApoA-I peptide expression and/or ApoA-I peptide product activity, ApoA-I peptide nucleic acid sequences, described, above, in Section 5.1, can, for example, be utilized for the treatment of dislipidemic or hyperlipidemic disorders Such treatment can be administered, for example, in the form of gene replacement therapy. Specifically, one or more copies of a normal ApoA-I peptide or a portion of the ApoA-I peptide that directs the production of a ApoA-I peptide product exhibiting normal ApoA-I peptide function, may be inserted into the appropriate cells within a patient, using vectors that include, but are not limited to adenovirus, adeno-associated virus, and retrovirus vectors, in addition to other particles that introduce DNA into cells, such as liposomes.

Because the ApoA-I protein is expressed in the liver, such gene replacement therapy techniques should be capable delivering ApoA-I peptide sequences to these cell types within patients.

In another embodiment, techniques for delivery involve direct administration of such ApoA-I peptide sequences to the site of the cells in which the ApoA-I peptide sequences are to be expressed.

Additional methods that may be utilized to increase the overall level of ApoA-I peptide expression and/or ApoA-I peptide product activity include the introduction of appropriate ApoA-I expressing cells, preferably autologous cells, into a patient at positions and in numbers that are sufficient to ameliorate the symptoms of a hyperlipidemia disorder. Such cells may be either recombinant or non-recombinant.

Among the cells that can be administered to increase the overall level of ApoA-I peptide expression in a patient are normal cells, preferably hepatocytes, that express the ApoA-I peptide.

Alternatively, cells, preferably autologous cells, can be engineered to express ApoA-I peptide sequences, and may then be introduced into a patient in positions appropriate for the amelioration of the symptoms of a dyslipidemia disorder. Alternately, cells that express an unimpaired ApoA-I peptide and that are from a MHC matched individual can be utilized, and may include, for example, hepatocytes. The expression of the ApoA-I peptide sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349 incorporated herein by reference in its entirety.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

5.3.2. Delivery of Nucleic Acids In Vivo

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient for cell replacement therapy. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the cell or nucleus, e.g., by administering it in linkage to a ligand subject to receptor-mediated endocytosis (see e.g., Wu and Wu, 1987, J. Biol. Chem. 262: 4429–4432) (which can be used to target cell types specifically expressing the receptors), etc. In a specific embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). In another embodiment, a nucleic acid-ligand complex can be formed in which the ligand comprises a fusogenic viral peptide to disrupt endosomes, allowing the nucleic acid to avoid lysosomal degradation. Alternatively, the nucleic acid can be introduced intracellularly and incorporated within host cell DNA for expression, by homologous recombination (Koller & Smithies, 1989, Proc. Natl. Acad. Sci. USA 86:8932–8935; Zijlstra et al., 1989, Nature 342:435–438).

In yet another embodiment, the nucleic acid may be administered in vivo by a time controlled release device. The nucleic acid may also be administered in vivo by a device which contains cells expressing the ApoA-I peptides and agonists of the present invention, protecting them from rejection by the recipient or host. In accordance with this device, the proteins and peptides may diffuse through a permeable membrane which has a molecular weight cut off of approximately 3,500 to 50,000 daltons.

One strategy for targeting DNA or viral vectors hepatocytes can be based on the presence of the asialoglycoprotein (ASPG) receptor on hepatocytes. This receptor is specifically expressed on the cell surface of hepatocytes. Asialoglycopeptide-protein conjugates and asialoglycopeptide-coated vesicles have been used to specifically deliver to a variety of bioactive agents to the liver in vivo. Aitie et al., 1980, Proc. Natl. Acad. Sci. 27:5923–5927; Hildenbrandt et al., 1980, BBA 631:499–502.

Another strategy to targeting delivery of nucleotide sequences to hepatocytes is to genetically modify viral vectors, i.e. adenoviruses and retroviruses to express ligands for the ASPG receptors. Internalization of virus occurs through the specific interaction of the viral envelope with a cell surface receptor, followed by receptor-mediated endocytosis of the virus/receptor complex. The viral vectors which may be used in accordance with the present invention are discussed above in Section 5.2.2.

5.3.3. Delivery of Nucleic Acids Ex Vivo

Another approach to gene therapy, for use in the cell replacement therapy of the invention, involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler & Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells (e.g., keratinocytes) may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

In an embodiment in which recombinant cells are used in gene therapy, nucleotides which encode a gene or promoter suppressor are introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

By way of example, and not by limitation, for ex vivo gene therapy approaches, the following procedures may be utilized for the isolation of hepatocytes to be genetically engineered to express the ApoA-I peptides of the present invention and the grafting or transplantation of the engineered hepatocytes into the recipient.

In this embodiment, hepatocytes are obtained from a donor or a recipient, the individual who is to receive the engineered hepatocytes. This procedure entails removing a portion of a liver, from which hepatocytes are removed by in situ perfusion of a collagenase solution. If the hepatocytes are to be isolated from an intact liver, a catheter is inserted into a vein which either leaves or enters the liver, collagenase solution is perfused through the catheterized vessels, resulting in release of hepatocytes. Once removed or isolated, the hepatocytes are plated and maintained under conditions suitable for transfection.

For example, several methods have been described for isolating highly enriched populations of rat hepatocytes and maintaining these cells in culture for extended periods of time. Koch, K. S. and H. L. Leffert, Annals N.Y. Academy of Sciences, 349:111–127 (1980); McGowan, J. A. et al., Journal of Cellular Physiology, 108:353–363 (1981); Bissell, D. M. and P. S. Guzelian, Annals of the New York Academy of Sciences, 349:85–98 (1981); and Enat, R. et al., Proceedings of the National Academy of Sciences, U.S.A., 81:1411–1415 (1984). Such methods can be used to isolate and maintain hepatocytes to be transduced by the method of the present invention. Hepatocytes can also be prepared using a modification of the procedure developed by Barry and Friend, described below and in Example 1, with the perfusion mixture described by Leffert. Leffert, H. L. et al., Methods in Enzymology, 58:536–544 (1979), the teachings of which are incorporated herein by reference.

The genetic material incorporated into and expressed by hepatocytes can also, optionally, include genetic material encoding a selectable marker, thus making it possible to identify and select cells which contain and express the genetic material of interest.

Thus, DNA or RNA introduced into cultured hepatocytes of the present invention includes the genetic material (DNA or RNA) of interest and, optionally, genetic material encoding a selectable marker; such DNA or RNA is referred to as incorporated genetic material (or incorporated DNA, incorporated RNA). Hepatocytes containing incorporated genetic material are referred to as transduced hepatocytes; they express the DNA or RNA of interest and produce the encoded protein or polypeptide.

Exogenous DNA encoding a polypeptide or protein of interest and, optionally, a selectable marker (e.g., neo, which encodes neomycin resistance) is incorporated in vitro into hepatocytes as described below and in Examples I–III. Hepatocytes isolated as described previously are plated at subconfluent density on matrix substrata and maintained in hormonally defined media, such as that described by Enat et al., the teachings of which are incorporated herein by reference. Enat, R., et al., Proceedings of the National Academy of Sciences, USA, 81:1411–1415 (1984). The media is changed as needed to maintain the hepatocytes.

Cells are subsequently infected with an amphotropic retrovirus which contains DNA of interest (e.g., DNA encoding a polypeptide whose expression in hepatocytes is desired) and, optionally, DNA encoding a selectable marker to be incorporated into the hepatocytes. The hepatocytes are infected with the recombinant adenovirus or retrovirus (and thus transduced with the DNA of interest) by exposing them to virus which has a recombinant genome. This results in infection of the cells by the recombinant retrovirus. It is possible to optimize the conditions for infection of the hepatocytes by using a high titer amphotropic virus.

Viral stocks, to be used in introducing genetic material of interest into hepatocytes, are harvested, as described above, supplemented with Polybrene (Aldrich) and added to the culture of hepatocytes. If the titer of the virus is high (e.g., approximately $10^6$ cfu per ml.), then virtually all hepatocytes will be infected and no selection of transduced he patocytes is required. If the titer is very low, then it is necessary to use a retroviral vector that has a selectable marker, such as neo or his. If a selectable marker is used, after exposure to the virus, the cells are grown to confluence and split into selective media (e.g., media containing G418 if the selectable marker is neo, media containing histidinol and no histidine if the selectable marker is his).

Hepatocytes expressing the incorporated genetic material are grown to confluence in tissue culture vessels; removed from the culture vessel; and introduced into the body. This can be done surgically, for example. In this case, the tissue which is made up of transduced hepatocytes capable of expressing the nucleotide sequence of interest is grafted or transplanted into the body. For example, it can be placed in the abdominal cavity in contact with/grafted onto the liver or in close proximity to the liver. Alternatively, the transduced hepatocyte-containing tissue can be attached to microcarrier beads, which are introduced (e.g., by injection) into the peritoneal space of the recipient. This approach has been shown to be successful by transplantation of wild type hepatocytes into a strain of rats (Nagase analbuminemic rats) which are deficient in albumin synthesis and demonstration of moderate levels of albumin in serum of transplanted animals. Direct injection of genetically modified hepatocytes into the liver may also be possible.

Once introduced into the body of an individual, the transduced hepatocytes provide a continuous supply of the hormone, enzyme or drug encoded by the genetic material of interest. The amount of the hormone, enzyme or drug supplied in this way can be modified or regulated as needed (e.g., by using external cues or factors which control or affect production, by controlling the size of the graft or the quantity of fibroblasts introduced into the body, or by removing the graft).

5.4. Pharmaceutical Formulations and Methods of Administration

The present invention encompasses pharmaceutical formulations for the delivery of DNA or viral vectors encoding ApoA-I or ApoA-I peptides for in vivo transformation of cells or the delivery of host cells transformed with DNA or viral vectors for in vivo and ex vivo gene therapy approaches.

The ApoA-I agonists of the invention can be used to treat any disorder in animals, especially mammals including humans, for which increasing serum HDL concentration, activating LCAT, and promoting cholesterol efflux and RCT is beneficial. Such conditions include, but are not limited to hyperlipidemia, and especially hypercholesteremia, and cardiovascular disease such as atherosclerosis (including prevention of atherosclerosis and treatment of existing disease); restenosis (e.g., preventing or treating atherosclerotic plaques which develop as a consequence of medical procedures such as balloon angioplasty); and other disorders, such as endotoxin-induced shock which often results in hypertriglyceridemia (see, e.g., Gouni et al., 1993, J. Lipid Research 94:139–146; Levine, WO96/04914).

The ApoA-I agonists can be used alone or in combination therapy with other drugs used to treat the foregoing conditions. Such therapies include, but are not limited to simultaneous or sequential administration of the drugs involved.

For example, in the treatment of hypercholesterolemia or atherosclerosis, mammalian host cells expressing the ApoA-I agonist formulations can be administered with any one or more of the cholesterol lowering therapies currently in use; e.g., bile-acid resins, niacin, and/or statins. Such a combined regimen may produce particularly beneficial therapeutic effects since each drug acts on a different target in cholesterol synthesis and transport; i.e., bile-acid resins affect cholesterol recycling, the chylomicron and LDL population; niacin primarily affects the VLDL and LDL population; the statins inhibit cholesterol synthesis, decreasing the LDL population (and perhaps increasing LDL receptor expression); whereas the ApoA-I agonists affect RCT, increase HDL, increase LCAT activity and promote cholesterol efflux.

In another embodiment, mammalian host cells expressing ApoA-I agonists may be used in conjunction with fibrate to treat hyperlipidemia, hypercholesterolemia and/or cardiovascular disease such as atherosclerosis. This regimen may likewise prove very beneficial since fibrate does not have a proven effect on cardiovascular disease.

In yet another embodiment, the ApoA-I agonists of the invention can be used in combination with the anti-microbials and anti-inflammatory agents currently used to treat septic shock induced by endotoxin.

The ApoA-I agonists expressed by the nucleotide sequences of the invention can be formulated as peptides or as peptide-lipid complexes which can be administered to subjects in a variety of ways to deliver the ApoA-l agonist to the circulation. Exemplary formulations and treatment regimens are described below.

The mammalian host cells expressing ApoA-I peptide agonists, the DNA-lipid complexes or "naked" plasmid DNA encoding the ApoA-I agonists of the invention may be administered by any suitable route that ensures bioavailability in the circulation. This can best be achieved by parenteral routes of administration, including intravenous (IV), intramuscular (IM), intradermal, subcutaneous (SC) and intraperitoneal (IP) injections. However, other routes of administration may be used. For example, absorption through the gastrointestinal tract can be accomplished by oral routes of administration (including but not limited to ingestion, buccal and sublingual routes) provided appropriate formulations (e.g., enteric coatings) are used to avoid or minimize degradation of the active ingredient, e.g., in the harsh environments of the oral mucosa, stomach and/or small intestine. Furthermore, one may administer the agent of the present invention in a targeted drug delivery system, for example in a liposome targeted to the liver. The liposomes will be targeted to an taken up selectively by liver cells. Alternatively, administration via mucosal tissue such as vaginal and rectal modes of administration may be utilized to avoid or minimize degradation in the gastrointestinal tract. In yet another alternative, the formulations of the invention can be administered transcutaneously (e.g., transdermally), or by inhalation. It will be appreciated that the preferred route may vary with the condition, age and compliance of the recipient.

The actual dose of ApoA-I agonists or peptide-lipid complex used will vary with the route of administration, and should be adjusted to achieve circulating plasma concentrations of 100 mg to 2 g/l. Data obtained in animal model systems described herein show that the ApoA-I agonists of the invention associate with the HDL component, and have a projected half-life in humans of about five days. Thus, in one embodiment, the ApoA-I agonists can be administered by injection at a dose between 0.5 to 100 mg/kg (dose/IV; IM;SC) once a week. In another embodiment, desirable serum levels may be maintained by continuous infusion to provide about 0.5–100 mg/kg/hr or by intermittent infusion providing about 0.5–100 mg/kg.

Toxicity and therapeutic efficacy of the various ApoA-I agonists can be determined using standard pharmaceutical procedures in cell culture or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. ApoA-I peptide agonists which exhibit large therapeutic indices are preferred.

5.4.1. Pharmaceutical Formulations

The pharmaceutical formulation of the invention contain the mammalian host cells expressing the ApoA-I peptide agonist, the DNA encoding the ApoA-I peptide either naked or complexed with lipids, liposomes, or nonlipid cationic polymers as the active ingredient in a pharmaceutically acceptable carrier suitable for administration and delivery in vivo.

Injectable preparations include sterile suspensions, solutions or emulsions of the active ingredient in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the ApoA-I agonist peptide may be lyophilized, or the co-lyophilized peptide-lipid complex may be prepared. The stored preparations can be supplied in unit dosage forms and reconstituted prior to use in vivo.

For prolonged delivery, the active ingredient can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt form of the ApoA-I agonist.

Alternatively, transdermal delivery systems manufactured as an adhesive disc or patch which slowly releases the active ingredient for percutaneous absorption may be used. To this end, permeation enhancers may be used to facilitate transdermal penetration of the active ingredient. A particular benefit may be achieved by incorporating the ApoA-I agonists of the invention or the peptide-lipid complex into a nitroglycerin patch for use in patients with ischemic heart disease and hypercholesterolemia.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner. For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.5. Other Uses

The ApoA-I peptides and agonists encoded by the nucleotide sequences of the invention can be used in assays in vitro to measure serum HDL, e.g., for diagnostic purposes. Because the ApoA-I agonists associate with the HDL component of serum, the agonists can be used as "markers" for the HDL population. Moreover, the agonists can be used as markers for the subpopulation of HDL that are effective in RCT. To this end, the agonist can be added to or mixed with a patient serum sample; after an appropriate incubation time, the HDL component can be assayed by detecting the incorporated ApoA-I agonist. This can be accomplished using labeled agonist (e.g., radiolabels, fluorescent labels, enzyme labels, dyes, etc.), or by immunoassays using antibodies (or antibody fragments) specific for the agonist.

Alternatively, labeled agonist can be used in imaging procedures (e.g., CAT scans, MRI scans) to visualize the circulatory system, or to monitor RCT, or to visualize accumulation of HDL at fatty streaks, atherosclerotic lesions, etc. (where the HDL should be active in cholesterol efflux).

6. EXAMPLE

LCAT Activation Assay

Examples of peptides which may be encoded by the nucleotides of the present invention are listed in Table VIII which also includes peptides which are chemically synthesized. Only those peptides composed of amino acids which may be genetically encoded or which exhibit an LCAT activity of less than 38% as compared with native ApoA-I are encompassed by the present invention. All of the peptides listed were analyzed in vitro for their ability to activate LCAT. In the LCAT assay, substrate vesicles (small unilamellar vesicles or "SUVs") composed of egg phophatidylcholine or 1-Palmitoyl-2-oleyl-phosphatidyl-choline (POPC) and radiolabelled cholesterol are preincubated with equivalent masses either of peptide or ApoA-I (isolated from human plasma). The reaction is initiated by addition of LCAT (purified from human plasma). Native ApoA-I, which was used as positive control, represents 100% activation activity. "Specific activity" (i.e., units of activity (LCAT activation)/unit of mass) of the peptides can be calculated as the concentration of peptide that achieves maximum LCAT activation. For example, a series of concentrations of the peptide (e.g., a limiting dilution) can be assayed to determine the "specific activity" for the peptide—the concentration which achieves maximal LCAT activation (i.e., percentage conversion of cholesterol to cholesterol ester) at a specific timepoint in the assay (e.g., 1 hr.). When plotting percentage conversion of cholesterol at, e.g., 1 hr., against the concentration of peptide used, the "specific activity" can be identified as the concentration of peptide that achieves a plateau on the plottal curve.

6.1. Preparation of Substrate Vesicles

The vesicles used in the LCAT assay are SUVs composed of egg phosphatidylcholine (EPC) or 1-palmitoyl-2-oleyl-phosphatidylcholine (POPC) and cholesterol with a molar ratio of 20:1. To prepare a vesicle stock solution sufficient for 40 assays, 7.7 mg EPC (or 7.6 mg POPC; 10 µmol), 78 µg (0.2 µmol) 4-$^{14}$C-cholesterol, 116 µg cholesterol (0.3 µmol) are dissolved in 5 ml xylene and lyophilized. Thereafter 4 ml of assay buffer is added to the dry powder and sonicated under nitrogen atmosphere at 4° C. Sonication conditions: Branson 250 sonicator, 10 mm tip, 6.5 minutes; Assay buffer: 10 mM Tris, 0.14M NaCl, 1 mM EDTA, pH 7.4). The sonicated mixture is centrifuged 6 times for 5 minutes each time at 14,000 rpm (16,000×g) to remove titanium particles. The resulting clear solution is used for the enzyme assay.

6.2. Purification of LCAT

For the LCAT purification, dextran sulfate/Mg$^{2+}$ treatment of human plasma is used to obtain lipoprotein deficient serum (LPDS), which is sequentially chromatographed on Phenylsepharose, Affigelblue, ConcanavalinA sepharose and anti-ApoA-I affinity chromatography, as summarized for a representative purification in Table VII, below:

TABLE VII

LCAT PURIFICATION

| Fraction | Total Volume (mL) | Total Protein (mg) | Total Activity (nmol CE/mg * h) | Yield (%) | Purification (fold) |
|---|---|---|---|---|---|
| Plasma | 550 | 44550 | 63706 | | |
| LPDS | 500 | 31000 | 62620 | 98 | 1.4 |
| Phenyl sepharose | 210 | 363 | 51909 | 82 | 100 |
| Affigel blue | 95 | 153 | 25092 | 39 | 115 |
| ConA sepharose | 43 | 36 | 11245 | 18 | 220 |
| Anti-A-I Affinity | 120 | 3.5 | 5500 | 9 | 1109 |

6.2.1. Preparation of LPDS

To prepare LPDS, 500 ml plasma is added to 50 ml dextran sulfate (MW=500000) solution. Stir 20 minutes. Centrifuge for 30 minutes at 3000 rpm (16,000×g) at 4° C. Use supernatant (LPDS) for further purification (ca. 500 ml).

6.2.2. Phenylsepharose Chromatography

The following materials and conditions were used for the phenylsepharose chromatography.

| | |
|---|---|
| solid phase: | Phenylsepharose fast flow, high subst. grade, Pharmacia |
| column: | XK26/40, gel bed height: 33 cm, V = ca. 175 ml |
| flow rates: | 200 ml/hr (sample) |
| wash: | 200 ml/hr (buffer) |
| elution: | 80 ml/hr (distilled water) |
| buffer: | 10 mM Tris, 140 mM NaCl, 1 mM EDTA pH7.4, 0.01% Na-azide. |

Equilibrate the column in Tris-buffer, add 29 g NaCl to 500 ml LPDS and apply to the column. Wash with several volumes of Tris buffer until the absorption at 280 nm wavelength is approximately at the baseline, then start the elution with distilled water. The fractions containing protein are pooled (pool size: 180 ml) and used for Affigelblue chromatography.

6.2.3. Affigelblue Chromatography

The Phenylsepharose pool is dialyzed overnight at 4° C. against 20 mM Tris-HCl, pH7.4, 0.01% Na-azide. The pool volume is reduced by ultrafiltration (Amicon YM30) to 50–60 ml and loaded on an Affigelblue column.

| | |
|---|---|
| solid phase: | Affigelblue, Biorad, 153–7301 column, XK26/20, gel bed height: ca. 13 cm; column volume: approx. 70 ml. |
| flow rates: | loading: 15 ml/h<br>wash: 50 ml/h |

Equilibrate column in Tris-buffer. Apply Phenylsepharose pool to column. Start in parallel to collect fractions. Wash with Tris-buffer. The pooled fractions (170 ml) were used for ConA chromatography.

6.2.4. ConA Chromatography

The Affigelblue pool was reduced via Amicon (YM30) to 30–40 ml and dialyzed against ConA starting buffer (1 mM Tris HCl pH7.4; 1 mM MgCl$_2$, 1 mM MnCl$_2$, 1 mM CaCl$_2$, 0.01% Na-azide) overnight at 4° C.

| | |
|---|---|
| solid phase: | ConA sepharose (Pharmacia) |
| column: | XK26/20, gel bed height: 14 cm (75 ml) |
| flow rates: | loading 40 ml/h<br>washing (with starting buffer): 90 ml/h<br>elution: 50 ml/h, 0.2 M Methyl-α-D-mannoside in 1 mM Tris, pH 7.4. |

The protein fractions of the mannoside elutions were collected (110 ml), and the volume was reduced by ultrafiltration (YM30) to 44 ml. The ConA pool was divided in 2 ml aliquots, which are stored at −20° C.

6.2.5. Anti-APoA-I Affinity Chromatography

Anti-ApoA-I affinity chromatography was performed on Affigel-Hz material (Biorad), to which the anti-ApoA-I abs have been coupled covalently.

| | |
|---|---|
| column: | XK16/20, V = 16 ml. The column was equilibrated with PBS pH 7.4. Two ml of the ConA pool was dialyzed for 2 hours against PBS before loading onto the column. |
| flow rates: | loading: 15 ml/hour washing (PBS) 40 ml/hour. |

The pooled protein fractions (V=14 ml) are used for LCAT assays.

The column is regenerated with 0.1 M. Citrate buffer (pH 4.5) to elute bound A-I (100 ml), and immediately after this procedure reequilibrated with PBS.

6.3. Results

The results of the LCAT activation assay are presented in Table VIII, infra.

TABLE VIII

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 1 (SEQ ID NO: 1) | PVLDLFRELLNELLEZLKQKLK | 120% | 77 | 85 | 81 | 69 |
| 2 (SEQ ID NO: 2) | GVLDLFRELLNELLEALKQKLKK | 105% | | | | |
| 3 (SEQ ID NO: 3) | PVLDLFRELLNELLEWLKQKLK | 98% | 70 | 95 | 80 | 95 |
| 4 (SEQ ID NO: 4) | PVLDLFRELLNELLEALKQKLK | 93% | 80 | 95 | 97 | 94 |
| 5 (SEQ ID NO: 5) | pVLDLFRELLNELLEALKQKLKK | 90% | | | | |
| 6 (SEQ ID NO: 6) | PVLDLFRELLNEXLEALKQKLK | 80% | 57 | 93 | 70 | 99 |
| 7 (SEQ ID NO: 7) | PVLDLFKELLNELLEALKQKLK | 83% | 77 | 89 | 85 | 73 |
| 8 (SEQ ID NO: 8) | PVLDLFRELLNEGLEALKQKLK | 83% | 20 | 90 | 61 | 93 |
| 9 (SEQ ID NO: 9) | PVLDLFRELGNELLEALKQKLK | 83% | | | | |
| 10 (SEQ ID NO: 10) | PVLDLFRELLNELLEAZKQKLK | 79% | 60 | 87 | 70 | 71 |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 11 | (SEQ ID NO: 11) PVLDLFKELLQELLEALKQKLK | 72% | | | | |
| 12 | (SEQ ID NO: 12) PVLDLFRELLNELLEAGKQKLK | 70% | | | | |
| 13 | (SEQ ID NO: 13) GVLDLFRELLNEGLEALKQKLK | 67% | | | | |
| 14 | (SEQ ID NO: 14) PVLDLFRELLNELLEALOQOLO | 61% | 70 | 96 | 80 | |
| 15 | (SEQ ID NO: 15) PVLDLFRELWNELLEALKQKLK | 60% | 55 | 60 | 64 | 68 |
| 16 | (SEQ ID NO: 16) PVLDLLRELLNELLEALKQKLK | 59% | | | | |
| 17 | (SEQ ID NO: 17) PVLELFKELLQELLEALKQKLK | 59% | | | | |
| 18 | (SEQ ID NO: 18) GVLDLFRELLNELLEALKQKLK | 58% | | | | |
| 19 | (SEQ ID NO: 19) pVLDLFRELLNEGLEALKQKLK | 58% | | | | |
| 20 | (SEQ ID NO: 20) PVLDLFREGLNELLEALKQKLK | 57% | | | | |
| 21 | (SEQ ID NO: 21) pVLDLFRELLNELLEALKQKLK | 57% | | | | |
| 22 | (SEQ ID NO: 22) PVLDLFRELLNELLEGLKQKLK | 54% | | | | |
| 23 | (SEQ ID NO: 23) PLLELFKELLQELLEALKQKLK | 54% | | | | |
| 24 | (SEQ ID NO: 24) PVLDLFRELLNELLEALQKKLK | 53% | | | | |
| 25 | (SEQ ID NO: 25) PVLDFFRELLNEXLEALKQKLK | 51% | 46 | 82 | | 93 |
| 26 | (SEQ ID NO: 26) PVLDLFRELLNELLELLKQKLK | 47% | | | | |
| 27 | (SEQ ID NO: 27) PVLDLFRELLNELZEALKQKLK | 44% | 72 | 92 | 82 | 81 |
| 28 | (SEQ ID NO: 28) PVLDLFRELLNELWEALKQKLK | 40% | 82 | 98 | 90 | 81 |
| 29 | (SEQ ID NO: 29) AVLDLFRELLNELLEALKQKLK | 39% | | | | |
| 30 | (SEQ ID NO: 30) PVLDLFRELLNELLEALKQKLK[1] | 38% | 85 | 90 | 98 | 90 |
| 31 | (SEQ ID NO: 31) PVLDLFLELLNEXLEALKQKLK | 34% | 49 | 98 | | 90 |
| 32 | (SEQ ID NO: 32) XVLDLFRELLNELLEALKQKLK | 33% | | | | |
| 33 | (SEQ ID NO: 33) PVLDLFREKLNELLEALKQKLK | 33% | | | | |
| 34 | (SEQ ID NO: 34) PVLDZFRELLNELLEALKQKLK | 32% | 58 | 67 | 68 | 62 |
| 35 | (SEQ ID NO: 35) PVLDWFRELLNELLEALKQKLK | 31% | 49 (sp) | 59 | 61 | |
| 36 | (SEQ ID NO: 36) PLLELLKELLQELLEALKQKLK | 31% | 95 | 100 | | 95 |
| 37 | (SEQ ID NO: 37) PVLDLFREWLNELLEALKQKLK | 29% | 65 | 75 | 76 | 73 |
| 38 | (SEQ ID NO: 38) PVLDLFRELLNEXLEAWKQKLK | 29% | 25 | 49 | 21 | 49 |
| 39 | (SEQ ID NO: 39) PVLDLFRELLEELLKALKKKLK | 25% | 66 | 69 | 68 | 72 |
| 40 | (SEQ ID NO: 40) PVLDLFNELLRELLEALQKKLK | 25% | 66 | 84 | 79 | 77 |
| 41 | (SEQ ID NO: 41) PVLDLWRELLNEXLEALKQKLK | 25% | 53 | 73 | 85 | 69 |
| 42 | (SEQ ID NO: 42) PVLDEFREKLNEXWEALKQKLK | 25% | 15 | 74 | 27 | 76 |
| 43 | (SEQ ID NO: 43) PVLDEFREKLWEXLEALKQKLK | 25% | | | | |
| 44 | (SEQ ID NO: 44) pvldefreklflfeXlealkqklk | 25% | 20 | 86 | | |
| 45 | (SEQ ID NO: 45) PVLDEFREKLNEXLEALKQKLK | 24% | 24 | 84 | 25 | 86 |
| 46 | (SEQ ID NO: 46) PVLDFREKLNEXLEALKQKLK | 23% | 30 | 86 | 58 | 85 |
| 47 | (SEQ ID NO: 47) ~VLDLFRELLNEGLEALKQKLK | 23% | | | | |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 48 | (SEQ ID NO: 48) pVLDLFRELLNELLEALKQKLK | 22% | | | | |
| 49 | (SEQ ID NO: 49) PVLDLFRNLLEKLLEALEQKLK | 22% | 57 | 65 | 52 | 57 |
| 50 | (SEQ ID NO: 50) PVLDLFRELLWEXLEALKQKLK | 21% | 68 | 84 | 89 | 76 |
| 51 | (SEQ ID NO: 51) PVLDLFWELLNEXLEALKQKLK | 20% | 63 | 82 | 81 | 73 |
| 52 | (SEQ ID NO: 52) PVWDEFREKLNEXLEALKQKLK | 20% | sp | sp | sp | |
| 53 | (SEQ ID NO: 53) VVLDLFRELLNELLEALKQKLK | 19% | | | | |
| 54 | (SEQ ID NO: 54) PVLDLFRELLNEWLEALKQKLK | 19% | 76 | 71 | 84 | 78 |
| 55 | (SEQ ID NO: 55) P~~~LFRELLNELLEALKQKLK | 19% | 38 | 72 | 78 | 75 |
| 56 | (SEQ ID NO: 56) PVLDLFRELLNELLEALKQKKK | 18% | | | | |
| 57 | (SEQ ID NO: 57) PVLDLFRNLLEELLKALEQKLK | 18% | | | | |
| 58 | (SEQ ID NO: 58) PVLDEFREKLISTEXLEALKQKL | 18% | | | | |
| 59 | (SEQ ID NO: 59) LVLDLFRELLNELLEALKQKLK | 17% | | | | |
| 60 | (SEQ ID NO: 60) PVLDLFRELLNELLEALKQ~~~ | 16% | 39 | 83 | 66 | 84 |
| 61 | (SEQ ID NO: 61) PVLDEFRWKLNEXLEALKQKLK | 16% | | | | |
| 62 | (SEQ ID NO: 62) PVLDEWREKLNEXLEALKQKLK | 16% | 15 | 85 | 43 | |
| 63 | (SEQ ID NO: 63) PVLDFFREKLNEXLEALKQKLK | 16% | | | | |
| 64 | (SEQ ID NO: 64) PWLDEFREKLNEXLEALKQKLK | 15% | | | | |
| 65 | (SEQ ID NO: 65) ~VLDEFREKLNEXLEALKQKLK | 15% | | | | |
| 66 | (SEQ ID NO: 66) PVLDLFRNLLEELLEALQKKLK | 15% | 64 | 82 | 66 | 70 |
| 67 | (SEQ ID NO: 67) ~VLDLFRELLNELLEALKQKLK | 14% | 81 | 90 | 84 | 94 |
| 68 | (SEQ ID NO: 68) PVLDEFRELLKEXLEALKQKLK | 14% | | | | |
| 69 | (SEQ ID NO: 69) PVLDEFRKKLNEXLEALKQKLK | 13% | | | | |
| 70 | (SEQ ID NO: 70) PVLDEFRELLYEXLEALKQKLK | 12% | 27 | 78 | 33 | 66 |
| 71 | (SEQ ID NO: 71) PVLDEFREKLNELXEALKQKLK | 11% | | | | |
| 72 | (SEQ ID NO: 72) PVLDLFRELLNEXLWALKQKLK | 11% | sp | sp | sp | |
| 73 | (SEQ ID NO: 73) PVLDEFWEKLNEXLEALKQKLK | 10% | | | | |
| 74 | (SEQ ID NO: 74) PVLDKFREKLNEXLEALKQKLK | 10% | | | | |
| 75[1] | (SEQ ID NO: 75) PVLDEFREKLNEELEALKQKLK | 10% | 18 | 28 | 23 | 55 |
| 76 | (SEQ ID NO: 76) PVLDEFRELLFEXLEALKQKLK | 9% | 41 | 88 | | 66 |
| 77 | (SEQ ID NO: 77) PVLDEFREKLNKXLEALKQKLK | 9% | | | | |
| 78 | (SEQ ID NO: 78) PVLDEFRDKLNEXLEALKQKLK | | | | | |
| 79 | (SEQ ID NO: 79) PVLDEFRELLNELLEALKQKLK | 9% | | | | |
| 80 | (SEQ ID NO: 80) PVLDLFERLLNELLEALQKKLK | 9% | | | | |
| 81 | (SEQ ID NO: 81) PVLDEFREKLNWXLEALKQKLK | | | | | |
| 82 | (SEQ ID NO: 82) ~~LDEFREKLNEXLEALKQKLK | 8% | | | | |
| 83 | (SEQ ID NO: 83) PVLDEFREKLNEXLEALWQKLK | | | | | |
| 84 | (SEQ ID NO: 84) PVLDEFREKLNELLEALKQKLK | 7% | | | | |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 85 | (SEQ ID NO: 85) P~LDLFRELLNELLEALKQKLK | 7% | 58 | 61 | 64 | 69 |
| 86 | (SEQ ID NO: 86) PVLELFERLLDELLNALQKKLK | 7% | | | | |
| 87 | (SEQ ID NO: 87) pllellkellqellealkqklk | 7% | 100 | 100 | | 100 |
| 88 | (SEQ ID NO: 88) PVLDKFRELLNEXLEALKQKLK | 7% | | | | |
| 89 | (SEQ ID NO: 89) PVLDEFREKLNEXLWALKQKLK | 6% | | | | |
| 90 | (SEQ ID NO: 90) ~~~DEFREKLNEXLEALKQKLK | 6% | | | | |
| 91 | (SEQ ID NO: 91) PVLDEFRELLNEXLEALKQKLK | 6% | 43 | 100 | | 100 |
| 92 | (SEQ ID NO: 92) PVLDEFRELYNEXLEALKQKLK | 5% | | | | |
| 93 | (SEQ ID NO: 93) PVLDEFREKLNEXLKALKQKLK | 5% | | | | |
| 94[2] | (SEQ ID NO: 94) PVLDEFREKLNEALEALKQKLK | 5% | 18 | 70 | 27 | 63 |
| 95 | (SEQ ID NO: 95) PVLDLFRELLNLXLEALKQKLK | 5% | | sp | sp | |
| 96 | (SEQ ID NO: 96) pvldlfrellneXlealkqklk | 5% | 52 | 85 | 63 | 81 |
| 97 | (SEQ ID NO: 97) PVLDLFRELLNELLE~~~~~~ | 4% | | | | |
| 98 | (SEQ ID NO: 98) PVLDLFRELLNEELEALKQKLK | 2% | | | | |
| 99 | (SEQ ID NO: 99) KLKQKLAELLENLLERFLDLVP | 2% | 72 | 88 | 80 | 80 |
| 100 | (SEQ ID NO: 100) pvldlfrellnellealkqklk | 2%. | 83 | 92 | | 98 |
| 101 | (SEQ ID NO: 101) PVLDLFRELLNWXLEALKQKLK | 2% | | sp | sp | |
| 102 | (SEQ ID NO: 102) PVLDLFRELLNLXLEALKEKLK | 2% | sp | | | |
| 103 | (SEQ ID NO: 103) PVLDEFRELLNEELEALKQKLK | 1% | | | | |
| 104 | (SEQ ID NO: 104) P~~~~~~~LLNELLEALKQKLK | 1% | 21 | 49 | 29 | 55 |
| 105 | (SEQ ID NO: 105) PAADAFREAANEAAEAAKQKAK | 1% | 29 | 28 | 32 | 65 |
| 106 | (SEQ ID NO: 106) PVLDLFRELLNEELEALKQKLK | 0% | | | | |
| 107 | (SEQ ID NO: 107) klkqklaellenllerfldlvp | 0% | sp | sp | | 77 |
| 108 | (SEQ ID NO: 108) PVLDLFRWLLNEXLEALKQKLK | 0% | 28 | 55 | | 54 |
| 109[3] | (SEQ ID NO: 109) PVLDEFREKLNERLEALKQKLK | 0% | 19 | 45 | 23 | 58 |
| 110 | (SEQ ID NO: 110) PVLDEFREKLNEXXEALKQKLK | 0% | | | | |
| 111 | (SEQ ID NO: 111) PVLDEFREKLWEXWEALKQKLK | 0% | | | | |
| 112 | (SEQ ID NO: 112) PVLDEFREKLNEXSEALKQKLK | 0% | | | | |
| 113 | (SEQ ID NO: 113) PVLDEFREKLNEPLEALKQKLK | 0% | 6 | 22 | | |
| 114 | (SEQ ID NO: 114) PVLDEFREKLNEXMEALKQKLK | 0% | | | | |
| 115 | (SEQ ID NO: 115) PKLDEFREKLNEXLEALKQKLK | 0% | | | | |
| 116 | (SEQ ID NO: 116) PHLDEFREKLNEXLEALKQKLK | 0% | | | | |
| 117 | (SEQ ID NO: 117) PELDEFREKLNEXLEALKQKLK | 0% | | | | |
| 118 | (SEQ ID NO: 118) PVLDEFREKLNEXLEALEQKLK | 0% | | | | |
| 119 | (SEQ ID NO: 119) PVLDEFREKLNEELEAXKQKLK | 0% | | | | |
| 120 | (SEQ ID NO: 120) PVLDEFREKLNEELEXLKQKLK | 0% | | | | |
| 121 | (SEQ ID NO: 121) PVLDEFREKLNEELEALWQKLK | 0% | | | | |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 122 | (SEQ ID NO: 122) PVLDEFREKLNEELEWLKQKLK | 0% | | | | |
| 123 | (SEQ ID NO: 123) QVLDLFRELLNELLEALKQKLK | | | | | |
| 124 | (SEQ ID NO: 124) PVLDLFOELLNELLEALOQOLO | | | | | |
| 125 | (SEQ ID NO: 125) NVLDLFRELLNELLEALKQKLK | | | | | |
| 126 | (SEQ ID NO: 126) PVLDLFRELLNELGEALKQKLK | | | | | |
| 127 | (SEQ ID NO: 127) PVLDLFRELLNELLELLKQKLK | 47% | | | | |
| 128 | (SEQ ID NO: 128) PVLDLFRELLNELLEFLKQKLK | | | | | |
| 129 | (SEQ ID NO: 129) PVLELFNDLLRELLEALQKKLK | | | | | |
| 130 | (SEQ ID NO: 130) PVLELFNDLLRELLEALKQKLK | | | | | |
| 131 | (SEQ ID NO: 131) PVLELFKELLNELLDALRQKLK | | | | | |
| 132 | (SEQ ID NO: 132) PVLDLFRELLENLLEALQKKLK | | | | | |
| 133 | (SEQ ID NO: 133) PVLELFERLLEDLLQALNKKLK | | | | | |
| 134 | (SEQ ID NO: 134) PVLELFERLLEDLLKALNQKLK | | | | | |
| 135 | (SEQ ID NO: 135) DVLDLFRELLNELLEALKQKLK | | | | | |
| 136 | (SEQ ID NO: 136) PALELFKDLLQELLEALKQKLK | | | | | |
| 137 | (SEQ ID NO: 137) PVLDLFRELLNEGLEAZKQKLK | | | | | |
| 138 | (SEQ ID NO: 138) PVLDLFRELLNEGLEWLKQKLK | | | | | |
| 139 | (SEQ ID NO: 139) PVLDLFRELWNEGLEALKQKLK | | | | | |
| 140 | (SEQ ID NO: 140) PVLDLFRELLNEGLEALOQOLO | | | | | |
| 141 | (SEQ ID NO: 141) PVLDFFRELLNEGLEALKQKLK | | | | | |
| 142 | (SEQ ID NO: 142) PVLELFRELLNEGLEALKQKLK | | | | | |
| 143 | (SEQ ID NO: 143) PVLDLFRELLNEGLEALKQKLK* | | | | | |
| 144 | (SEQ ID NO: 144) pVLELFEWLLERLLDALQKKLK | 111% | 89 | 88 | | 95 |
| 145 | (SEQ ID NO: 145) GVLELFENLLERLLDALQKKLK | 100% | 55 | 51 | | 58 |
| 146 | (SEQ ID NO: 146) PVLELFENLLERLLDALQKKLK | 86% | 97 | 100 | 100 | 95 |
| 147 | (SEQ ID NO: 147) PVLELFENLLERLFDALQKKLK | 76% | | | | |
| 148 | (SEQ ID NO: 148) PVLELFENLLERLGDALQKKLK | 75% | 10 | 76 | 23 | 80 |
| 149 | (SEQ ID NO: 149) PVLELFENLWERLLDALQKKLK | 63% | 28 | 54 | | 47 |
| 150 | (SEQ ID NO: 150) PLLELFENLLERLLDALQKKLK | 57% | | | | |
| 151 | (SEQ ID NO: 151) PVLELFENLGERLLDALQKKLK | 55% | | | | |
| 152 | (SEQ ID NO: 152) PVFELFENLLERLLDALQKKLK | 50% | | | | |
| 153 | (SEQ ID NO: 153) AVLELFENLLERLLDALQKKLK | 49% | | | | |
| 154 | (SEQ ID NO: 154) PVLELFENLLERGLDALQKKLK | 39% | 13 | 76 | 25 | 80 |
| 155 | (SEQ ID NO: 155) PVLELFLNLWERLLDALQKKLK | 38% | | | | |
| 156 | (SEQ ID NO: 156) PVLELFLNLLERLLDALQKKLK | 35% | | | | |
| 157 | (SEQ ID NO: 157) PVLEFFENLLERLLDALQKKLK | 30% | | | | |
| 158 | (SEQ ID NO: 158) PVLELFLNLLERLLDWLQKKLK | 30% | | | | |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 159 | (SEQ ID NO: 159) PVLDLFENLLERLLDALQKKLK | 28% | | | | |
| 160 | (SEQ ID NO: 160) PVLELFENLLERLLDWLQKKLK | 28% | 65 | 73 | 75 | 61 |
| 161 | (SEQ ID NO: 161) PVLELFENLLERLLEALQKKLK | 27% | | | | |
| 162 | (SEQ ID NO: 162) PVLELFENWLERLLDALQKKLK | 27% | 68 | 83 | 81 | |
| 163 | (SEQ ID NO: 163) PVLELFENLLERLWDALQKKLK | 26% | 27 | 53 | | 55 |
| 164 | (SEQ ID NO: 164) PVLELFENLLERLLDAWQKKLK | 24% | 37 | 66 | 51 | 61 |
| 165 | (SEQ ID NO: 165) PVLELFENLLERLLDLLQKKLK | 23% | | | | |
| 166 | (SEQ ID NO: 166) PVLELFLNLLEKLLDALQKKLK | 22% | | | | |
| 167 | (SEQ ID NO: 167) PVLELFENGLERLLDALQKKLK | 18% | | | | |
| 168 | (SEQ ID NO: 168) PVLELFEQLLEKLLDALQKKLK | 17% | | | | |
| 169 | (SEQ ID NO: 169) PVLELFENLLEKLLDALQKKLK | 17% | | | | |
| 170 | (SEQ ID NO: 170) PVLELFENLLEOLLDALQOOLO | 17% | | | | |
| 171 | (SEQ ID NO: 171) PVLELFENLLEKLLDLLQKKLK | 16% | | | | |
| 172 | (SEQ ID NO: 172) PVLELFLNLLERLGDALQKKLK | 16% | | | | |
| 173 | (SEQ ID NO: 173) PVLDLFDNLLDRLLDLLNKKLK | 15% | | | | |
| 174 | (SEQ ID NO: 174) pvlelfenllerlldalqkklk | 13% | | | | |
| 175 | (SEQ ID NO: 175) PVLELFENLLERLLELLNKKLK | 13% | | | | |
| 176 | (SEQ ID NO: 176) PVLELWENLLERLLDALQKKLK | 11% | | | | |
| 177 | (SEQ ID NO: 177) GVLELFLNLLERLLDALQKKLK | 10% | | | | |
| 178 | (SEQ ID NO: 178) PVLELFDNLLEKLLEALQKKLR | 9% | | | | |
| 179 | (SEQ ID NO: 179) PVLELFDNLLERLLDALQKKLK | 8% | | | | |
| 180 | (SEQ ID NO: 180) PVLELFDNLLDKLLDALQKKLR | 8% | | | | |
| 181 | (SEQ ID NO: 181) PVLELFENLLERWLDALQKKLK | 8% | | | | |
| 182 | (SEQ ID NO: 182) PVLELFENLLEKLLEALQKKLK | 7% | | | | |
| 183 | (SEQ ID NO: 183) PLLELFENLLEKLLDALQKKLK | 6% | | | | |
| 184 | (SEQ ID NO: 184) PVLELFLNLLERLLDAWQKKLK | 4% | | | | |
| 185 | (SEQ ID NO: 185) PVLELFENLLERLLDALQOOLO | 3% | | | | |
| 186 | (SEQ ID NO: 186) PVLELFEQLLERLLDALQKKLK | | | | | |
| 187 | (SEQ ID NO: 187) PVLELFENLLERLLDALNKKLK | | | | | |
| 188 | (SEQ ID NO: 188) PVLELFENLLDRLLDALQKKLK | | | | | |
| 189 | (SEQ ID NO: 189) DVLELFENLLERLLDALQKKLK | | | | | |
| 190 | (SEQ ID NO: 190) PVLEFWDNLLDKLLDALQKKLR | | | | | |
| 191 | (SEQ ID NO: 191) PVLDLLRELLEELKQKLK* | 100% | | | | |
| 192 | (SEQ ID NO: 192) PVLDLFKELLEELKQKLK* | 100% | 36 | | | 56 |
| 193 | (SEQ ID NO: 193) PVLDLFRELLEELKQKLK* | 96% | 34 | 88 | 87 | 87 |
| 194 | (SEQ ID NO: 194) PVLELFRELLEELKQKLK* | 88% | 38 | 93 | | 93 |
| 195 | (SEQ ID NO: 195) PVLELFKELLEELKQKLK* | 87% | | | | |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 196 | (SEQ ID NO: 196) PVLDLFRELLEELKNKLK* | 81% | | | | |
| 197 | (SEQ ID NO: 197) PLLDLFRELLEELKQKLK* | 81% | 43 | 70 | | 69 |
| 198 | (SEQ ID NO: 198) GVLDLFRELLEELKQKLK* | 80% | | | | |
| 199 | (SEQ ID NO: 199) PVLDLFRELWEELKQKLK* | 76% | 35 | 77 | 80 | 79 |
| 200 | (SEQ ID NO: 200) NVLDLFRELLEELKQKLK* | 75% | | | | |
| 201 | (SEQ ID NO: 201) PLLDLFKELLEELKQKLK* | 74% | | | | |
| 202 | (SEQ ID NO: 202) PALELFKDLLEELRQKLR* | 70% | | | | |
| 203 | (SEQ ID NO: 203) AVLDLFRELLEELKQKLK* | 66% | | | | |
| 204 | (SEQ ID NO: 204) PVLDFFRELLEELKQKLK* | 63% | | | | |
| 205 | (SEQ ID NO: 205) PVLDLFREWLEELKQKLK* | 60% | | | | |
| 206 | (SEQ ID NO: 206) PLLELLKELLEELKQKLK* | 57% | | | | |
| 207 | (SEQ ID NO: 207) PVLELLKELLEELKQKLK* | 50% | | | | |
| 208 | (SEQ ID NO: 208) PALELFKDLLEELRQRLK* | 48% | | | | |
| 209 | (SEQ ID NO: 209) PVLDLFRELLNELLQKLK | 47% | 54 | 71 | 67 | 62 |
| 210 | (SEQ ID NO: 210) PVLDLFRELLEELKQKLK | 46% | 20 | 63 | 37 | 53 |
| 211 | (SEQ ID NO: 211) PVLDLFRELLEELOQOLO* | 45% | | | | |
| 212 | (SEQ ID NO: 212) PVLDLFOELLEELOQOLK* | 43% | | | | |
| 213 | (SEQ ID NO: 213) PALELPKDLLEEFRQRLK* | 42% | | | | |
| 214 | (SEQ ID NO: 214) pVLDLFRELLEELKQKLK* | 39% | | | | |
| 215 | (SEQ ID NO: 215) PVLDLFRELLEEWKQKLK* | 38% | 28 | 63 | 53 | 68 |
| 216 | (SEQ ID NO: 216) PVLELFKELLEELKQKLK | 35% | | | | |
| 217 | (SEQ ID NO: 217) PVLDLFRELLELLKQKLK | 30% | 52 | 78 | 76 | 70 |
| 218 | (SEQ ID NO: 218) PVLDLFRELLNELLQKLK* | 29% | | | | |
| 219 | (SEQ ID NO: 219) PVLDLFRELLNELWQKLK | 24% | | | | |
| 220 | (SEQ ID NO: 220) PVLDLFRELLEELQKKLK | 22% | 27 | 64 | 54 | 64 |
| 221 | (SEQ ID NO: 221) DVLDLFRELLEELKQKLK* | 12% | | | | |
| 222 | (SEQ ID NO: 222) PVLDAFRELLEALLQLKK | 8% | | | | |
| 223 | (SEQ ID NO: 223) PVLDAFRELLEALAQLKK | 8% | 21 | 56 | 23 | 51 |
| 224 | (SEQ ID NO: 224) PVLDFREGWEELKQKLK | 8% | | | | |
| 225 | (SEQ ID NO: 225) PVLDAFRELAEALAQLKK | 1% | | | | |
| 226 | (SEQ ID NO: 226) PVLDAFRELGEALLQLKK | 1% | | | | |
| 227 | (SEQ ID NO: 227) PVLDLFRELGEELKQKLK* | 0% | | | | |
| 228 | (SEQ ID NO: 228) PVLDLFREGLEELKQKLK* | 0% | | | | |
| 229 | (SEQ ID NO: 229) PVLDLFRELLEEGKQKLK* | 0% | | | | |
| 230 | (SEQ ID NO: 230) PVLELFERLLEDLQKKLK | | | | | |
| 231 | (SEQ ID NO: 231) PVLDLFRELLEKLEQKLK | | | | | |

TABLE VIII-continued

LCAT ACTIVATION EXHIBITED BY EXEMPLARY CORE PEPTIDES

| PEPTIDE | AMINO ACID SEQUENCE | ACTIVITY (%) LCAT | He (%) free | He (%) mics | He (%) SUVs | He (%) TFE |
|---|---|---|---|---|---|---|
| 232 | (SEQ ID NO: 232) PLLELFKELLEELKQKLK* | | | | | |
| 237[4] | (SEQ ID NO: 237) LDDLLQKWAEAFNQLLKK | 11% | 30 | 66 | 45 | — |
| 238[5] | (SEQ ID NO: 238) EWLKAFYEKVLEKLKELF* | 19% | 49 | 72 | 60 | 58 |
| 239[6] | (SEQ ID NO: 239) EWLEAFYKKVLEKLKELF* | 11% | 44 | 49 | | sp |
| 240 | (SEQ ID NO: 240) DWLKAFYDKVAEKLKEAF* | 10% | 16 | 68 | 59 | 57 |
| 241 | (SEQ ID NO: 241) DWFKAFYDKVFEKFKEFF | 8% | | | | |
| 242[7] | (SEQ ID NO: 242) GIKKFLGSIWKFIKAFVG | 7% | | | | |
| 243 | (SEQ ID NO: 243) DWFKAFYDKVAEKFKEAF | 5% | 10 | 64 | 50 | |
| 244[8] | (SEQ ID NO: 244) DWLKAFYDKVAEKLKEAF | 5% | 9 | 40 | 13 | 48 |
| 245 | (SEQ ID NO: 245) DWLKAFYDKVFEKFKEFF | 4% | 38 | 77 | 70 | sp |
| 246[9] | (SEQ ID NO: 246) EWLEAFYKKVLEKLKELF | 4% | 18 | 44 | 47 | |
| 247 | (SEQ ID NO: 247) DWFKAFYDKFFEKFKEFF | 3% | | | | |
| 248[10] | (SEQ ID NO: 248) EWLKAFYEKVLEKLKELF | 3% | 18 | 45 | 13 | |
| 249[11] | (SEQ ID NO: 249) EWLKAEYEKVEEKLKELF* | | | | | |
| 250[12] | (SEQ ID NO: 250) EWLKAEYEKVLEKLKELF* | | | | | |
| 251[13] | (SEQ ID NO: 251) EWLKAFYKKVLEKLKELF* | | | | | |
| 252 | (SEQ ID NO: 252) PVLDLFRELLEQKLK* | | | | | |
| 253 | (SEQ ID NO: 253) PVLDLFRELLEELKQK* | | | | | |
| 254 | (SEQ ID NO: 254) PVLDLFRELLEKLKQK* | | | | | |
| 255 | (SEQ ID NO: 255) PVLDLFRELLEKLQK* | | | | | |
| 256 | (SEQ ID NO: 256) PVLDLFRELLEALKQK* | | | | | |
| 257 | (SEQ ID NO: 257) PVLDLFENLLERLKQK* | | | | | |
| 258 | (SEQ ID NO: 258) PVLDLFRELLNELKQK* | | | | | |

[1]Segrest's Consensus 22-mer peptide (Anantharamaiah et al., 1990, Arteriosclerosis 10(1): 95–105).
[2][A$^{13}$]-Consensus 22-mer peptide (Anantharamaiah et al., 1990, Arteriosclerosis 10(1): 95–105).
[3][R$^{13}$]-Consensus 22-mer peptide (Anantharamaiah et al., 1990, Arteriosclerosis 10(1): 95–105).
[4]ID-3 peptide (Labeur et al., 1997, Arteriosclerosis, Thrombosis and Vascular Biology 17(3): 580–588).
[5]Ac-18AMOD-C(O)NH$_2$ peptide (Epand et al., 1987, J. Biol. Chem. 262(19): 9389–9396).
[6]Ac-18AM4-C(O)NH$_2$ peptide (Brasseur, 1993, Biochim. Biophys. Acta 1170: 1–7).
[7]18L peptide (Segrest et al., 1990, Proteins: Structure, Function and Genetics 8: 103–117).
[8]18A peptide (Anantharamaiah et al., 1985, J. Biol. Chem. 260(18): 10248–10255).
[9]18AM4 peptide (Rosseneu et al., WO93/25581; Corijn et al., 1993, Biochim. Biophys. Acta 1170: 8–16).
[10][Glu$^{1,8}$; Leu$^{5,11,17}$] 18A peptide (Epand et al., 1987, J. Biol. Chem. 262(19): 9389–9396).
[11]Ac-18AM3-C(O)NH$_2$ (Rosseneu et al., WO93/25581).
[12]Ac-18AM2-C(O)NH$_2$ (Rosseneu et al., WO93/25581).
[13]Ac-18AM1-C(O)NH$_2$ (Rosseneu et al., WO93/25581).

In TABLE X, * indicates peptides that are N-terminal acetylated and C-terminal amidated; ' indicates peptides that are N-terminal dansylated; sp indicates peptides that exhibited solubility problems under the experimental conditions; X is Aib; Z is Nal; O is Orn; He (%) designates percent helicity; mics designates micelles; and ~ indicates deleted amino acids.

7. EXAMPLE

Structural and Lipid Binding Analysis of APoA-I Peptides

The structural and lipid binding characteristics of the purified peptides synthesized as described in Section 6, supra, were determined by circular dichroism (CD), fluorescence spectroscopy and nuclear magnetic resonance (NMR).

7.1. Circular Dichroism

This Example describes a preferred method for determining the percentage of α-helical secondary structure of the peptides alone and in the presence of lipids.

7.1.1 Experimental Method

Far UV circular dichroism spectra were recorded between 190 and 260 nm (in 0.5 nm or 0.2 nm increments) with a AVIV62DS spectrometer (AVIV Associates, Lakewood, N.J., USA) equipped with a thermoelectric cell holder and sample changer. The instrument was calibrated with (+)-10-camphoric acid. Between one and three scans were collected for each sample, using 10 cm, 5 cm, 1 cm and 0.1 cm path length quartz Suprasil cells, respectively, for peptide concentrations of $10^{-7}$ M to $10^{-4}$ M. The bandwidth was fixed at 1.5 nm and the scan speed to 1s per wavelength step. The reported data are the mean of at least 2 or 3 independent measurements.

After background substraction, spectra were converted to molar ellipticity (θ) per residue in deg. $cm^{-2}$ $dmol^{-1}$. The peptide concentration was determined by amino acid analysis and also by absorption spectrometry on a Perkin Elmer Lambda 17 UV/Visible spectrophotometer when the peptide contained a chromophore (tryptophane, dansyl, naphtylalanine).

CD spectra were obtained with free, unbound peptide (5 μM in 5 mM phosphate buffer, pH 7.4); with peptide-SUV complexes (20:1 EPC:Chol., Ri=50); with peptide-micelle complexes (1-myristoyl-2-hydroxy-sn-glycero-3-phosphatidyl choline, Ri=100); and with free, unbound peptide in the presence of 2,2,2-trifluoroethanol (TFE) (5 μM peptide, 90% vol TFE).

The SUVs were obtained by dispersing the lipids (10 mM, 20:1 EPC:Chol., Avanti Polar Lipids, AL) in phosphate buffer (5 mM, pH 7.4) with bubbling $N_2$ for 5 min., followed by sonication (1.5 hr.) in a bath sonicator. The homogeneity of the preparation was checked by FPLC.

The micelles were obtained by dispersing the lipid (6 mM 1-myristoyl-2-hydroxy-sn-glycero-3-phosphatidyl choline, Avanti Polar Lipids, AL) in phosphate buffer (5 mM, pH 7.4) with bubbling $N_2$ for 5 min., followed by vortexing.

To obtain the peptide-SUV complexes, SUVs were added to the peptide (5 μM in 5 mM phosphate buffer, pH 7.4) at a phospholipid-peptide molar ratio (Ri) of 100.

To obtain the peptide-micelle complexes, micelles were added to the peptide (5 μM in 5 mM phosphate buffer, pH 7.4) at a Ri of 100.

All spectra were recorded at 37° C. The stability of peptide 210 (SEQ ID NO:210) as a function of temperature (both free in buffer and in micelles) was determined by recording spectra at a series of different temperatures.

The degree of helicity of peptide 210 (SEQ ID NO:210) as a function of concentration was also determined.

7.1.2 Helicity Determination

The degree of helicity of the peptides in the various conditions was determined from the mean residue ellipticity at 222 nm (Chen et al., 1974, Biochemistry 13:3350–3359) or by comparing the CD spectra obtained to reference spectra available on databases (16 helical reference spectra from Provencher & Glockner, 1981, Biochemistry 20:33–37; denatured protein reference spectra from Venyaminov et al., 1993, Anal. Biochem. 214:17–24) using the CONTIN curve-fitting algorithm version 2DP, CD-1 pack (August 1982) (Provencher, 1982, Comput. Phys. Commun. 27:213–227, 229–242). Acceptable fit was determined using the statistical analysis methodology provided by the CONTIN algorithm. The error of all methods was ±5% helicity.

7.1.3 Results

The degree of helicity (%) of the free, unbound peptides (free), the peptide-SUV complexes (SUVs), the peptide-micelle complexes (mics) and the peptide-TFE solution (TFE) are reported in TABLE VIII.

Peptide 210 (SEQ ID NO:210) contains significant α-helical structure (63% helicity) in micelles. Moreover, the α-helical structure is completely stable over a temperature range of 5°–45° C. (data not shown). The helicity of peptide 210 (SEQ ID NO:210) also increases in the presence of TFE, which is a solvent that, due to having a signficantly lower dielectric constant (ε=26.7) than water (ε=78.4), stabilizes α-helices and intrapeptide hydrogen bonds at concentrations between 5–90% (v/v).

Referring to TABLE VIII, infra, it can be seen that those peptides which exhibit a high degree of LCAT activation (≧38%) generally possess significant α-helical structure in the presence of lipids (≧60% helical structure in the case of unblocked peptides containing 22 or more amino acids or blocked peptides containing 18 or fewer amino acids; ≧40% helical structure in the case of unblocked peptides containing 18 or fewer amino acids), whereas peptides which exhibit little or no LCAT activation possess little α-helical structure. However, in some instances, peptides which contain significant α-helical structure in the presence of lipids do not exhibit significant LCAT activation. As a consequence, the ability of the core peptides of the invention to adopt an α-helical structure in the presence of lipids is considered a critical feature of the core peptides of the invention, as the ability to form an α-helix in the presence of lipids. appears to be a prerequisite for LCAT activation.

7.2 Fluorescence Spectroscopy

The lipid binding properties of the peptides described in Section 6, supra, were tested by fluorescence measurements with labeled peptides, in the present case Tryptophane (Trp or W) or Naphtylalanine (Nal). The fluorescence spectra were recorded on a Fluoromax from Spex (Jobin-Yvon) equipped with a Xenon lamp of 150 W, two monochromators (excitation and emission), a photomultiplier R-928 for detection sensitive in the red up to 850 nm and a thermoelectric magnetic stirred cell holder. Quartz Suprasil cuvettes were used for measurements in the micromolar concentration range. A device of variable slits (from 0.4 to 5 nm) allows modulation of the incident and emitted intensities according to the concentration of peptide used. The reported values are in general the average of between 2 to 4 spectra. The peptide concentration is determined by absorption spectrometry on a Philips PU 8800 using the absorption band of the Trp ($\epsilon_{280\ nm}$=5,550 M$^{-1}$ cm$^{-1}$ in Tris buffer) or the Nal ($\epsilon_{224\ nm}$=92, 770 M$^{-1}$ cm$^{-3}$ in methanol).

Fluorescence spectra of the peptides were recorded between 290 nm and 450 nm in Tris-HCl buffer (20 mM, pH=7.5), in the presence and absence of lipidic vesicles. The small unilamellar vesicles were formed after rehydration in buffer of the lyophilized phospholipids, dispersion and tip sonication under a N$_2$ stream. The lipids used were either Egg PC/Chol. (20:1) or POPC/Chol. (20:1). The spectra were recorded at a peptide concentration of 2 μM and at a temperature of 37° C. The fluorescence reference standard in the case of Trp was N-acetyltryptophanylamide (NATA).

Lipid binding studies were done through progressive lipidic vesicle addition to the peptide in solution at 2 μM (slits: 5 nm in excitation and 1.5 nm in emission). Dilution effects were taken into account for the fluorescence intensity determination. The lipid concentrations were varied from 10 to 600 μM and the molar ratio of lipid to peptide (Ri) was varied from 5 to 300. The wavelength of excitation was set at 280 nm for both Trp and Nal.

7.2.1 Fluorescence Spectral Analysis

The data were directly recorded and treated by an IBM-PC linked to the spectrofluorimeter through the DM3000F software from Spex. The spectra were corrected by substraction of the solvent contribution and by application of a coefficient given by the constructor taking into account the variation of the photomultiplier response versus the wavelength.

The fluorescence spectra of the peptides were characterized by the wavelength at their maximum of fluorescence emission and by their quantum yield compared to NATA in the case of peptides labeled with a tryptophane. The process of binding to lipids was analyzed by calculating the shift of the wavelength at the maximum of fluorescence emission, ($\lambda_{max}$), and the variation of the relative fluorescence intensity of emission versus the lipid concentration. The relative fluorescence intensity is defined as the following ratio: $(I-I_0)_{\lambda max}/I_{0\lambda max}$. I and $I_0$ are both measured at the ($\lambda_{max}$) corresponding to the initial free state of the peptide, i.e., without lipids. I is the intensity at a defined lipid to peptide ratio and $I_0$ is the same parameter measured in absence of lipids. The absence of these variations is relevant of the absence of interactions of the peptides with the lipids.

7.2.2 Results and Discussion

The lipid binding properties of peptide 199 (SEQ ID NO:199), which is similar in primary sequence to peptide 210 (SEQ ID NO:210) except that it contains a W (Trp) residue at position 10, are presented in TABLE IX.

TABLE IX

BINDING PROPERTIES OF PEPTIDE 199 (SEQ ID NO: 199) TO LIPIDIC VESICLES AS MEASURED BY FLUORESCENCE

| Lipid:Peptide Molar Ratio (Ri) | I/I$_o$ | $\lambda_{max}$ (nm) |
|---|---|---|
| 0 | 0 | 348 |
| 5 | 8 | 344 |
| 10 | 8 | 339 |
| 30 | 18 | 328 |
| 60 | 22 | |
| 100 | 27 | 326 |
| 200 | 41 | 325 |

In buffer at a concentration of 2 μm, the maximum of the tryptophane fluorescence emission ($\lambda_{max}$) of peptide 199 (SEQ ID NO:199) is 348 nm. This corresponds to a tryptophane which is relatively exposed to the aqueous environment when compared to NATA (λ max=350 nm). Peptide 199 (SEQ ID NO:199) binds very effectively to EPC/Chol (20:1) small unilamellar vesicles as demonstrated by the burying of the tryptophane (the wavelength for the tryptophane maximum fluorescence emission shifts from 348 nm to 325 nm) and the high fluorescence intensity exaltation (see Table IX). The burying of the tryptophane residue is maximal for a lipid to peptide molar ratio of about 100.

Other peptides which exhibited a high degree of helicity in the presence of lipids (≧60% for unblocked peptides of ≧22 acids, or blocked peptides of ≦18 amino acids; ≧40% for unblocked peptides of ≦18 amino acids) as measured by circular dichroism as disclosed in Section 7.1, supra, also demonstrated good lipid binding. Of course, among all the peptides selected by the circular dichroism screening, only the ones that could be followed by fluorescence were tested for their lipid binding properties.

7.3 Nuclear Magnetic Resonance (NMR)

This Example describes an NMR method for analyzing the structure of the core peptides of the invention.

7.3.1 NMR Sample Preparation

Samples were prepared by dissolving 5 mg of peptide in 90% H$_2$O/10% D$_2$O containing trace amounts of 2,2-Dimethyl-2-sila-5-pentane sulfonate (DSS) as an internal chemical shift reference. Some of the samples contained trifluoroethanol (TFE) (expressed as % vol). The total sample volume was 500 μl and the concentration of peptide was approximately 5 mM.

7.3.2 NMR Spectroscopy $^1$H NMR spectra were acquired at 500 MHz using a Bruker DRX500 spectrometer equipped with a B-VT2000 temperature control unit. One and two-dimensional experiments were recorded using standard pulse sequences. (Two Dimensional NMR Spectroscopy, Eds. W. R. Croasmun and RMK Carlson, 1994, VCH Publishers, New York, USA). Water suppression was achieved with low power presaturation for 2 sec. Two-dimensional experiments were carried out in the phase sensitive mode using time proportional phase incrementation (TPPI) and a spectral width of 6000 Hz in both dimensions. Typically, 40 scans were co-added for 400 t$_1$ increments with 2048 data points. Data were processed using FELIX95 software (Molecular Simulations)

on an INDIGO2 workstation (Silicon Graphics). Data were zero-filled to give a 2K×2K data matrix and apodized by a 45° shifted squared sine-bell function.

7.3.3 NMR Assignment

Complete proton resonance assignments were obtained by applying the sequential assignment technique using DQF-COSY, TOCSY and NOESY spectra as described in the literature (Wuthrich, NMR of Proteins and Nucleic Acids, 1986, John Wiley & Sons, New York, USA). Secondary chemical shifts were calculated for HN and Hα protons by subtracting the tabulated random coil chemical shifts (Wishart and Sykes, 1994, Method. Enz. 239:363–392) from the corresponding experimental values.

7.3.4 Results and Discussion

General Consideration. Amphipathic helical peptides tend to aggregate in aqueous solutions at the high concentrations necessary for NMR spectroscopy, making it difficult to obtain high resolution spectra. TFE is known to solubilize peptides, and in addition stabilizes helical conformations of peptides having helical propensity. The findings from NMR spectroscopy are demonstrated for peptide 210 (SEQ ID NO:210) as a representative example. The consensus 22-mer of Segrest (SEQ ID NO:75) was studied in comparison.

Secondary chemical shifts. Proton chemical shifts of amino acids depend both on the type of residue and on the local secondary structure within a peptide or protein (Szlagyi, 1995, Progress in Nuclear Magnetic Resonance Spectroscopy 27:325–443). Therefore, identification of regular secondary structure is possible by comparing experimental shifts with tabulated values for random coil conformation.

Formation of an α-helix typically results in an up-field (negative) shift for the Hα resonance. Observation of an upfield Hα shift for several sequential residues is generally taken as evidence of a helical structure. The Hα secondary shifts for peptide 210 (SEQ ID NO:210) in 25% TFE at 295 K show a significant negative shift for residues 4 through 15, demonstrating a highly helical conformation. Small differences are observed in the Hα chemical shifts of the consensus 22-mer (SEQ ID NO:75) compared to peptide 210 (SEQ ID NO:210).

The chemical shifts of amide hydrogens of amino acid residues residing in regions of α-helix are also shifted upfield with respect to the chemical shifts observed for random coil. In addition, a periodicity of the HN shifts can be observed, and it reflects the period of the helical turns. The amplitude of the shift variation along the sequence is related to the amphipathicity of a helical peptide. A higher hydrophobic moment leads to a more pronounced oscillation (Zhou et al., 1992, J. Am. Chem. Soc. 114:4320–4326). The HN secondary shifts for peptide 210 (SEQ ID NO:210) in 25% TFE at 295 K show an oscillatory behavior in agreement with the amphipathic nature of the helix.

The amino acid replacements lead to a more pronounced periodicity along the entire sequence. The pattern clearly reflects the stronger amphipathic nature of peptide 210 (SEQ ID NO:210) as compared to Segrest's consensus 22-mer (SEQ ID NO:75). The existence of 4–5 helical turns can be discerned.

The secondary shift of an amide proton is influenced by the length of the hydrogen bond to the carbonyl oxygen one turn away from the helix. Therefore, the periodicity of observed chemical shift values reflects different hydrogen bond lengths. This difference is associated with an overall curved helical shape of the helix backbone. The hydrophobic residues are situated on the concave side. The secondary shifts of peptide 210 (SEQ ID NO:210) indicate a curved α-helical conformation.

8 EXAMPLE

Pharmacokinetics of the ApoA-I Agonists

The following experiments can be used to demonstrate that the ApoA-I agonists are stable in the circulation and associate with the HDL component of plasma.

8.1 Synthesis of Radiolabelled Peptides

Radiolabelled peptides are synthesized by coupling a $^{14}C$-labeled amino acid as the N-terminal amino acid. The synthesis is carried out according to Lapatsanis, Synthesis, 1983, 671–173. Briefly, 250 μM of unlabeled N-terminal amino acid is dissolved in 225 μl of a 9% $Na_2CO_3$ solution and added to a solution (9% $Na_2CO_3$) of 9.25 MBq (250 μM) $^{14}C$-labeled N-terminal amino acid. The liquid is cooled down to 0° C., mixed with 600 μM (202 mg) 9-fluorenyl-methyl-N-succihimidylcarbonate (Fmoc-OSu) in 0.75 ml DMF and shaken at room temperature for 4 hr. Thereafter the mixture is extracted with Diethylether (2×5 ml) and chloroform (1×5 ml), the remaining aqueous phase is acidified with 30% HCl and extracted with chloroform (5×8 ml). The organic phase is dried over $Na_2SO_4$, filtered off and the volume was reduced under nitrogen flow to 5 ml. The purity is estimated by TLC ($CHCl_3$:MeOH:Hac, 9:1:0.1 v/v/v, stationary phase RPTLC silicagel 60, Merck, Germany).

8.2 Pharmacokinetics in Mice

In each experiment, 2.5 mg/kg radiolabelled peptide is injected intraperitoneally into mice which are fed normal mouse chow or the atherogenic Thomas-Harcroft modified diet (resulting in severely elevated VLDL and IDL cholesterol). Blood samples are taken at multiple time intervals for assessment of radioactivity in plasma.

8.3 Stability in Human Serum

The stability of the ApoA-I agonists of the invention in human serum is demonstrated as described below.

8.3.1 Experimental Methods 100 mg of $^{14}C$-labeled peptide (prepared as described in Section 9.1, supra), is mixed with 2 ml of fresh human plasma (at 37° C.) and delipidated either immediately (control sample) or after 8 days of incubation at 37° C. (test sample). Delipidation is carried out by extracting the lipids with an equal volume of 2:1 (v/v) chloroform:methanol.

The samples are loaded onto a reverse-phase C18 HPLC column and eluted with a linear gradient (25–58% over 33 min.) of acetonitrile (containing 0.1% TFA). Elution profiles are followed by absorbance (220 nm) and radioactivity.

8.4 Formation of PRE-β Like Particles

The ability of the ApoA-I agonists of the invention to form pre-β-like particles is demonstrated as described below.

6.4.1 Experimental Method

Human HDL is isolated by KBr density ultra centrifugation at density d=1.21 g/ml to obtain top fraction followed by Superose 6 gel filtration chromatography to separate HDL from other lipoproteins. Isolated HDL is adjusted to a final concentration of 1.0 mg/ml with physiological saline based on protein content determined by Bradford protein assay. An aliquot of 300 µl is removed from the isolated HDL preparation and incubated with 100 µl $^{14}$C-labeled peptide for two hours at 37° C. Five separate incubations are analyzed including a blank containing 100 µl physiological saline and four dilutions of $^{14}$C-labeled peptide: (i) 0.20 µg/µl peptide:HDL, ratio=1:15; (ii) 0.30 µg/µl peptide:HDL, ratio=1:10; (iii) 0.60 µg/µl peptide:HDL, ratio=1:5; and (iv) 1.00 µg/µl peptide:HDL, ratio=1:3. Following the two hour incubation, a 200 µl aliquot of the sample (total volume=400 µl) is loaded onto a Superose 6 gel filtration column for lipoprotein separation and analysis, and 100 µl is used to determine total radioactivity loaded onto the column.

8.5 Association of APo-A-I Agonists with Human Lipoproteins

8.5.1 Experimental Methods

The ability of the ApoA-I agonists of the invention to associate with human lipoprotein fractions is determined by incubating $^{14}$C-labeled peptide with each lipoprotein class (HDL, LDL and VLDL) and a mixture of the different lipoprotein classes.

HDL, LDL and VLDL are isolated by KBr density gradient ultracentrifugation at d=1.21 g/ml and purified by FPLC on a Superose 6B column size exclusion column (chromatography is carried out at a flow rate of 0.7 ml/min. and a running buffer of 10 mM Tris (pH 8), 115 mM NaCl, 2 mM EDTA and 0.01% NaN$_3$). $^{14}$C-labeled peptide is incubated with HDL, LDL and VLDL at a peptide:phospholipid ratio of 1:5 (mass ratio) for 2 h at 37° C. The required amount of lipoprotein (volumes based on amount needed to yield 1000 µg) is mixed with 0.2 ml of peptide stock solution (1 mg/ml) and the solution is brought up to 2.2 ml using 0.9% of NaCl.

After incubating for 2 hr. at 37° C., an aliquot (0.1 ml) is removed for liquid scintillation counting to determine the total radioactivity, the density of the remaining incubation mixture is adjusted to 1.21 g/ml with KBr, and the samples are centrifuged at 100,000 rpm (300,000 g) for 24 hours at 4° C. in a TLA 100.3 rotor using a Beckman tabletop ultracentrifuge. The resulting supernatant is fractionated by removing 0.3 ml aliquots from the top of each sample for a total of 5 fractions, and 0.05 ml of each fraction is used for liquid scintillation counting. The top two fractions contain the floating lipoproteins, the other fractions (3–5) correspond to proteins/peptides in solution.

8.6 The ApoA-I Agonists of the Invention Selectively Bind HDL Lipids in Human Plasma

8.6.1 Experimental Method

To demonstrate that the ApoA-I agonists of the invention selectively bind HDL proteins in human plasma, 2 ml of human plasma is incubated with 20, 40, 60, 80, and 100 µg of $^{14}$C-labeled peptide for 2 hr. at 37° C. The lipoproteins are separated by adjusting the density to 1.21 g/ml and centrifugation in a TLA 100.3 rotor at 100,000 rpm. (300,000 g) for 36 hr. at 4° C. The top 900 µl (in 300 µl fractions) is taken for analysis. 50 µl from each 300 µl fraction is counted for radioactivity and 200 µl from each fraction is analyzed by FPLC (Superose 6/Superose 12 combination column).

9 EXAMPLE

The ApoA-I Agonists Promote Cholesterol Efflux

To demonstrate that the ApoA-I agonists of the invention promote cholesterol efflux, HepG hepatoma cells are plated into 6-well culture dishes and grown to confluence. Cells are labeled with $^3$H-cholesterol by drying the cholesterol, then adding 1% bovine serum albumin (BSA) in phosphate buffered saline (PBS), sonicating the solution, and adding 0.2 ml of this labeling solution and 1.8 ml growth medium to the cells, so that each well contains 2 µCi of radioactivity. Cells are incubated for 24 hr. with the labeling medium.

Peptide (or protein):DMPC complexes are prepared at a 1:2 peptide (or protein):DMPC ratio (w:w). To prepare the complexes, peptide or native human ApoA-I protein is added to a DMPC solution in PBS and incubated at room temperature overnight, by which time the solution will clarify. Peptide or protein concentration in the final solution is about 1 mg/ml.

Labeling media is removed from the cells and the cells are washed with PBS prior to addition of complexes. 1.6 ml of growth medium is added to each well, followed by peptide (or protein): DMPC complex and sufficient PBS to bring the final volume to 2 ml per well. The final peptide or ApoA-I concentrations are about 1, 2.5, 5, 7.5 and 25 µg/ml medium. After 24 hours of incubation at 37° C., the medium is removed, and the cells are washed with 2 ml of 1% BSA/PBS, followed by 2 washes with 2 ml each of PBS. The amount of $^3$H-cholesterol effluxed into the medium is determined by liquid scintillation counting.

EXAMPLE

Use of the ApoA-I Agonists in Animal Model Systems

The efficacy of the ApoA-I agonists of the invention was demonstrated in rabbits. The results show that administration of the ApoA-I agonists increases serum concentration of HDL-like particles.

10.1 Preparation of the Phospholipid/Peptide Complexes

Small discoidal particles consisting of phospholipid (DPPC) and peptide 146 (SEQ ID NO:146) were prepared following the cholate dialysis method. The phospholipid was dissolved in chloroform and dried under a stream of nitrogen. The peptide was dissolved in buffer (saline) at a concentration of 1–2 mg/ml. The lipid film was redissolved in buffer containing cholate (43° C.) and the peptide solution was added at a 3–1 phospholipid/peptide ratio. The mixture was incubated overnight at 43° C. and then dialyzed at 43° C. (24 hr.), room temperature (24 hr.) and 4° C. (24 hr.), with three changes of buffer (large volumes) at temperature point. The complexes were filter sterilized (0.22µ) for injection and storage at 4° C.

10.2 Isolation and Characterization of the Peptide/Phospholipid Particles

The particles were separated on a gel filtration column (Superose 6 HR). The position of the peak containing the particles was identified by measuring the phospholipid concentration in each fraction. From the elution volume, the Stokes radius can was determined. The concentration of peptide in the complex was determined by determining the phenylalanine content (by HPLC) following a 16 hr. acid hydrolysis.

10.3 Injection in the Rabbit

Male New Zealand White rabbits (2.5–3 kg) were injected intravenously with a dose of phospholipid/peptide complex (8 mg/kg bodyweight peptide 146 (SEQ ID NO:146) or 10 mg/kg bodyweight ApoA-I, expressed as peptide or protein content) in a single bolus injection not exceeding 10–15 ml. The animals were slightly sedated before the manipulations. Blood samples (collected on EDTA) were taken before and 5, 15, 30, 60, 240 and 1440 minutes after injection. The hematocrit (Hct) was determined for each sample. Samples were aliquoted and stored at −20° C. before analysis.

10.4 Analysis of the Rabbit Sera

Plasma Lipids. The total plasma cholesterol, plasma triglycerides and plasma phospholipids were determined enzymatically using commercially available assays according to the manufacturer's protocols (Boehringer Mannheim, Mannheim, Germany and Biomerieux, 69280, Marcy-l'étoile, France).

Lipoprotein Profiles. The plasma lipoprotein profiles of the fractions obtained after the separation of the plasma into its lipoprotein fractions were determined by spinning in a sucrose density gradient. The fractions were collected and in each individual fraction the phospholipid and cholesterol content was measured enzymatically.

10.5 Results

The lipoprotein profile of rabbits injected with 8 mg/kg peptide 146 (SEQ ID NO:146) (in the form of peptide/DPPC complexes) as a function of time. A substantial increase in cholesterol of the HDL cholesterol fractions (fractions >1.06 mg/ml) is apparent at 5 min. following injection and lasts for approximately 24 hr.

The cholesterol of the combined HDL fractions obtained by density gradient ultracentrifugation is presented in Table X, below. The highest increase of HDL cholesterol (90%) occurred 240 min. after administration. At 24 hr. following administration, the increase was still 71.2%.

These data indicate that administration of peptide 146/DPPC complexes (8 mg/kg) induces rapid and efficient mobilization of peripheral cholesterol.

TABLE X

HDL CHOLESTEROL IN RABBITS FOLLOWING ADMINISTRATION OF 8 mg/kg 146 (SEQ ID NO: 146) or 10 mg/kg NATIVE ApoA-I

| Time (min.) | Increase in HDL Cholesterol (%) Native ApoA-I | Increase in HDL Cholesterol (%) Peptide 146 |
|---|---|---|
| 5 | 19.3 | 31.3 |
| 15 | 16 | 60.4 |
| 60 | 15.8 | 42.9 |
| 240 | −24.1 | 90.2 |
| 1440 | * | 71.2 |

* animal died prior to time point

11 EXAMPLE

Preparation of Peptide-Lipid Complex by Co-Lyophilization Approach

The following protocol was utilized to prepare peptide-lipid complexes.

One mg of peptide 149 (PVLELFENLWERLL-DALQKKLK; SEQ ID NO:149) was dissolved in 250 µl HPLC grade methanol (Perkin Elmer) in a one ml clear glass vial with cap (Waters #WAT025054). Dissolving of the peptide was aided by occasional vortexing over a period of 10 minutes at room temperature. To this mixture an aliquot containing 3 mg dipalmitoyl-phosphatidyl-choline (DPPC; Avanti Polar Lipids, 99% Purity, product #850355) from a 100 mg/ml stock solution in methanol was added. The volume of the mixture was brought to 400 µl by addition of methanol, and the mixture was further vortexed intermittently for a period of 10 minutes at room temperature. To the tube 200 µl of xylene (Sigma-Aldrich 99% pure, HPLC-grade) was added and the tubes were vortexed for 10 seconds. Two small holes were punched into the top of the tube with a 20 gauge syringe needle, the tube was frozen for 15 seconds in liquid nitrogen, and the tube was lyophilized overnight under vacuum. To the tube 200 mls. of 0.9% NaCl solution was added. The tube was vortexed for 20 seconds. At this time the solution in the tube was milky in appearance. The tube was then incubated in a water bath for 30 minutes at 41° C. The solution became clear (i.e., similar to water in appearance) after a few minutes of incubation at 41° C.

11.1 Characterization of Complexes by Superose 6 Gel Filtration Chromatography Peptide-phospholipid complexes containing peptide 149 (SEQ ID NO:149) were prepared by colyophilization as described above. The preparation contained 1 mg peptide and 3 mgs DPPC by weight. After reconstituting the complexes in 200 µl of 0.9% NaCl, 20 µl (containing 100 µg peptide 149) of the complexes were applied to a Pharmacia Superose 6 column using 0.9% NaCl as the liquid phase at a flow rate of 0.5 mls/minute. The chromatography was monitored by absorbance or scattering of light of wavelength 280 nm. One ml fractions were collected. Aliquots containing 20 µl of the fractions were assayed for phospholipid content using the bioMerieux Phospholipides Enzymatique PAP 150 kit (#61491) according to the instructions supplied by the manufacturer. The vast majority of both phospholipid and UV absorbance were recovered together in a few fractions with peaks at approximately 15.8 mls. This elution volume corresponds to a Stokes' diameter of 87 Angstroms.

For comparison, a separate chromatogram of 20 µl of human $HDL_2$ was run under the same conditions and using the same column as the peptide 149 complexes. The $HDL_2$ was prepared as follows: 300 mls frozen human plasma (Mannheim Blutspendzentrale #1185190) was thawed, adjusted to density 1.25 with solid potassium bromide, and centrifuged 45 hours at 40,000 RPM using a Ti45. rotor (Beckman) at 20° C. The floating layer was collected, dialyzed against distilled water, adjusted to density 1.07 with solid potassium bromide, and centrifuged as described above for 70 hours. The bottom layer (at a level of one cm above the tube bottom) was collected, brought to 0.01% sodium azide, and stored at 4° C. for 4 days until chromatography. The column eluate was monitored by absorbance or scattering of light of wavelength 254 nm. A series of proteins of known molecular weight and Stokes' diameter were used as standards to calibrate the column for the calculation of Stokes' diameters of the particles (Pharmacia Gel Filtration Calibration Kit Instruction Manual, Pharmacia Laboratory Separation, Piscataway, N.J., revised April, 1985). The $HDL_2$ eluted with a retention volume of 14.8 mls, corresponding to a Stokes' diameter of 108 nm.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A nucleotide sequence encoding a multimeric ApoA-I agonist which exhibits at least about 38% LCAT activation activity as compared with human ApoA-I and which has the structural formula (IV):

  (IV)

Or a pharmaceutically acceptable salt thereof, wherein:
each m is independently an integer from 0 to 1;
Each "HH" is independently the ApoA-I agonist comprising:
(i) a 15 to 29-residue peptide or peptide analogue which forms an amphipathic α-helix in the presence of lipids and which comprises the structural formula (I):

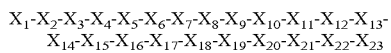

or a pharmaceutically acceptable salt thereof, wherein:
$X_1$ is Pro (P), Ala (A), Gly (G), Gln (Q), Asn (N) or Asp (D);
$X_2$ is an aliphatic residue;
$X_3$ is Leu (L) or Phe (F);
$X_4$ is an acidic residue;
$X_5$ is Leu (L) or Phe (F);
$X_6$ is Leu (L) or Phe (F);
$X_7$ is a hydrophilic residue;
$X_8$ is an acidic or a basic residue;
$X_9$ is Leu (L) or Gly (G);
$X_{10}$ is Leu (L), Trp (W) or Gly (G);
$X_{11}$ is a hydrophilic residue;
$X_{12}$ is a hydrophilic residue;
$X_{13}$ is Gly (G) or an aliphatic residue;
$X_{14}$ is Len (L), Trp (W) or Gly (G);
$X_{15}$ is a hydrophilic residue;
$X_{16}$ is a hydrophobic residue;
$X_{17}$ is a hydrophobic residue;
$X_{18}$ is Gln (Q), Asn (N) or a basic residue;
$X_{19}$ is Gln (Q), Asn (N) or a basic residue;
$X_{20}$ is a basic residue;
$X_{21}$ is an aliphatic residue;
$X_{22}$ is a basic residue;
$X_{23}$ is absent or a basic residue; or
(ii) a deleted form of structural formula (I) in which at least one and up to eight of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$ and $X_{22}$ are deleted wherein said structural formula (I) forms an amphipathic α-helix in the presence of lipids; or
(iii) an altered form of structural formula (I) in which at least one of residues $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$ or $X_{23}$ is conservatively substituted with another residue,
Each "LL" is independently a bifunctional linker.

2. A pharmaceutical composition comprising the nucleotide sequence of claim 1 and a pharmaceutically acceptable carrier, excipient or diluent.

3. The peptide according to claim 1 wherein the 15–29-residue peptide is selected from the group consisting of:
peptide 2 GVLDLFRELLNELLEALKQKLKK (SEQ ID NO:2);
peptide 3 PVLDLFRELLNELLEWLKQKLK (SEQ ID NO:3);
peptide 4 PVLDLFRELLNELLEALKQKLK (SEQ ID NO:4);
peptide 7 PVLDLFKELLNELLEALKQKLK (SEQ ID NO:7);
peptide 8 PVLDLFRELLNEGLEALKQKLK (SEQ ID NO:8);
peptide 9 PVLDLFRELGNELLEALKQKLK (SEQ ID NO:9);
peptide 11 PVLDLFKELLQELLEALKQKLK (SEQ ID NO:11);
peptide 12 PVLDLFRELLNELLEAGKQKLK (SEQ ID NO:12);
peptide 13 GVLDLFRELLNEGLEALKQKLK (SEQ ID NO:13);
peptide 15 PVLDLFRELWNELLEALKQKLK (SEQ ID NO:15);
peptide 16 PVLDLLRELLNELLEALKQKLK (SEQ ID NO:16);
peptide 17 PVLELFKELLQELLEALKQKLK (SEQ ID NO:17);
peptide 18 GVLDLFRELLNELLEALKQKLK (SEQ ID NO:18);
peptide 20 PVLDLFREGLNELLEALKQKLK (SEQ ID NO:20);
peptide 22 PVLDLFRELLNELLEGLKQKLK (SEQ ID NO:22);
peptide 23 PLLELFKELLQELLEALKQKLK (SEQ ID NO:23);
peptide 24 PVLDLFRELLNELLEALQKKLK (SEQ ID NO:24);
peptide 26 PVLDLFRELLNELLELLKQKLK (SEQ ID NO:26);
peptide 28 PVLDLFRELLNELWEALKQKLK (SEQ ID NO:28);
peptide 29 AVLDLFRELLNELLEALKQKLK (SEQ ID NO:29);
peptide 123 QVLDLPRELLNELLEALKQKLK (SEQ ID NO:123);
peptide 125 NVLDLFRELLNELLEALKQKLK (SEQ ID NO:125);
peptide 126 PVLDLFRELLNELGEALKQKLK (SEQ ID NO:126);
peptide 127 PVLDLFRELLNELLELLKQKLK (SEQ ID NO:127);

peptide 128 PVLDLFRELLNELLEFLKQKLK (SEQ ID NO:128);
peptide 129 PVLELFNDLLRELLEALQKKLK (SEQ ID NO:129);
peptide 130 PVLELFNDLLRELLEALKQKLK (SEQ ID NO:130);
peptide 131 PVLELFKELLNELLDALRQKLK (SEQ ID NO:131);
peptide 132 PVLDLFRELLENLLEALQKKLK (SEQ ID NO:132);
peptide 133 PVLELFERLLEDLLQALNKKLK (SEQ ID NO:133);
peptide 134 PVLELFERLLEDLLKALNQKLK (SEQ ID NO:134);
peptide 135 DVLDLFRELLNELLEALKQKLK (SEQ ID NO:135);
peptide 136 PALELFKDLLQELLEALKQKLK (SEQ ID NO:136);
peptide 138 PVLDLFRELLNEGLEWLKQKLK (SEQ ID NO:138);
peptide 139 PVLDLFRELWNEGLEALKQKLK (SEQ ID NO:139);
peptide 141 PVLDFFRELLNEGLEALKQKLK (SEQ ID NO:141); or
peptide 142 PVLELFRELLNEGLEALKQKLK (SEQ ID NO:142).

4. A pharmaceutical composition comprising the nucleotide sequence of claim 3 and a pharmaceutically acceptable carrier, excipient or diluent.

5. A method of treating a subject suffering from a disorderassociated with dyslipidemia comprising:
the step of administering to the subject an effective amount of a nucleotide according to claim 1.

6. A method of treating a subject suffering from a disorder associated with dyslipidemia comprising:
the step of administering to the subject an effective amount of a pharmaceutical composition according to claim 2.

7. The method according to claim 5 in which the disorder associated with dyslipidemia is hypercholesterolemia.

8. The method according to claim 5 in which the disorder associated with dyslipidemia is cardiovascular disease.

9. The method according to claim 5 in which the disorder associated with dyslipidemia is atherosclerosis.

10. The method according to claim 5 in which the disorder associated with dyslipidemia is restenosis.

11. The method according to claim 5 in which the disorder associated with dyslipidemia is an HDL or ApoA-I deficiency.

12. The method according to claim 5 in which the disorder associated with dyslipidemia is hypertriglyceridemia.

13. The method according to claim 5 in which the disorder associated with dyslipidemia is metabolic syndrome.

14. A method of treating a subject suffering from a disorder associated with endotoxemia septic shock:
comprising the step of administering to the subject an effective amount of a nucleotide sequence according to claim 1.

* * * * *